(12) United States Patent
Moberg et al.

(10) Patent No.: US 7,789,857 B2
(45) Date of Patent: Sep. 7, 2010

(54) INFUSION MEDIUM DELIVERY SYSTEM, DEVICE AND METHOD WITH NEEDLE INSERTER AND NEEDLE INSERTER DEVICE AND METHOD

(75) Inventors: Sheldon B. Moberg, Thousand Oaks, CA (US); Paul F. Bente, IV, Los Angeles, CA (US); Bradley J. Enegren, Moorpark, CA (US); Christopher G. Griffin, Sylmar, CA (US); Ian B. Hanson, Northridge, CA (US); Julian D. Kavazov, Arcadia, CA (US); R. Paul Mounce, Burbank, CA (US); William H. Stutz, Jr., Eagle Rock, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 294 days.

(21) Appl. No.: 11/646,000

(22) Filed: Dec. 26, 2006

(65) Prior Publication Data

US 2008/0051714 A1 Feb. 28, 2008

Related U.S. Application Data

(60) Provisional application No. 60/839,840, filed on Aug. 23, 2006, provisional application No. 60/854,829, filed on Oct. 27, 2006.

(51) Int. Cl.
*A61M 5/20* (2006.01)
(52) U.S. Cl. .................................................. 604/135
(58) Field of Classification Search ................. 604/135
See application file for complete search history.

(56) References Cited

U.S. PATENT DOCUMENTS 3,963,151 A 6/1976 North, Jr.

(Continued)

FOREIGN PATENT DOCUMENTS

EP 1 347 705 12/2005

(Continued)

OTHER PUBLICATIONS

Partial International Search Report dated Jan. 15, 2008 for PCT application PCT/US2007/076469.

(Continued)

*Primary Examiner*—Nicholas D Lucchesi
*Assistant Examiner*—Jason Flick
(74) *Attorney, Agent, or Firm*—Foley & Lardner LLP

(57) ABSTRACT

An infusion medium delivery system, device and method for delivering an infusion medium to a patient-user, includes a needle inserter device and method for inserting a needle and/or cannula into a patient-user to convey the infusion medium to the patient-user. The needle inserter device and method operate to insert a needle and cannula into a patient-user's skin and automatically withdraw the needle from the patient-user, leaving the cannula in place and in fluid flow communication with a reservoir. The delivery device may include a base portion and a durable portion connectable to the base portion, and wherein the base portion can be separated from the durable portion and disposed of after one or more specified number of uses. The base portion supports the reservoir and the needle inserter device, while the durable portion supports a drive device for selectively driving the infusion medium out of the reservoir and into the needle and/or cannula.

33 Claims, 30 Drawing Sheets

U.S. PATENT DOCUMENTS

| | | |
|---|---|---|
| 4,089,624 A | 5/1978 | Nichols et al. |
| 4,755,173 A | 7/1988 | Konopka et al. |
| 4,796,624 A | 1/1989 | Trott et al. |
| 4,838,857 A | 6/1989 | Strowe et al. |
| 4,976,696 A | 12/1990 | Sanderson et al. |
| 5,002,527 A | 3/1991 | Reller et al. |
| 5,053,001 A | 10/1991 | Reller et al. |
| 5,062,834 A | 11/1991 | Gross et al. |
| 5,090,963 A | 2/1992 | Gross et al. |
| 5,156,591 A | 10/1992 | Gross et al. |
| 5,176,502 A | 1/1993 | Sanderson et al. |
| 5,186,805 A | 2/1993 | Gross et al. |
| 5,190,522 A | 3/1993 | Wojcicki et al. |
| 5,203,506 A | 4/1993 | Gross et al. |
| 5,232,449 A | 8/1993 | Stern et al. |
| 5,242,406 A | 9/1993 | Gross et al. |
| 5,242,408 A | 9/1993 | Jhuboo et al. |
| 5,246,147 A | 9/1993 | Gross et al. |
| 5,254,096 A | 10/1993 | Rondelet et al. |
| 5,259,732 A | 11/1993 | Stern |
| 5,261,884 A | 11/1993 | Stern et al. |
| 5,281,202 A | 1/1994 | Weber et al. |
| 5,295,966 A | 3/1994 | Stern et al. |
| 5,295,967 A | 3/1994 | Rondelet et al. |
| 5,356,632 A | 10/1994 | Gross et al. |
| 5,425,706 A | 6/1995 | Gross et al. |
| 5,527,288 A | 6/1996 | Gross et al. |
| 5,704,520 A | 1/1998 | Gross |
| 5,800,420 A | 9/1998 | Gross et al. |
| 5,807,375 A | 9/1998 | Gross et al. |
| 5,820,622 A | 10/1998 | Gross et al. |
| 5,848,990 A | 12/1998 | Cirelli et al. |
| 5,848,991 A | 12/1998 | Gross et al. |
| 5,851,549 A | 12/1998 | Svec |
| 5,858,001 A | 1/1999 | Tsals et al. |
| 5,871,125 A | 2/1999 | Gross |
| 5,951,523 A | 9/1999 | Osterlind et al. |
| 5,957,889 A | 9/1999 | Poulsen et al. |
| 5,984,894 A | 11/1999 | Poulsen et al. |
| 5,997,501 A | 12/1999 | Gross et al. |
| 6,003,736 A | 12/1999 | Ljunggren |
| 6,033,377 A | 3/2000 | Rasmussen et al. |
| 6,033,421 A * | 3/2000 | Theiss et al. ................ 606/186 |
| 6,099,504 A | 8/2000 | Gross et al. |
| 6,186,982 B1 * | 2/2001 | Gross et al. ................ 604/132 |
| 6,261,272 B1 | 7/2001 | Gross et al. |
| 6,275,717 B1 | 8/2001 | Gross et al. |
| 6,312,409 B1 | 11/2001 | Gross |
| 6,314,317 B1 | 11/2001 | Willis |
| 6,346,095 B1 | 2/2002 | Gross et al. |
| 6,364,865 B1 | 4/2002 | Lavi et al. |
| 6,406,455 B1 | 6/2002 | Willis et al. |
| 6,440,096 B1 | 8/2002 | Lastovich et al. |
| 6,474,219 B2 | 11/2002 | Klitmose et al. |
| 6,478,771 B1 | 11/2002 | Lavi et al. |
| 6,485,461 B1 | 11/2002 | Mason et al. |
| 6,490,483 B2 | 12/2002 | Willis |
| 6,508,788 B2 | 1/2003 | Preuthun |
| 6,537,251 B2 | 3/2003 | Klitmose |
| 6,585,707 B2 | 7/2003 | Cabiri et al. |
| 6,589,229 B1 | 7/2003 | Connelly et al. |
| 6,595,956 B1 | 7/2003 | Gross et al. |
| 6,607,509 B2 | 8/2003 | Bobroff et al. |
| 6,607,513 B1 | 8/2003 | Down et al. |
| 6,613,019 B2 | 9/2003 | Munk |
| 6,616,627 B2 | 9/2003 | Willis et al. |
| 6,620,140 B1 | 9/2003 | Metzger |
| 6,641,565 B1 | 11/2003 | Lavi et al. |
| 6,645,181 B1 | 11/2003 | Lavi et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,689,100 B2 | 2/2004 | Connelly et al. |
| 6,692,457 B2 | 2/2004 | Flaherty |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,723,068 B2 | 4/2004 | Lavi et al. |
| 6,723,072 B2 | 4/2004 | Flaherty et al. |
| 6,740,059 B2 | 5/2004 | Flaherty |
| 6,749,587 B2 | 6/2004 | Flaherty |
| 6,767,188 B2 | 7/2004 | Vrane et al. |
| 6,768,425 B2 | 7/2004 | Flaherty et al. |
| 6,786,246 B2 | 9/2004 | Ohms et al. |
| 6,808,506 B2 | 10/2004 | Lastovich et al. |
| 6,830,558 B2 | 12/2004 | Flaherty et al. |
| 6,830,560 B1 | 12/2004 | Gross et al. |
| 6,899,699 B2 | 5/2005 | Enggaard |
| 6,936,006 B2 | 8/2005 | Sabra |
| 6,939,324 B2 | 9/2005 | Gonnelli et al. |
| 6,948,918 B2 | 9/2005 | Hansen |
| 6,952,604 B2 | 10/2005 | DeNuzzio et al. |
| 6,960,184 B2 | 11/2005 | Willis et al. |
| 6,960,192 B1 | 11/2005 | Flaherty et al. |
| 6,997,911 B2 | 2/2006 | Klitmose |
| 7,008,399 B2 | 3/2006 | Larsen et al. |
| 7,018,360 B2 | 3/2006 | Flaherty et al. |
| 7,027,478 B2 | 4/2006 | Ackley |
| 7,029,455 B2 | 4/2006 | Flaherty |
| 7,083,592 B2 | 8/2006 | Lastovich et al. |
| 7,083,599 B2 | 8/2006 | Alchas et al. |
| 7,115,108 B2 | 10/2006 | Wilkinson et al. |
| 7,128,727 B2 | 10/2006 | Flaherty et al. |
| 7,133,329 B2 | 11/2006 | Skyggebjerg et al. |
| 7,137,964 B2 | 11/2006 | Flaherty |
| 7,144,384 B2 | 12/2006 | Gorman et al. |
| 7,150,409 B2 | 12/2006 | Gonnelli et al. |
| 7,156,838 B2 | 1/2007 | Gabel et al. |
| 7,187,969 B2 | 3/2007 | Willis |
| 2002/0040208 A1 | 4/2002 | Flaherty et al. |
| 2002/0072733 A1 | 6/2002 | Flaherty |
| 2002/0123740 A1 | 9/2002 | Flaherty et al. |
| 2002/0126036 A1 | 9/2002 | Flaherty et al. |
| 2002/0169439 A1 | 11/2002 | Flaherty |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0130619 A1 | 7/2003 | Safabash et al. |
| 2003/0167035 A1 | 9/2003 | Flaherty et al. |
| 2003/0167036 A1 | 9/2003 | Flaherty |
| 2003/0199824 A1 | 10/2003 | Mahoney et al. |
| 2003/0199825 A1 | 10/2003 | Flaherty |
| 2003/0229310 A1 | 12/2003 | Flaherty et al. |
| 2004/0010207 A1 | 1/2004 | Flaherty et al. |
| 2004/0015131 A1 | 1/2004 | Flaherty et al. |
| 2004/0064088 A1 | 4/2004 | Gorman et al. |
| 2004/0064096 A1 | 4/2004 | Flaherty et al. |
| 2004/0069044 A1 * | 4/2004 | Lavi et al. ................ 73/1.73 |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0116866 A1 | 6/2004 | Gorman et al. |
| 2004/0158207 A1 * | 8/2004 | Hunn et al. ............ 604/164.01 |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0022274 A1 | 1/2005 | Campbell et al. |
| 2005/0049553 A1 | 3/2005 | Triplett et al. |
| 2005/0065472 A1 | 3/2005 | Cindrich et al. |
| 2006/0142698 A1 | 6/2006 | Ethelfeld |
| 2006/0264835 A1 | 11/2006 | Nielsen et al. |
| 2007/0093754 A1 | 4/2007 | Mogensen et al. |
| 2008/0027384 A1 | 1/2008 | Wang et al. |

| | | | |
|---|---|---|---|
| 2008/0167578 A1 | 7/2008 | Bryer et al. | |
| 2008/0215006 A1* | 9/2008 | Thorkild | 604/151 |
| 2008/0215035 A1 | 9/2008 | Yodfat et al. | |

FOREIGN PATENT DOCUMENTS

| | | |
|---|---|---|
| EP | 1 423 079 | 7/2006 |
| EP | 1 135 056 | 8/2006 |
| EP | 1 702 635 | 9/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 0 944 648 | 3/2007 |
| EP | 1 646 412 | 3/2007 |
| EP | 1 095 668 | 4/2007 |
| GB | 685178 | 12/1952 |
| WO | WO 99/48546 | 9/1999 |
| WO | WO 01/76684 A1 | 10/2001 |
| WO | WO 02/20073 A2 | 3/2002 |
| WO | WO 02/28454 A2 | 4/2002 |
| WO | WO 02/40083 A2 | 5/2002 |
| WO | WO 02/40083 A2 | 5/2002 |
| WO | WO 02/49509 A2 | 6/2002 |
| WO | WO 02/068015 A2 | 9/2002 |
| WO | WO 03/024504 A2 | 3/2003 |
| WO | WO 03/033051 A1 | 4/2003 |
| WO | WO 03/059372 A2 | 7/2003 |
| WO | WO 03/059372 A3 | 7/2003 |
| WO | WO 03/074121 A1 | 9/2003 |
| WO | WO 03/090509 A2 | 11/2003 |
| WO | WO 03/090819 A2 | 11/2003 |
| WO | WO 03/090838 A1 | 11/2003 |
| WO | WO 03/103758 A1 | 12/2003 |
| WO | WO 03/103763 A1 | 12/2003 |
| WO | WO 2004/006981 A2 | 1/2004 |
| WO | WO 2004/006982 A2 | 1/2004 |
| WO | WO 2004/030716 A2 | 4/2004 |
| WO | WO 2004/030717 A2 | 4/2004 |
| WO | WO 2004/030726 A1 | 4/2004 |
| WO | WO 2004/060436 A2 | 7/2004 |
| WO | WO 2004/093648 A2 | 11/2004 |
| WO | WO 2004/098390 A2 | 11/2004 |
| WO | WO 2004/098454 A2 | 11/2004 |
| WO | WO 2004/098683 A1 | 11/2004 |
| WO | WO 2004/098684 A2 | 11/2004 |
| WO | WO 2004098684 A2 * | 11/2004 |
| WO | WO 2005/000382 A2 | 1/2005 |
| WO | WO 2006/015922 A1 | 2/2006 |
| WO | WO 2006/018425 A2 | 2/2006 |
| WO | WO 2006/018425 A3 | 2/2006 |
| WO | WO 2006/018447 A2 | 2/2006 |
| WO | WO 2006/018447 A3 | 2/2006 |
| WO | WO 2006/024671 A1 | 3/2006 |
| WO | WO 2006/024672 A1 | 3/2006 |
| WO | WO-2006/032689 | 3/2006 |
| WO | WO 2006/032689 A1 | 3/2006 |
| WO | WO 2006/042811 A2 | 4/2006 |
| WO | WO 2006/042811 A3 | 4/2006 |
| WO | WO 2006/061354 A1 | 6/2006 |
| WO | WO 2006/072416 A2 | 7/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/084464 A1 | 8/2006 |
| WO | WO 2006/086980 A1 | 8/2006 |
| WO | WO 2006/089547 A1 | 8/2006 |
| WO | WO 2006/089548 A1 | 8/2006 |
| WO | WO 2006/089965 A1 | 8/2006 |
| WO | WO 2006/096746 A1 | 9/2006 |
| WO | WO 2006/097453 A1 | 9/2006 |
| WO | WO 2006/104806 A2 | 10/2006 |
| WO | WO 2006/108775 A2 | 10/2006 |
| WO | WO 2006/108809 A1 | 10/2006 |
| WO | WO 2006/116997 A1 | 11/2006 |
| WO | WO 2006/120253 A2 | 11/2006 |
| WO | WO 2006/125692 A1 | 11/2006 |
| WO | WO 2007/000425 A2 | 1/2007 |
| WO | WO 2007/000426 A2 | 1/2007 |
| WO | WO 2007/000427 A1 | 1/2007 |
| WO | WO 2007/052277 A1 | 5/2007 |

OTHER PUBLICATIONS

International Search Report dated Mar. 17, 2008 for PCT application PCT/US2007/076469.
Office Action dated Jun. 11, 2009 from related U.S. Appl. No. 11/645,972.
Notice of Allowance for U.S. Appl. No. 11/645,435 dated Jul. 24, 2008.
US Office Action for U.S. Appl. No. 11/645,972 dated Oct. 31, 2008.
US Office Action for U.S. Appl. No. 11/645,435 dated Oct. 30, 2007.
US Office Action for U.S. Appl. No. 11/645,972 dated Jun. 11, 2009.
US Office Action for U.S. Appl. No. 11/646,052 dated Jan. 27, 2009.
US Office Action for U.S. Appl. No. 11/646,052 dated Sep. 17, 2009.
US Office Action for U.S. Appl. No. 11/645,435 dated Apr. 23, 2008.
Notice of Allowance for U.S. Appl. No. 11/645,972 dated Jan. 11, 2010.
Notice of Allowance for U.S. Appl. No. 11/646,052 dated Jan. 28, 2010.
Office action for U.S. Appl. No. 12/277,186 dated Mar. 11, 2010.
Requirement for Restriction for U.S. Appl. No. 12/277,186 dated Sep. 30, 2009.
Supplemental Notice of Allowance for U.S. Appl. No. 11/646,052 dated Mar. 24, 2010.

* cited by examiner

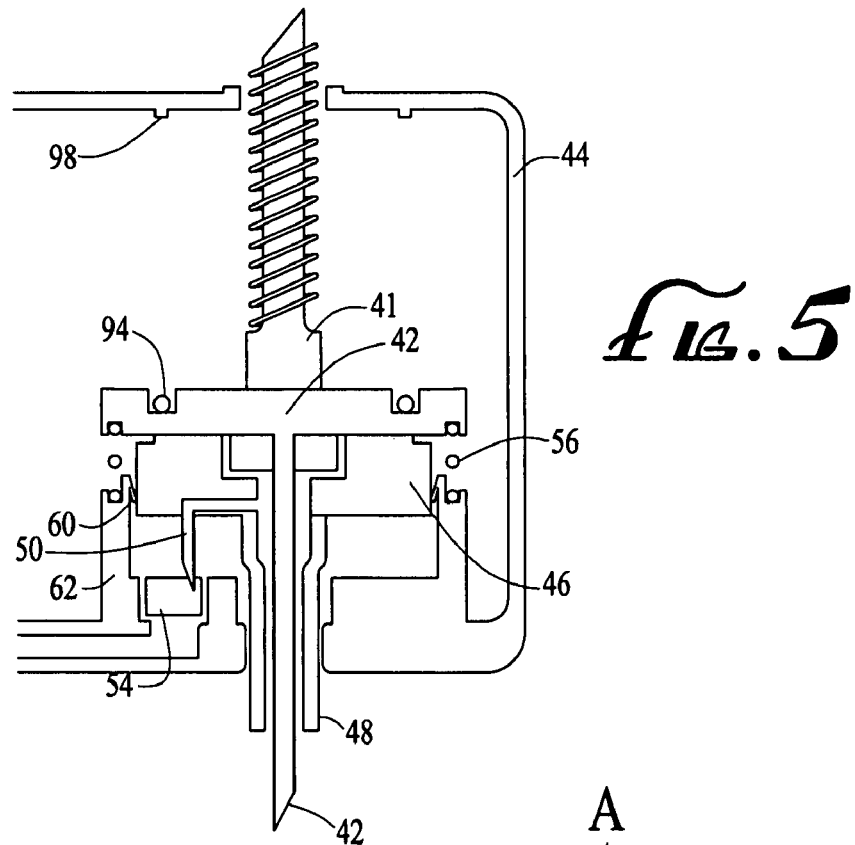
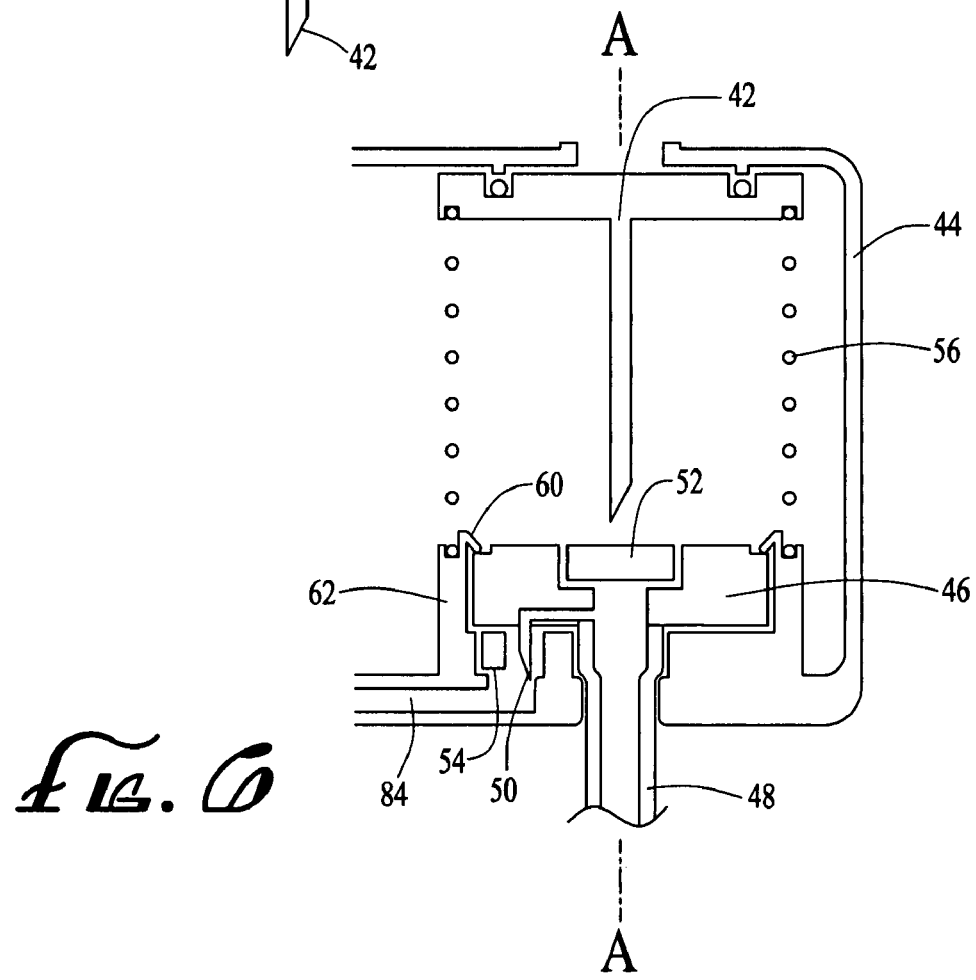

INFUSION MEDIUM DELIVERY SYSTEM, DEVICE AND METHOD WITH NEEDLE INSERTER AND NEEDLE INSERTER DEVICE AND METHOD

CROSS-REFERENCE TO RELATED PATENT APPLICATIONS

The present invention relates to U.S. Provisional Patent Application 60/839,840, filed Aug. 23, 2006 and U.S. Provisional Patent Application 60/854,829, filed Oct. 27, 2006, each of which is incorporated herein in its entirety and forms a basis for a claim of priority. The present invention also relates to U.S. Patent Application 60/678,290, filed May 6, 2005 and U.S. patent application Ser. No. 11/211,095, filed Aug. 23, 2005, titled "Infusion Device And Method With Disposable Portion," each of which is incorporated herein by reference in its entirety. The present invention further relates to co-pending application No. 60/839,822, filed Aug. 23, 2006, entitled "Infusion Medium Delivery Device And Method For Driving Plunger In Reservoir"; co-pending application No. 60/839,832, filed Aug. 23, 2006, titled "Infusion Medium Delivery Device And Method With Compressible Or Curved Reservoir Or Conduit"; co-pending application No. 60/839,741, filed Aug. 23, 2006, titled "Infusion Pumps And Methods And Delivery Devices And Methods With Same"; and co-pending application No. 60/839,821, filed Aug. 23, 2006, titled "Systems And Methods Allowing For Reservoir Filling And Infusion Medium Delivery", the contents of each of which is incorporated herein by reference, in its entirety. Embodiments of the present invention also relate to: (i) U.S. patent application Ser. No. 11/588,832, filed Oct. 27, 2006, entitled "Infusion Medium Delivery Device and Method with Drive Device for Driving Plunger in Reservoir"; (ii) U.S. patent application Ser. No. 11/588,847, filed Oct. 27, 2006, entitled "Infusion Medium Delivery Device and Method with Compressible or Curved Reservoir or Conduit"; (iii) U.S. patent application Ser. No. 11/588,875, filed Oct. 27, 2006, entitled "Systems And Methods Allowing For Reservoir Filling And Infusion Medium Delivery"; and (iv) U.S. patent application Ser. No. 11/589,323, filed Aug. 23, 2006, entitled "Infusion Pumps and Methods and Delivery Devices and Methods with Same"; (v) U.S. patent application Ser. No. Unassigned, filed Nov. 20, 2006, entitled "Systems and Methods Allowing for Reservoir filling and Infusion Medium Delivery"; (vi) U.S. patent application Ser. No. Unassigned, filed Nov. 20, 2006, entitled "Systems and Methods Allowing for Reservoir filling and Infusion Medium Delivery"; (vii) U.S. patent application Ser. No. Unassigned, filed Nov. 20, 2006, entitled "Systems and Methods Allowing for Reservoir filling and Infusion Medium Delivery"; (viii) U.S. patent application Ser. No. Unassigned, filed Nov. 20, 2006, entitled "Systems and Methods Allowing for Reservoir filling and Infusion Medium Delivery"; (ix) U.S. patent application Ser. No. Unassigned, filed Nov. 22, 2006, entitled "Infusion Medium Delivery Device and Method and Drive Device for Driving Plunger in Reservoir"; (x) U.S. patent application Ser. No. Unassigned, filed Nov. 22, 2006, entitled "Infusion Medium Delivery. Device and Method and Drive Device for Driving Plunger in Reservoir", the contents of each of which are incorporated by reference herein, in their entirety.

FIELD OF THE INVENTION

Embodiments of the present invention relate to an infusion medium delivery system, device and method for delivering an infusion medium to a patient-user, including a needle inserter device and method for inserting a needle and/or cannula into a patient-user for conveying the infusion medium to the patient-user. Further embodiments relate to the needle inserter device and method, whether or not included in an infusion medium delivery system, device or method. According to some embodiments as described herein, the delivery device may include a disposable portion and a durable portion connectable to the disposable portion, and wherein the base portion can be separated from the durable portion and disposed of after one or more specified number of uses. The disposable portion supports a reservoir, while the durable portion supports a drive device for selectively driving the infusion medium out of the reservoir and into the needle and/or cannula.

BACKGROUND OF THE INVENTION

Certain chronic diseases may be treated, according to modern medical techniques, by delivering a medication or other substance to a patient-user's body, either in a continuous manner or at particular times or time intervals within an overall time period. For example, diabetes is a chronic disease that is commonly treated by delivering defined amounts of insulin to the patient-user at appropriate times. Some common modes of providing an insulin therapy to a patient-user include delivery of insulin through manually operated syringes and insulin pens. Other modern systems employ programmable pumps to deliver controlled amounts of insulin to a patient-user.

Pump type delivery devices have been configured in external devices (that connect to a patient-user) or implantable devices (to be implanted inside of a patient-user's body). External pump type delivery devices include devices designed for use in a generally stationary location (for example, in a hospital or clinic), and further devices configured for ambulatory or portable use (to be carried by a patient-user). Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a patient-user, for example, through a suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces the patient-user's skin, a manual insertion of the needle into the patient-user can be somewhat traumatic to the patient-user. Accordingly, insertion mechanisms have been made to assist the insertion of a needle into the patient-user, whereby a needle is forced by a spring to quickly move from a retracted position into an extended position. Examples of insertion mechanisms that are built into a delivery device are described in U.S. patent application Ser. No. 11/211,095, filed Aug. 23, 2005, titled "Infusion Device And Method With Disposable Portion" (assigned to the assignee of the present invention), which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety. As the needle is moved into the extended position, the needle is quickly forced through the patient-user's skin in a single, relatively abrupt motion that can be less traumatic to certain patient-users as compared to a slower, manual insertion of a needle. While a quick thrust of the needle into the patient-user's skin may be less traumatic to some patient's than a manual insertion, it is believed that, in some contexts, some patients may feel less trauma if the needle is moved a very slow, steady pace.

As compared to syringes and insulin pens, pump type delivery devices can be significantly more convenient to a patient-user, in that accurate doses of insulin may be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and doctors and patient-users become more familiar with such devices, the popularity of external medical infusion pump treatment increases and is expected to increase substantially over the next decade.

BRIEF DESCRIPTION OF THE DRAWINGS

FIG. 5 is a schematic, cross-sectional view of the needle inserter device of FIG. 4, wherein the needle and cannula are each in a partially extended position.

FIG. 6 is a schematic, cross-sectional view of the needle inserter device of FIG. 4, wherein the cannula is in a fully extended position and the needle is in a retracted position.

DETAILED DESCRIPTION

Figure 1:
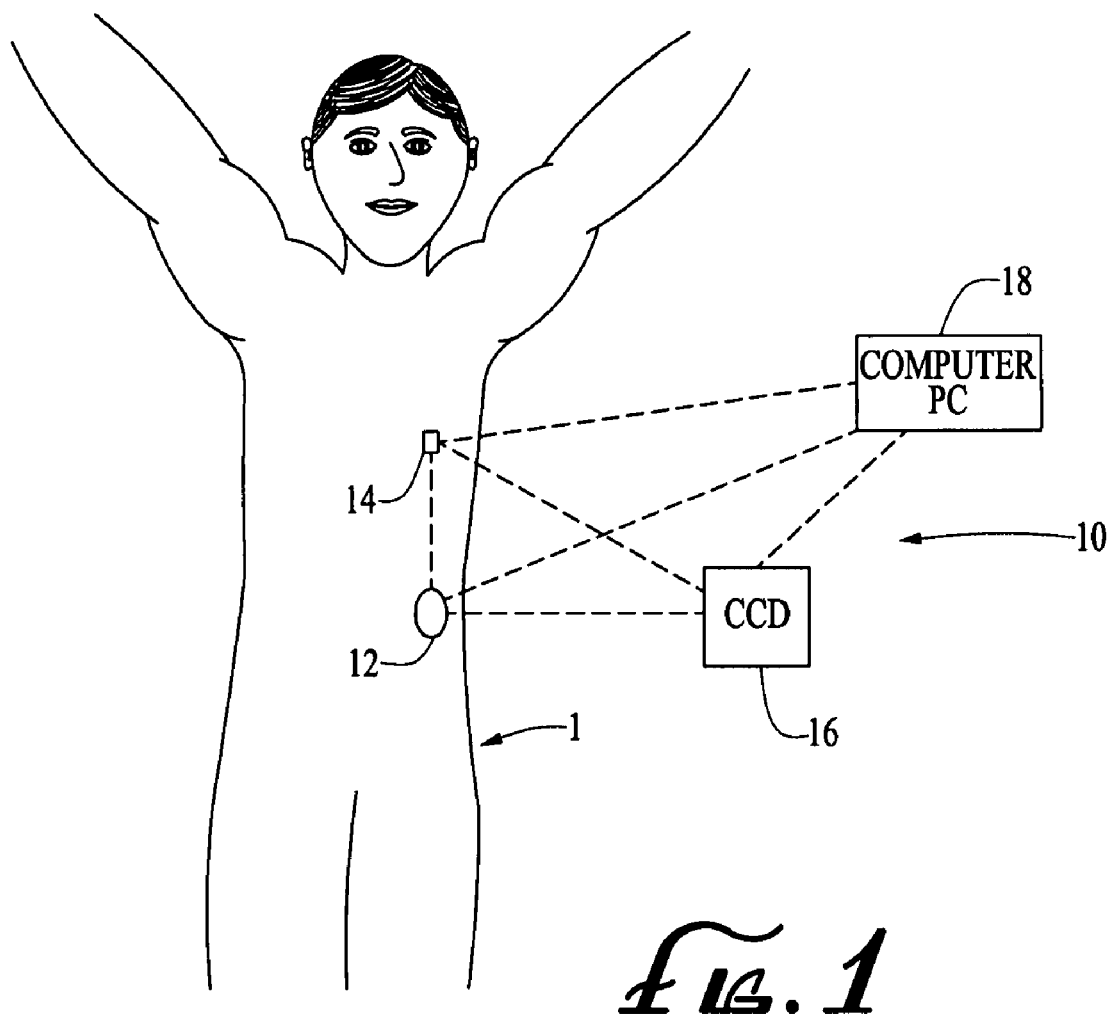
FIG. 1 is a generalized diagram of a delivery system in relation to a human patient-user.

The present invention relates, generally, to needle inserter devices and methods and delivery systems, devices and methods that include such needle inserter devices and methods, for delivering an infusion medium to a recipient, such as a medical patient. The needle inserter device and method may operate to insert a hollow needle or cannula through a patient-user's skin, to provide a fluid flow path for conveying an infusion medium through the hollow needle or cannula and into the patient-user. Embodiments of the present invention may be configured, as described herein, to provide a reliable, cost effective and easy-to-use mechanism for inserting a hollow needle or cannula to a specific depth into a patient-user with minimal traumatic effect.

In addition, embodiments may be configured to establish a contiguous fluid-flow passage for fluid transfer between a reservoir and the patient-user, when the hollow needle or cannula is inserted into the patient-user. Needle inserter devices according to embodiments of the present invention may be incorporated in a delivery device and share a portion of the delivery device housing with other components of the delivery device. In other embodiments, needle inserter devices and methods described herein may be employed in housing structures located external to a delivery device and connected to the delivery device, for example, through a fluid-flow conduit.

In particular embodiments, a delivery device includes first and second housing portions (referred to herein as a durable housing portion and a disposable housing portion, respectively) that are configured to engage and attach to each other for operation. The disposable housing portion may contain or otherwise support a needle inserter device, an infusion medium reservoir and other components that come into contact with the infusion medium and/or the patient-user during operation.

The disposable housing portion may be disengaged and separated from the durable housing portion, such that the disposable housing portion may be readily disposed of after it has been in use for a period of time, or after one or a prescribed number of uses. After disengagement and separation from a disposable housing portion, the durable housing portion may be engaged and operatively connected to another disposable housing portion (such as a new, user-filled, pre-filled, refurbished, refilled or re-manufactured disposable housing portion) for further operation. The durable housing portion may contain or otherwise support components that do not come into contact with the infusion medium or the patient-user during normal operation of the delivery device, including, but not limited to, a drive device, drive linkage, electronic circuits and, in some embodiments, a power source.

While embodiments of the present invention are described herein with reference to an insulin delivery example for treating diabetes, other embodiments of the invention may be employed for delivering other infusion media to a patient-user for other purposes. For example, further embodiments of the invention may be employed for delivering other types of drugs to treat diseases or medical conditions other than diabetes, including, but not limited to drugs for treating pain or certain types of cancers, pulmonary disorders or HIV. Further embodiments may be employed for delivering media other than drugs, including, but not limited to, nutritional media including nutritional supplements, dyes or other tracing media, saline or other hydration media, or the like. Also, while embodiments of the present invention are described herein for delivering or infusing an infusion medium to a patient-user, other embodiments may be configured to draw a medium from a patient-user.

Furthermore, while embodiments of the present invention refer to the housing portions of disclosed delivery devices as disposable or durable, and may be configured to allow the disposable housing portion to be disposed of and replaced in an economically efficient manner, it will be understood that, in further embodiments, the disposable housing portion embodiments described herein may be re-used and need not be disposed of. Similarly, the durable housing portion embodiments described herein may be disposed of after one or more uses, if desired. However, embodiments are configured to allow certain components (for example, those that contact the infusion medium or the patient-user during operation) to be housed in a first housing portion that may be readily disposable, while other components (for example, those that do not contact the infusion medium or the patient-user during operation and that have a replacement cost that is of a relatively significant level) may be housed in a second housing portion that may be re-used with one or more new, user-filled, prefilled, refilled, refurbished or remanufactured disposable first housing portions. Also, while delivery device embodiments of the present invention include multiple housing portions, such as a disposable housing portion and a durable housing portion, other delivery device embodiments may employ a single housing structure that includes, among other features, a needle inserter device as described below. Yet other embodiments may employ an injection site module that contains a needle injector device and that connects to a further housing (such as the disposable housing portion) of a delivery device, as described below.

A generalized representation of an infusion medium delivery system 10 is shown in FIG. 1, wherein the system includes a delivery device 12 configured according to an embodiment of the invention described herein. The system 10 may also include other components coupled for communication with the delivery device 12, including, but not limited to, a sensor or monitor 14, a command control device (CCD) 16 and a computer 18. Each of the CCD 16, the computer 18, the sensor or monitor 14 and the delivery device 12 may include receiver or transceiver electronics that allow communication with other components of the system. While the sensor or monitor 14 in FIG. 1 is shown as a separate element relative to the delivery device 12 and connected thereto through a communication link, in other embodiments, the sensor or monitor 14 may be incorporated within the delivery device 12. The delivery device 12 may include electronics and software for analyzing sensor data and for delivering an infusion medium according to sensed data and/or pre-programmed delivery routines. Some of the processing, delivery routine storage and control functions may be carried out by the CCD 16 and/or the computer 18, to allow the delivery device 12 to be made with more simplified electronics. However, in other embodiments, the system 10 may include delivery device 12 that operates without any one or more of the other components of the system 10 shown in FIG. 1. Examples of the types of communications and/or control capabilities, as well as device feature sets and/or program options may be found in U.S. patent application Ser. No. 10/445,477 filed May 27, 2003, and entitled "External Infusion Device with Remote Programming, Bolus Estimator and/or Vibration Alarm Capabilities," and U.S. patent application Ser. No. 10/429,385 filed May 5, 2003, and entitled "Handheld Personal Data Assistant (PDA) with a Medical Device and Method of Using the Same," U.S. patent application Ser. No. 09/813,660 filed Mar. 21, 2001, and entitled "Control Tabs For Infusion Devices And Methods Of Using The Same," all of which are incorporated herein by reference in their entirety.

In the generalized system diagram of FIG. 1, the delivery device 12 and sensor or monitor 14 are secured to a patient-user 1. The locations at which those components are secured to the patient-user 1 in FIG. 1 are provided only as a representative, non-limiting example. The delivery device 12 and sensor or monitor 14 may be secured at other locations on the patient-user 1 (including, but not limited to, other locations on the patient-user's skin, clothing, belt, suspenders, straps, purse or other carriable holder), and such locations may depend upon the type of treatment to be administered by the system 10.

As described in further detail below, the delivery device 12 includes a reservoir containing an infusion medium and delivers the infusion medium, such as, but not limited to an insulin formulation, into the patient-user's body in a controlled manner. Control instructions and/or data may be communicated between the delivery device 12, the sensor or monitor 14, the CCD 16 and the computer 18. The delivery device 12 may be configured to secure to the skin of a patient-user 1, in the manner of a patch, at a desired location on the patient-user. In such embodiments, it is desirable that the delivery device 12 have relatively small dimensions for comfort and ability to conceal the device, for example, under a garment.

Examples of patch-like delivery devices are described in U.S. patent application Ser. No. 11/211,095, filed Aug. 23, 2005, U.S. Patent Application No. 60/839,822, filed Aug. 23, 2006, titled "Infusion Medium Delivery Device And Method For Driving Plunger In Reservoir", U.S. Patent Application No. 60/839,832, filed Aug. 23, 2006, titled "Infusion Medium Delivery Device And Method With Compressible Or Curved Reservoir Or Conduit", and U.S. Patent Application No. 60/839,741, filed Aug. 23, 2006, titled "Infusion Pumps And Methods And Delivery Devices And Methods With Same", each of which is incorporated herein, in its entirety. A delivery device according to embodiments of the present invention may be configured in accordance with any one of the delivery devices described in the above-referenced patent applications, and further includes a needle inserter device according to needle inserter embodiments described herein. A delivery device according to further embodiments of the present invention may be configured in accordance with other suitable delivery device designs, and further includes or is connected with a needle inserter device according to needle inserter embodiments described herein.

Figure 2:
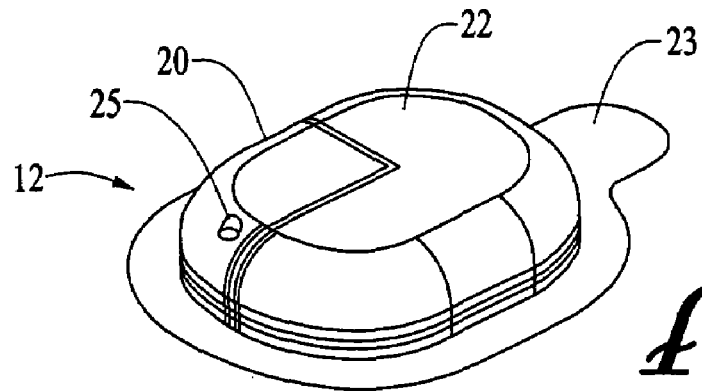
FIG. 2 is a perspective view of a delivery device according to an embodiment of the invention.

An example of a delivery device 12 according to an embodiment of the present invention is shown in FIG. 2. The delivery device 12 includes a base housing portion 20 that, in some embodiments, may be disposable after one or a number of specified uses, and a further housing portion 22. For convenience, but without limitation, the base portion 20 is referred to herein as a disposable housing portion or disposable portion, while the further housing portion 22 is referred to herein as a durable housing portion or durable portion. However, as noted above, in operation, either or both housing portions 20 or 22 may be disposed of or re-used, depending upon the context of use.

The disposable housing portion 20 may support structural elements that ordinarily contact the patient-user's skin or the infusion medium, during operation of the delivery device 12. On the other hand, the durable housing portion 22 may support elements (including electronics, motor components, linkage components, and the like) that do not ordinarily contact the patient-user or the infusion medium during operation of the delivery device 12. Thus, elements in the durable housing portion 22 of the delivery device 12 are typically not contaminated from contact with the patient-user or the infusion medium during normal operation of the delivery device 12.

Figure 3:
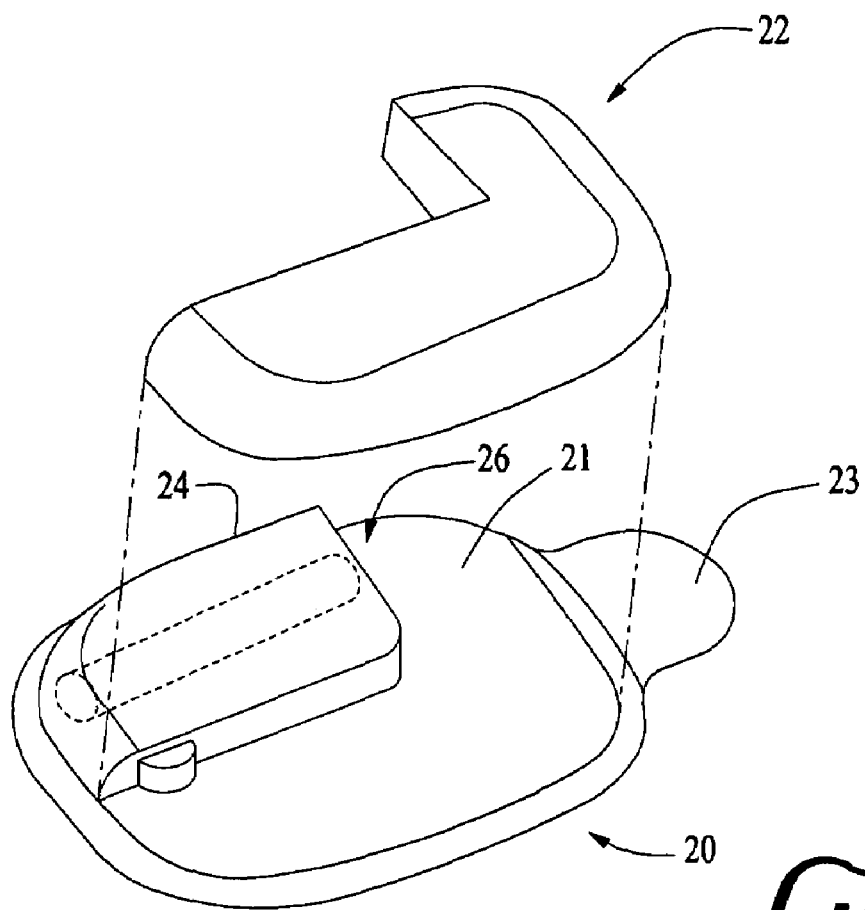
FIG. 3 is a perspective view of a durable portion and a disposable portion of the delivery device of FIG. 2, with the durable portion separated from the disposable portion.

In the illustrated embodiment, the disposable housing portion 20 of the delivery device 12 includes a base 21 that includes or otherwise supports a reservoir retaining portion 24 that houses a reservoir. The durable housing portion 22 may include a housing that secures onto the base 21 adjacent the reservoir retaining portion 24, and may be selectively removed from the base 21, as shown in FIG. 3. The durable housing portion 22 may house a suitable drive device, such as an electrically operated motor (not shown in FIG. 2), and drive linkage components (not shown in FIG. 2) for driving fluid out of the reservoir. The durable housing portion 22 also may house suitable control electronics (not shown in FIG. 2) for controlling the operation of the drive device to drive fluid from the reservoir in a controlled manner. Further embodiments may include other electronics within the durable housing portion 22, such as, but not limited to communication electronics (not shown in FIG. 2) for communicating with the sensor or monitor 14, the CCD 16, the computer 18 and/or other components of the system 10 shown in FIG. 1.

The base 21 of the disposable housing portion 20 has a bottom surface (facing downward and into the page in FIGS. 2 and 3) that is configured to secure to a patient-user's skin at a desired location on the patient-user. A suitable adhesive may be employed at the interface between the bottom surface of the base 21 and the patient-user's skin, to adhere the base 21 to the patient-user's skin. The adhesive may be provided on the bottom surface of the base 21, with a peelable cover layer 23 covering the adhesive material. In this manner, a patient-user may peel off the cover layer 23 to expose the adhesive material and then place the adhesive side of the base 21 against the patient-user's skin.

The disposable portion 20 may include a button or other operator 25 for operating a needle inserter device located within the reservoir retaining portion 24. Alternatively, or in addition, reference number 25 may represent an opening 25, through which an external plunger or another form of operator, may operate the needle inserter device, as described below. The operator or opening 25 may be provided in a location that is readily accessible from outside of the disposable housing portion 20, when the disposable housing portion 20 is secured to a patient-user's skin. For example, in the illustrated embodiment, the outer wall on which the operator or opening 25 is located is a top wall of the disposable housing portion, facing a direction substantially opposite to the facing direction of the bottom surface that has the adhesive layer and peelable cover layer 23. Alternatively, or in addition to an operator or opening 25, the needle inserter device may be activated, through a wireless link, from an external controller, such as the CCD 16, sensor or monitor 14 or computer 18. For such embodiments, the CCD 16, sensor or monitor 14 or computer 18 includes a wireless signal transmitter, while the delivery device includes a receiver for receiving a wireless actuation signal and an electronic actuator that is controlled to actuate the needle inserter device, upon receipt of an actuation signal from the CCD 16, sensor or monitor 14 or computer 18.

The durable housing portion 22 of the delivery device 12 includes a housing shell configured to mate with and secure to the disposable housing portion 20. The durable housing portion 22 and disposable housing portion 20 may be provided with correspondingly shaped grooves, notches, tabs or other suitable features that allow the two parts to easily snap together, by manually pressing the two portions together in a manner well known in the mechanical arts. In a similar manner, the durable housing portion 22 and disposable housing portion 20 may be separated from each other by manually applying sufficient force to unsnap the two parts from each other. In further embodiments, a suitable seal, such as an annular seal, may be placed along the peripheral edge of the disposable housing portion 20 and/or the durable housing portion 22, so as to provide a liquid, hermetic, or air-tight seal between the disposable housing portion 20 and the durable housing portion 22.

The durable housing portion 22 and disposable housing portion 20 may be made of suitably rigid materials that maintain their shape, yet provide sufficient flexibility and resilience to effectively snap together and apart, as described above. The base 21 material may be selected for suitable compatibility with the patient-user's skin. For example, the disposable housing portion 20 and the durable housing portion 22 of the delivery device 12 may be made of any suitable plastic, metal, composite material or the like. The disposable housing portion 20 may be made of the same type of material or a different material relative to the durable housing portion 22. The disposable and durable housing portions may be manufactured by injection molding or other molding processes, machining processes or combinations thereof.

The base 21 may be made of a relatively flexible material, such as a flexible silicone, plastic, rubber, synthetic rubber or the like. By forming the base 21 of a material capable of flexing with the patient-user's skin, a greater level of patient-user comfort may be achieved when the base is secured to the patient-user's skin. Also, a flexible base 21 can result in an increase in the site options on the patient-user's body at which the base 21 may be secured.

The disposable housing portion 20 and/or the durable housing portion 22 may include an internal sensor (not shown in FIGS. 2 and 3) for connection to a patient-user, for example, through a needle (not shown in FIGS. 2 and 3) or a set of micro-needles for piercing a patient-user's skin when the disposable housing portion 20 is secured to a patient-user's skin. In such embodiments, a suitable aperture (not shown in FIGS. 2 and 3) may be formed in the base 21, to allow the passage of the sensor needle or micro-needles, when the disposable portion is secured to the patient-user's skin. Alternatively, the durable housing portion 20 of the delivery device 12 may be connected to an external sensor 14, through a sensor lead, as described with respect to FIG. 2 of U.S. patent application Ser. No. 11/211,095, filed Aug. 23, 2005. The sensor may include any suitable biological sensing device, depending upon the nature of the treatment to be administered by the delivery device 12. For example, in the context of delivering insulin to a diabetes patient, the sensor 14 may include a blood glucose sensor. Alternatively, or in addition, one or more environmental sensing devices may be included in or on the delivery device 12, for sensing one or more environmental conditions. In further alternatives, the sensor may be included with as a part or along side the infusion cannula and/or needle, such as for example as shown in U.S. patent Ser. No. 11/149,119 filed Jun. 8, 2005, and entitled "Dual Insertion Set," which is incorporated herein by reference in its entirety.

As described above, by separating disposable elements of the delivery device 12 from durable elements, the disposable elements may be arranged on the disposable portion 20, while durable elements may be arranged within a separable durable portion 22. In this regard, after one (or a prescribed number) of uses of the delivery device 12, the disposable portion 20 may be separated from the durable portion 22, so that the disposable portion 20 may be disposed of in a proper manner. The durable portion 22 may, then, be mated with a new (un-used, user-filled, pre-filled, refurbished, re-filled or re-manufactured) disposable portion 20 for further delivery operation with a patient-user.

A reservoir 28 is located in the reservoir retaining portion 24 of the disposable housing portion 20. The reservoir 28 may include a container having an internal volume for containing a fluidic infusion medium, such as, but not limited to an insulin formulation. The reservoir 28 may be made of any material suitably compatible with the infusion medium, including, but not limited to suitable metal, plastic, ceramic, glass, composite material or the like. For example, the reservoir 28 may be formed of a plastic material referred to as TOPAS (trademark of Ticona, a subsidiary of Celanese Corporation), such as described in U.S. patent application Ser. No. 11/100,188, filed Apr. 5, 2005 (Publication No. 2005/0197626).

In yet other embodiments, the reservoir 28 may be formed unitarily with the reservoir retaining portion 24, for example, as a hollow chamber provided within an otherwise solid portion of the reservoir retaining portion 24. In such embodiments, the hollow interior of the reservoir retaining portion 24 may be coated or lined in another manner with a suitable metal, plastic, plastic TOPAS (trademark of Ticona, a subsidiary of Celanese Corporation), ceramic, glass, composite material or the like. Alternatively, or in addition, the retaining portion 24, itself, may be made of a suitable metal, plastic, plastic TOPAS (trademark of Ticona, a subsidiary of Celanese Corporation), ceramic, glass, composite material or the like.

The reservoir 28 has an outlet port (not shown), through which the infusion medium contained within the interior of the reservoir 28 may be communicated out of the reservoir. The outlet port is arranged in fluid flow communication with the interior of the reservoir 28 and is connected, through any suitable fluid-flow conduit, in fluid flow communication with an injection site. In the embodiment in FIGS. 2 and 3, the injection site is located within the disposable housing portion 20 and is accessible through the opening 25. In other embodiments as described below, the injection site may be located external to the disposable housing portion 20 and connected to the reservoir 28, through a fluid flow conduit in the form of a flexible tube. In yet other embodiments as described below, the injection site may be located on a base portion to which one or both of the disposable housing portion 20 and the durable housing portion 22 may connect.

The fluid flow conduit may include a fluid-flow path that has a first end in fluid flow communication with the outlet port of the reservoir and a second end in fluid flow communication with the injection site. The injection site may include a needle inserter device as described herein, to assist the insertion of a needle or cannula into the patient-user and connection of the needle or cannula in flow communication with the fluid flow conduit.

Figure 4:
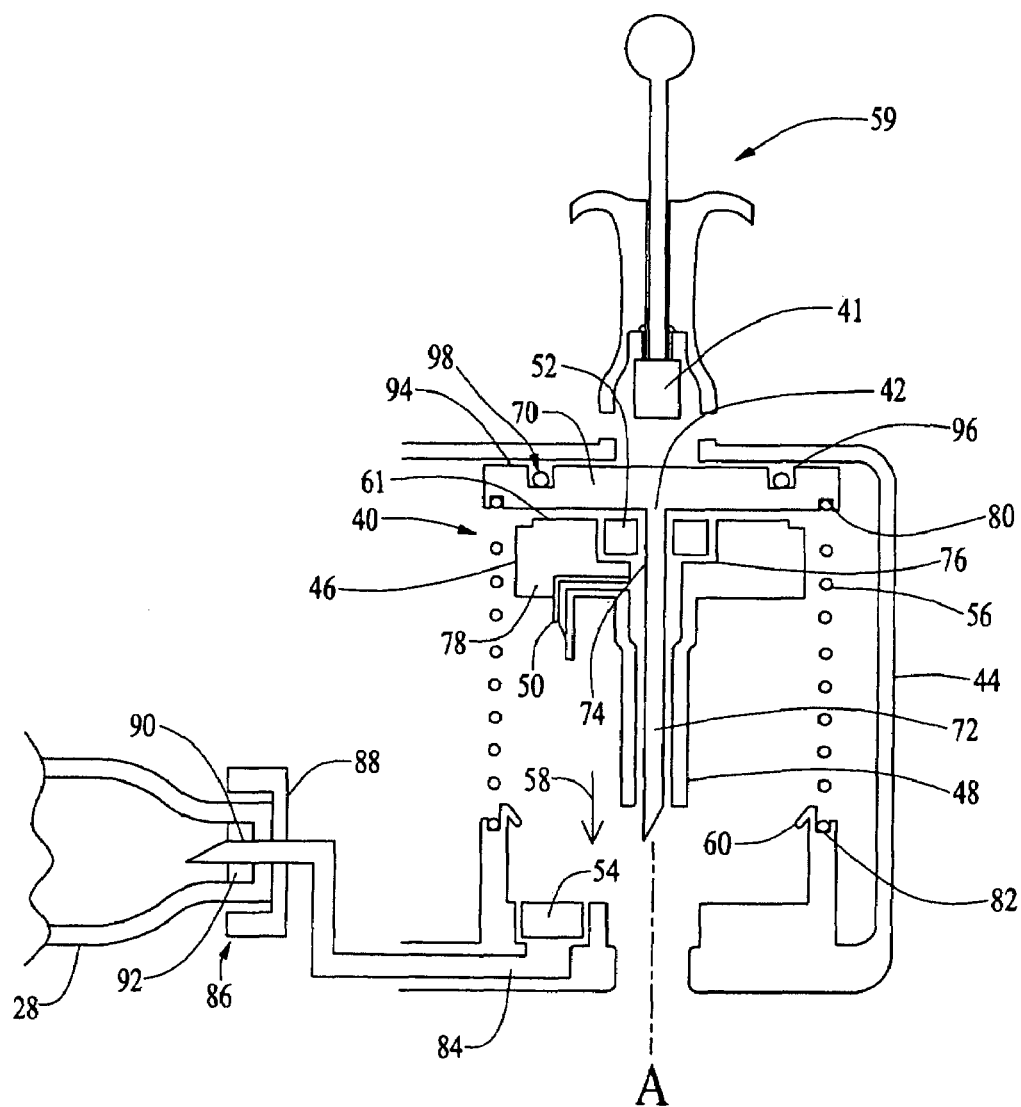
FIG. 4 is a schematic, cross-sectional view of a needle inserter device within the delivery device of FIGS. 2 and 3, according to an embodiment of the invention, wherein a needle and a cannula are each in a retracted position.

An example of a needle inserter device 40 according to an embodiment of the present invention is shown in FIGS. 4-6. The needle inserter device 40 of FIGS. 4-6 operates with an external plunger device 41, described below. The needle inserter device 40 includes a moveable needle 42 supported within a housing structure 44. In the illustrated embodiment, the housing structure 44 may include a portion of the housing structure of the disposable housing portion 20 of FIGS. 2 and 3. In other embodiments, the housing structure 44 may include the housing structure of another suitable drive device housing or a housing structure that is separate from a drive device housing.

In addition to the moveable needle 42, the needle inserter device 40 further includes a needle carriage 46, a hollow needle or cannula 48, a further hollow needle 50, a first septum 52, a second septum 54 and a bias member 56. The moveable needle 42, needle carriage 46 and cannula 48 are supported for movement within the housing 44, from a retracted position shown in FIG. 4, to an extended position in the direction of arrow 58, along the axial direction A of the needle 42 and cannula 48. In the view of FIG. 5, the moveable needle 42, needle carriage 46 and cannula 48 are in a partially extended position. In the view of FIG. 6, the moveable needle carriage 46 and cannula 48 are in a fully extended position, while the moveable needle 42 has been returned to the retracted position. As described below, the needle inserter device 40 operates with an external plunger device 59, configured to apply a force along the axis A of the moveable needle 42 and cannula 48, in the direction of arrow 58, to move the moveable needle 50, needle carriage 46 and cannula 48 in the direction of arrow 58.

The needle carriage 46 is configured to engage one or more (two shown in FIGS. 4-6) engagement pawls 60 connected to the housing 44, as the needle carriage 46 moves into the extended position. Upon the needle carriage 46 reaching a fully extended position, each of the engagement pawls 60 engage a surface 61 of the needle carriage 46. In the illustrated embodiment, the pawls 60 include a pair of protruding arms extending inward toward the axis A from a corresponding pair of struts 62 that extend into the interior of the housing 44, from a bottom wall (relative to the orientation of FIGS. 4-6) of the housing 44. In a further embodiment, a single, annular strut 62 may extend around the circumference of the needle carriage 46 to support a single annular pawl 60 or multiple pawls 60 around the circumference of the needle carriage 46.

The struts 62 and pawls 60 may be configured unitary with the housing 44, such as by forming the unitary structure in a mold and/or machined or otherwise formed from a unitary piece of material. In such an embodiment the pawls may be provided with sufficient flexibility to allow them to flex downward, toward the struts 62 (as shown in FIG. 5) by the force of the needle carriage 46, as the needle carriage 46 is moved toward the extended position, and sufficient resilience to return to an unflexed position, upon the needle carriage 46 reaching a position along the direction of motion 58 at which the engagement surface 62 passes the pawls 60, as shown in FIG. 6. Alternatively or in addition, the struts 62 may be provided with sufficient pivotal flexibility and resilience to flex or pivot outward (away from the axis A) and allow the needle carriage 46 to sufficiently pass the pawls 60, whereupon the struts 62 are allowed to flex or pivot back toward their unflexed or non-pivoted position. When the struts 62 and/or pawls 60 are allowed to flex back toward an unflexed state, the pawls 60 engage the engagement surface 62 of the needle carriage 46, to hold the needle carriage 46 in place, as the needle 42 is returned to a retracted position, also as shown in FIG. 6.

In further embodiments, the pawls 60 may be formed as separate members relative to the struts 62, and may be connected to the struts 62 in a manner that allows the pawls 60 to flex and/or pivot downward, similar to the downward flex of the pawls 60 shown in FIG. 5, for example, through a suitable pivotal or flexible connection structure. A bias spring may be provided within the connection structure to bias the pawls 60 toward their unflexed (or non-pivoted) position of FIG. 4. Also in further embodiments, the struts 62 may be formed as separate structural elements relative to the housing 44 and may be connected in a fixed relation to the housing 44 by any suitable connection structure. The housing 44, struts 62 and pawls 60 may be formed of any suitable material having sufficient rigidity and flexibility to perform the functions described herein, such as a plastic, metal, composite material or the like, as described above with respect to the disposable housing portion 20.

The moveable needle 42 includes a needle head 70 and a needle shaft 72. The needle head 70 and needle shaft 72 may be formed as a unitary structure or as separate structures connected in a fixed relation to each other. In one example embodiment, the needle head 70 includes a round, disk-shaped structure, while the needle shaft 72 includes a cylindrical structure extending from a central axis of the round, disk-shaped head and having a pointed tip for piercing a patient-user's skin. The needle 42 may be made of any suitable material having sufficient rigidity and biocompatibility to function to pierce a patient-user's skin and operate with other components as described herein, such as, but not limited to NiTi, other metal, plastic, ceramic, composite materials or the like.

The needle carriage 46 is arranged adjacent (and below, in the orientation of FIGS. 4-6) the needle head 70. The needle carriage 46 may include a generally disk-shaped body having a central passage 74 along its axial dimension, through which the needle shaft 72 may extend. The first septum 52 is arranged to cover one end of the central passage 74. In the illustrated embodiment, the disk-shaped body of the needle carriage 46 has a recess 76 for containing at least a portion of the first septum 52, where the recess is located on a surface of the disk-shaped body that faces the needle head. The first septum 52 is retained within the recess 76 and secured in a fixed relation relative to the needle carriage 46, to allow the needle shaft 72 to pierce the first septum (when the needle 42 and needle carriage 46 are in the position shown in FIGS. 4 and 5), and also allow the needle shaft 72 to be withdrawn from the first septum 52, when the needle 42 is returned to the retracted position (as shown in FIG. 6). For example, the first septum 52 may be retained within the recess 76 by frictional engagement, adhesive, thermal coupling or other suitable connection structure.

The needle carriage 46 includes a fluid flow passage 78 in fluid flow communication with the central passage 74. The further hollow needle 50 has a hollow fluid flow path connected in fluid flow communication with the passage 78. The hollow needle 50 extends from the needle carriage 46 (downward in the orientation of FIGS. 4-6), in a direction generally parallel to the axis A of the needle 42 and cannula 48, but spaced to one side of the axis A. The hollow needle 50 has a sharp tip that is directed toward the second septum 54 and positioned to pierce the second septum 54, as the needle carriage 46 is moved toward the extended position, as shown in FIGS. 5 and 6.

The cannula or hollow needle 48 may include a hollow, cylindrical tube-shaped structure. For patient comfort, the outside diameter of the cannula 48 may be as small as possible, so that the cannula can be placed through the patient-user's skin, with minimal traumatic effect on the patient-user. The inside diameter of the hollow tube-shaped structure of the cannula 48 is larger than the outer diameter of the needle shaft 72, to allow the needle shaft 72 to extend through the cannula 48, when the needle 42, needle carriage 46 and cannula 48 are in the retracted position, as shown in FIG. 4, yet allow the needle to be withdrawn from at least a portion of the cannula 48, as described below.

The length of the cannula 48 along the axial direction A, is selected to be long enough to extend through a patient-user's skin and to a desired location within the patient-user for delivering the infusion medium, when the cannula is in the extended position, as shown in FIG. 6, yet be short enough (relative to the length of the needle shaft 72, to allow the sharp end of the needle shaft 72 to extend out from the end of the cannula, when the needle 42, needle carriage 46 and cannula 48 are in the retracted position, as shown in FIG. 4. The cannula 48 may be made of any suitable material having sufficient rigidity and biocompatibility to function as described herein, such as, but not limited to metal, plastic, ceramic, composite materials or the like.

One end of the cannula 48 has a flared (enlarged diameter) end that is arranged to remain external to the patient-user, when the cannula is in the extended position as shown in FIG. 6. The flared end of the cannula 48 is secured to the needle carriage 46, with the hollow interior of the cannula 48 arranged in fluid flow communication with the central passage 74 of the needle carriage 46. The flared end of the cannula 48 may be secured to the needle carriage 46, by any suitable connection structure, including, but not limited to, a friction fit with a funnel-shaped extension of the needle carriage, adhesive, thermal coupling or the like. In further embodiments, the flared shape of the end of the cannula 48 may be omitted and the cannula 48 may have a constant outer diameter along its entire length.

The bias member 56 is configured to apply a bias force on the needle 42, in the direction opposite to the direction of arrow 58. The bias member 56 may include any suitable structure that provides a bias force on the needle 42, including, but not limited to, a spring configuration, a permanent magnet, an electromagnet or the like. In the example embodiment of FIGS. 4-6, the bias member 56 includes a coil spring, which is configured to be compressed into a compressed state as shown in FIG. 5 and, when released, to expand to the expanded state shown in each of FIGS. 4 and 6, when no external force is applied on the needle inserter device. In particular, the coil spring bias member 56 may compress to and beyond the state shown in FIG. 5 to allow each of the pawls 60 to engage an engagement surface 62 of the needle carriage 46, when a sufficient external force is applied to the needle inserter device by the plunger device 41 in the direction of arrow 58. The coil spring may be made of any suitable spring material, including, but not limited to, metal, plastic, composite material or the like.

In the embodiment of FIGS. 4-6, the coil spring bias member 56 is arranged around and generally coaxially with the axis A. The coil spring bias member 56 extends from the needle head 70 to the top of the struts 62. An annular groove 80 may be provided in the bottom surface (relative to the orientation shown in FIGS. 4-6) of the needle head 70, for receiving a portion of a first end of the coil spring bias member 56, to help retain the coil spring bias member 56 in place relative to the needle head 70. In some embodiments, the first end of the coil spring may be secured to the needle head 70 by any suitable connection structure including, but not limited to, adhesive, straps, thermal coupling, or the like.

The struts 62 may include grooves 82 (or an annular groove 82, for embodiments in which a single annular strut 62 is employed) for receiving a portion of a second end of the coil spring bias member 56, to help retain the coil spring bias member 56 in place relative to the struts 62. In further embodiments, the first end of the coil spring bias member 56 may be secured to the needle head 70 and/or the second end of the coil spring bias member 56 may be secured to the struts 62, by any suitable connection structure including, but not limited to, adhesive, straps, thermal coupling, or the like.

The first and second septa 52 and 54 may be made of any suitable material that can be pierced by a needle and form a seal around the needle. The material for septa 52 may be a material that reseals the needle hole after the needle has been removed from septum. Such septum material may include, but is not limited to, a suitable rubber, plastic or the like. As described above, the first septum 52 is supported on the needle carriage 46, for providing a pierceable seal over one end of the central passage 74 of the needle carriage 46. The second septum 54 is supported by the housing structure 44, adjacent an opening of a fluid flow passage 84. The second septum 54 provides a pierceable seal over the fluid flow passage 84. The fluid flow passage 84 may be a channel formed in the housing structure 44, as shown in FIGS. 4-6. In other embodiments, the fluid flow passage 84 may include a tube or other conduit structure located within the housing 44. The fluid flow passage 84 is connected, in fluid flow communication, with a reservoir connector 86.

The reservoir connector 86, may be any suitable connection structure that may be selectively (or, in some embodiments, permanently) connected to a reservoir 28, to provide fluid flow communication with the interior of the reservoir 28. For example, the reservoir connector 86 may include a typical Luer-type connector having a cap structure 88 for receiving an outlet port of the reservoir, a hollow needle 90 for piercing a septum 92 within the outlet port of the reservoir 28. The fluid flow passage 84 is arranged in fluid flow communication with the needle 90. Accordingly, a reservoir 28 may be selectively engaged with the cap 88, to connect the interior of the reservoir 28 in fluid flow communication with the fluid flow passage 84, through the needle 90. In other embodiments, the needle 50 and septum 54 may be eliminated and, instead, a continuous flow path (such as, but not limited to, a flexible tubing) may be coupled to the reservoir 28 and to the central passage 74 or passage 78, and able to flex, stretch or otherwise accommodate movement of the needle carriage 46 relative to the housing structure 44 and maintain a fluid flow path between the reservoir 28 and the central passage 78. In yet further embodiments, the connector 86 may be eliminated, for example, by connecting the flexible tubing directly to the reservoir.

The needle inserter device 12 of FIGS. 4-6 is configured to insert a hollow needle or cannula into a patient-user's skin, for providing fluid flow communication between the reservoir 28 and the patient-user, when the housing structure 44 (such as the housing structure of the disposable housing portion 20 in FIGS. 2 and 3) is secured to a patient-user's skin. In operation, the needle inserter device 12 is configured to move between a retracted state (FIG. 4) and an extended state (where FIG. 5 shows movement toward the extended state). In addition, the needle inserter device has a return state (FIG. 6), at which the hollow needle or cannula 48 and needle carriage 46 are in the extended position, while the moveable needle 42 is returned to a retracted position.

In one embodiment, an external plunger device 41 is employed to cause the needle inserter device to move between a retracted state and an extended state. The plunger 41 may include a hand-held, spring-loaded piston device, which is selectively actuated to provide a relatively abrupt piston motion in the direction of the arrow 58. In other embodiments, the plunger 41 may be controlled to provide a slow needle insertion rate, to minimize traumatic effects to certain patient-users.

For example, the plunger device 41 may include a movable plunger having a plunger head that has a size and shape to allow easy insertion into the opening 25 in the housing structure 44, to engage the needle head 70. The plunger head is selectively activated to be driven in the direction of arrow 58 and impart a force on the needle head 70, in the direction of arrow 58. The force imparted by the plunger 41 on the needle head 70 is sufficient to overcome the bias force of the bias member 56, to move the needle 42 in the direction of the arrow 58, toward the extended position. The plunger may be spring-loaded, to provide a relatively abrupt motion in the direction of arrow 58, when activated, to move the needle 42 relatively quickly, in the direction of arrow 58.

As the needle 42 is moved downward (with respect to the orientation of FIGS. 4-6), in the direction of arrow 58, the needle head 70 engages and forces the needle carriage 46 to move with the needle in the direction of arrow 58. As the needle carriage 46 is moved in the direction of arrow 58, the cannula 48 attached to the needle carriage 46 is also moved in the direction of arrow 58. As the needle 42 and cannula 48 are moved in the direction of arrow 58, the tip of the needle 42 that extends out from the cannula 48 pierces the patient-user's skin. As the needle 42 and cannula 48 continue to move in the direction toward the extended position, the needle 42 directs a portion of the length of the cannula 48 through the patient-user's skin to a desired depth.

As the needle 42 and needle carriage 46 move toward the extended position, the sharp end of the further hollow needle 50 engages and pierces the second septum 54, as shown in FIG. 5. When the needle carriage 46 is moved into the fully extended position (as shown in FIG. 6), the hollow needle 50 is extended through the second septum 54, to fluid flow communication between the fluid flow passage 84 in the housing structure 44 and the fluid flow passage 78 in the needle carriage 46.

Also as the needle 42 and needle carriage 46 move toward the extended position, the needle carriage 46 engages the pawls 60 and causes the pawls 60 to flex downward (relative to the orientation of FIG. 5), in the direction of arrow 58, as the needle carriage 46 continues to move toward the extended position. When the needle carriage 46 reaches the extended position (as shown in FIG. 6), the pawls 60 return toward their un-flexed state and engage the engagement surface 62 of the needle carriage 46, to hold the needle carriage 46 and the cannula 48 in their extended position. Once the pawls 60 have engaged the engagement surface 62 of the needle carriage 46, the plunger 41 may be removed by withdrawing the plunger head through the opening 25. As the plunger 41 is removed, the bias member 56 operates to return the needle 42 to the retracted position of the needle, leaving the needle carriage 46 and cannula 48 in the extended position, as shown in FIG. 6. As the needle 42 retracts, the first septum 52 reseals itself.

As a result, the cannula 48 will be inserted into the patient-user and also will be connected in fluid flow communication with the reservoir 28. Thereafter, infusion medium within the reservoir 28 may be selectively delivered to the patient-user, through the cannula 48 and fluid flow passages 78 and 84, by operation of a drive device on the reservoir 28, as described above. The patient (or other user) may readily operate the needle inserter device by simple operations of inserting the plunger 41 into the opening 25 (to engage the plunger with the needle head 70), activating the plunger 41 (to drive the plunger in the direction of arrow 58), and then withdrawing the plunger 41 from the opening 25.

A seal structure 94 may be provided between the needle head 42 and the housing structure 44, to provide a seal around the opening 25. In the embodiment shown in FIGS. 4-6, the seal structure 94 may include one or more o-ring seals, gaskets or other suitable seals arranged around the opening 25. One or more annular grooves 96 may be provided in the upper surface (relative to the orientation of FIGS. 4-6) of the needle head 70, for receiving one or more seals. One or more annular protrusions 98 may be provided on an interior surface of the housing structure 44, for engaging the one or more seals, when the needle 42 is in the retracted position, as shown in FIGS. 4 and 6. Alternatively, one or more seals 94 and grooves 96 may be provided on an interior surface of the housing structure 44, while the annular protrusion(s) may be provided on the needle head 70. In further embodiments, a pierceable or removable seal may be provided over the opening through which the needle and cannula extend, when in the extended position. In addition, a seal may be formed between the housing structure 44 and the needle carriage 46, by compression of a portion of the cannula 48 (the flared portion shown in the upper end of the cannula 48, with respect to the orientation shown in FIG. 6) between the housing structure 44 and the needle carriage 46, when the needle carriage 46 is moved to the extended position (shown in FIG. 6). Accordingly, the cannula 48 (or, at least the flared end of the cannula 48 that is located between the housing structure 44 and the needle carriage 46) may be made of a material that can be compressed to form a seal between the housing structure 44 and the needle carriage 46, when the needle carriage 46 is in the extended position (as in FIG. 6).

While an embodiment of a needle inserter device 40 in FIGS. 4-6 employs an external plunger 41 for moving the needle 42, needle carriage 46 and cannula 48 from a retracted position to an extended position, other embodiments may employ internal activation and bias structure for imparting a force to selectively move those components into the retracted position. For example, FIGS. 7 and 8 show an embodiment of a needle inserter device 140 in which a further bias member is selectively actuated to provide a bias force on a needle 142, needle carriage 146 and cannula 148, in the direction toward an extended position.

Figure 7:
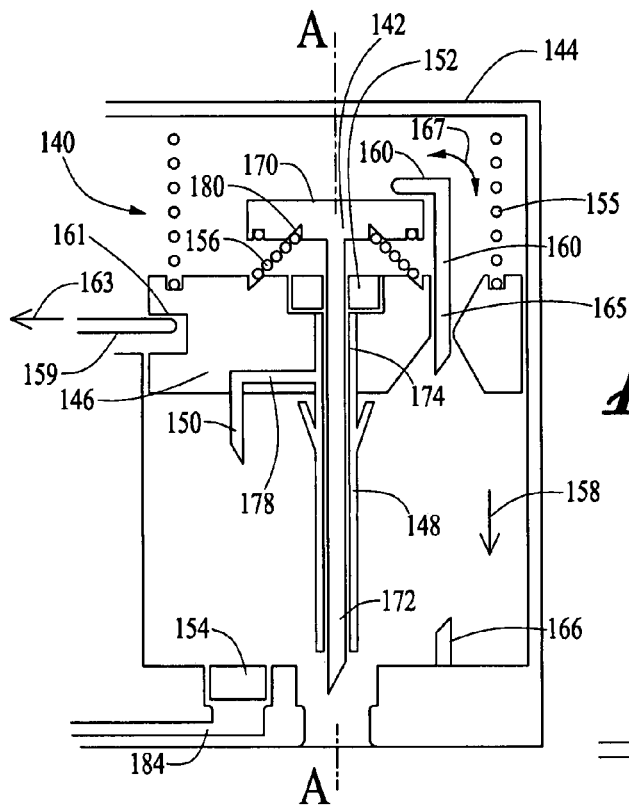
FIG. 7 a schematic, cross-sectional view of a needle inserter device within the delivery device of FIGS. 2 and 3, according to another embodiment of the invention, wherein a needle and a cannula are each in a retracted position.
Figure 8:
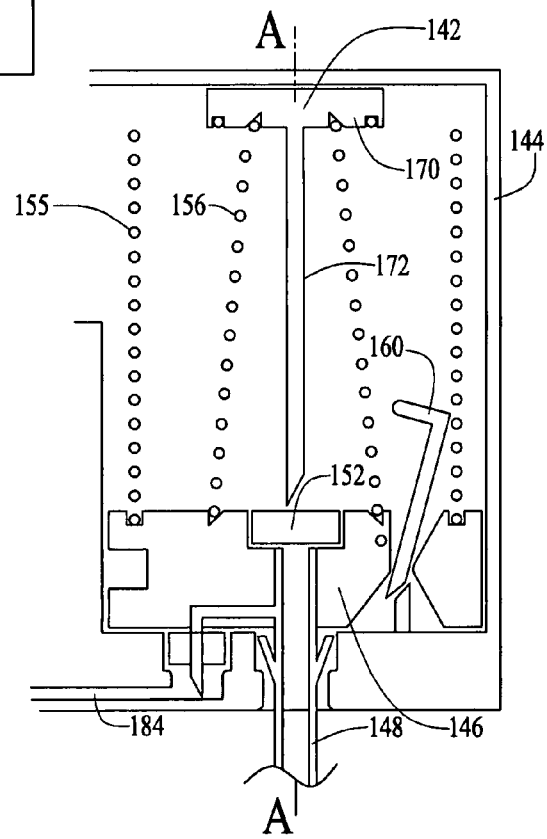
FIG. 8 is a schematic, cross-sectional view of the needle inserter device of FIG. 7, wherein the cannula is in a fully extended position and the needle is in a retracted position.

The embodiment of FIGS. 7 and 8 is similar in certain structural and functional respects to the embodiment of FIGS. 4-6. For example, the moveable needle 142, needle carriage 146 and cannula 148 of FIGS. 7 and 8 may be similar to the needle 42, needle carriage 46 and cannula 48 in certain respects. In addition, the embodiment of FIGS. 7 and 8 include first and second septa 152 and 154 and a further needle 150, similar to the first and second septa 52 and 54 and needle 50 described above (or a flexible tubing instead of the second septum 54 and needle 50, as described above). For example, the needle 142 includes a needle head 170 and needle shaft 172, similar to the needle head 70 and needle shaft 72 described above. Also, the embodiment of FIGS. 7 and 8 include flow channels 178 and 184, which have similar structure and function as the flow channels 78 and 84, described above, for providing a fluid flow path between a central passage 174 of the needle carriage 146 and a reservoir (not shown in FIGS. 7 and 8).

However, unlike the embodiment of FIGS. 4-6, the embodiment of FIGS. 7 and 8 includes a first bias member 155 for providing a bias force on the needle carriage 146 in the direction of arrow 158, when the needle carriage is in the retracted position shown in FIG. 7. For example, the bias member 155 may include a coil spring provided around and generally coaxial with a central axis A of the needle 142 and cannula 148. The coil spring bias member 155 may be compressed to a compressed state as shown in FIG. 7 and, when released, may expand under its own spring force to an expanded state shown in FIG. 8. A first end of the coil spring bias member 155 is abutted against an interior surface of the housing structure 144 (which may include a section of the disposable housing portion 20 of the delivery device shown in FIGS. 2 and 3, or may be a housing structure that is separate from the housing structure of the delivery device). The second end of the coil spring bias member 155 is abutted against an upper surface (relative to the orientation shown in FIGS. 7 and 8) of the needle carriage 146.

The needle carriage 146 may include an annular groove for receiving a portion of the second end of the coil spring bias member 155, to help retain the coil spring in place with respect to the needle carriage 146. Similarly, an annular groove may be provided in the interior surface of the housing structure 144, for receiving a portion of the first end of the coil spring bias member, to help retain the coil spring in place with respect to the housing structure 144. The first and second ends of the coil spring bias member 155 may be secured to the housing structure 144 and needle carriage 146, respectively, by any suitable connection structure including, but not limited to, adhesive, straps, thermal coupling, or the like.

The coil spring bias member 155 is configured to be in a compressed state, when the needle carriage 146 is in the retracted position (shown in FIG. 7), and an expanded state, when the needle carriage 146 is in the extended position (shown in FIG. 8). When in the compressed state shown in FIG. 7, the coil spring bias member 155 imparts a bias force on the needle carriage 146, in the direction of arrow 158. The needle carriage 146 may be held in the retracted position user (or other user) to selectively activate the needle inserter device by releasing the needle carriage and allowing the force of the bias member 155 to move the needle carriage 146 in the direction of the arrow 158. In the embodiment of FIG. 7, the actuation member 159 includes a rigid lever (or other structural member) that engages a stop surface 161 on the needle carriage 146 and is moveable in the direction of arrow 163 (by actuation of a manual lever, button or other operator, not shown) to a position in which the lever does not engage the stop surface 161, to allow the needle carriage 146 to move in the direction of arrow 158, under the force of the first bias member 155. While a manual lever, button or other operator may be employed to initiate movement of the actuation member 159, other embodiments may employ an automatic activation mechanism for moving the actuation member 159 (or otherwise release the needle carriage 146 for movement in the direction of arrow 158), such as, but not limited to, a mechanism that moves the actuation member 159 or otherwise releases the needle carriage for movement, in response to an expiration of a period of time from a sensor detecting the application of the delivery device (or components thereof) on the skin of user (or in another suitable location of operation). In yet other embodiments, suitable electronics may be included in the delivery device to allow the actuation member 159 (or other suitable mechanism for releasing the needle carriage 146 for movement in the direction of arrow 158) to be activated by a signal from the CCD 16 or the computer 18, for example, through a programmed timing sequence or in response to an input from a user of the CCD 16 or computer 18.

The embodiment of FIGS. 7 and 8 includes a second bias member 156, for providing a bias force on the needle 142, in the direction opposite to the direction of arrow 158. In the example embodiment of FIGS. 7 and 8, the second bias member 156 includes a coil spring, which is configured to be compressed to the state shown in FIG. 7 and expand under its own spring force to the state shown in FIG. 8. The coil spring bias member 156 may be made of any suitable spring material, including, but not limited to, metal, plastic, composite material or the like, and is arranged around and generally coaxially with the longitudinal axis A of the needle shaft 172 and the cannula 148.

The upper surface (relative to the orientation direction of FIGS. 7 and 8) of the needle carriage 146 may include an annular groove for receiving a portion of the one end of the coil spring bias member 156, to help retain the coil spring in place with respect to the needle carriage 146. Similarly, an annular groove 180 may be provided on the lower surface (relative to the orientation direction in FIGS. 7 and 8) of the needle head 170, for receiving a portion of the other end of the coil spring bias member 156, to help retain the coil spring in place with respect to the needle head 170. The ends of the coil spring bias member 156 may be secured to the needle head 170 and needle carriage 146, respectively, by any suitable connection structure including, but not limited to, adhesive, straps, thermal coupling, or the like.

In the retracted position shown in FIG. 7, the coil spring second bias member 156 is held in a compressed state, by at least one pivotal pawl 160. In FIG. 7, one pawl 160 is shown. However, in other embodiments, two or more pivotal pawls, similar to pawl 160, may be located around the perimeter of the needle carriage 146. The pawl 160 includes a rigid lever mounted to the needle carriage 146 by a pivotal connection 165, for pivotal motion in the directions of the double arrow 167. In FIG. 7, the pawl 160 is in a locking position, at which a surface of the pawl abuts the upper surface (relative to the orientation in FIG. 7) of the needle head 170. In the locking position, the pawl 160 retains the needle 142, against the force of the coil spring bias member 156, to maintain the coil spring bias member 156 in its compressed state.

On the other hand, as the needle carriage 146 and cannula 148 are moved to the extended position, the pawl 160 engages an engagement surface 166 on the housing structure 144 and pivots to disengage from the needle head 170 and release the needle 142, as shown in FIG. 8. The surface of the pawl 160 that engages the engagement surface 166 may be provided with an angle surface (having an angle or curvature relative to the longitudinal axis A direction) and the engagement surface 166 may be angled in a corresponding direction, to enhance pivotal motion of the pawl 160, as the needle carriage is moved into an extended position.

Upon the pawl 160 being pivoted to release the needle 142, the bias force of the coil spring second bias member 156 causes the needle 142 to be returned to the retracted position, leaving the needle carriage 146 and cannula 148 in the extended position, as shown in FIG. 8. When the needle 142 is returned to the retracted position, the septum 152 re-seals itself and the cannula 148 is arranged in fluid flow communication with the reservoir (not shown), through the fluid flow passages 178 and 184, in a manner similar to the manner in which cannula 48 is arranged in fluid flow communication with the reservoir 28, through passages 78 and 84 in FIG. 4.

In operation, with the needle 142, needle carriage 146 and cannula 148 in the retracted position (as shown in FIG. 7), the housing structure 144 is secured to a user's skin, for example, in a manner similar to that described above with respect to securing the disposable housing portion 20 to a user's skin. The patient-user (or other user) may activate the needle inserter device by moving the activation lever 159 from the stop surface 161 of the needle carriage, to release the needle carriage. Upon releasing the needle carriage 146, the force of the coil spring first bias member 155 abruptly moves the needle carriage 146 downward (relative to the orientation in FIG. 7) in the direction of arrow 158, toward the extended position (i.e., toward the position shown in FIG. 8). As the needle carriage 146 is abruptly moved in the direction of arrow 158, the pawl 160 that abuts the needle head 170 causes the needle 142 to abruptly move downward (relative to the orientation in FIG. 7) in the direction of arrow 158, with the needle carriage 146. In further embodiments, the bias member 155 and/or the needle carriage 146 may include suitable motion damping structure or the like for causing the needle 142 to move slowly into a patient-user's skin, to minimize traumatic effects on the patient-user, upon releasing the needle carriage 146.

As the needle carriage 146 nears the extended position (shown in FIG. 8), a surface of the pawl 160 contacts the engagement surface 166. Further movement of the needle carriage 146 toward the extended position causes the pawl 160 to pivot about its pivot axis 165, to disengage the needle head 170. When the pawl 160 is pivoted out of engagement with the needle head 170, the bias force of the coil spring second bias member 156 returns the needle 142 to its retracted position, leaving the needle carriage 146 and cannula 148 in the extended position, as shown in FIG. 8. As the needle 142 retracts, the septum 152 reseals itself.

As a result, the cannula 148 will be inserted into the patient-user and also will be connected in fluid flow communication with a reservoir (not shown). Thereafter, infusion medium within the reservoir may be selectively delivered to the patient-user, through the cannula 148 and fluid flow passages 178 and 184, by operation of a drive mechanism on the reservoir, as described above. The patient-user (or other user) may readily activate the needle inserter device by simple operation of the operator that controls movement of the actuation lever 159.

While the embodiment in FIGS. 7 and 8 employs a pivotal pawl 160, other embodiments may employ other suitable catch mechanisms, including, but not limited to, a rotary pawl, a flexible pawl, an electrically actuated solenoid or the like, for selectively retaining the needle 142 with the needle carriage 146 and selectively releasing the needle 142 from the needle carriage upon the needle carriage being moved toward or into its extended position.

In the embodiment of FIGS. 4-6, an external plunger device 141 is employed to impart a force on the needle 42, to move the needle, the needle carriage 46 and the cannula 48 from a retracted position to an extended position. In the embodiment of FIGS. 7 and 8, a bias member, such as a coil spring, imparts a force on the needle carriage 146, to move the needle carriage 146, needle 142 and cannula 148 to an extended position. In further embodiments, a rotary drive mechanism may be employed for selectively moving the needle, needle carriage and cannula toward and into an extended position.

Figure 9:
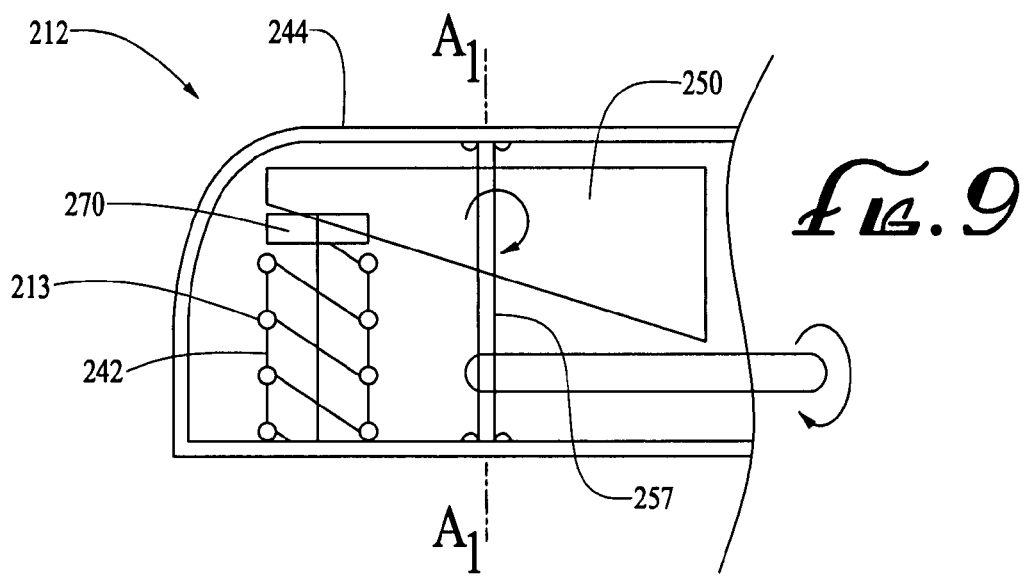
FIG. 9 a schematic, cross-sectional view of a needle inserter device within the delivery device of FIGS. 2 and 3, according to another embodiment of the invention, wherein a needle and a cannula are each in a retracted position.
Figure 10:
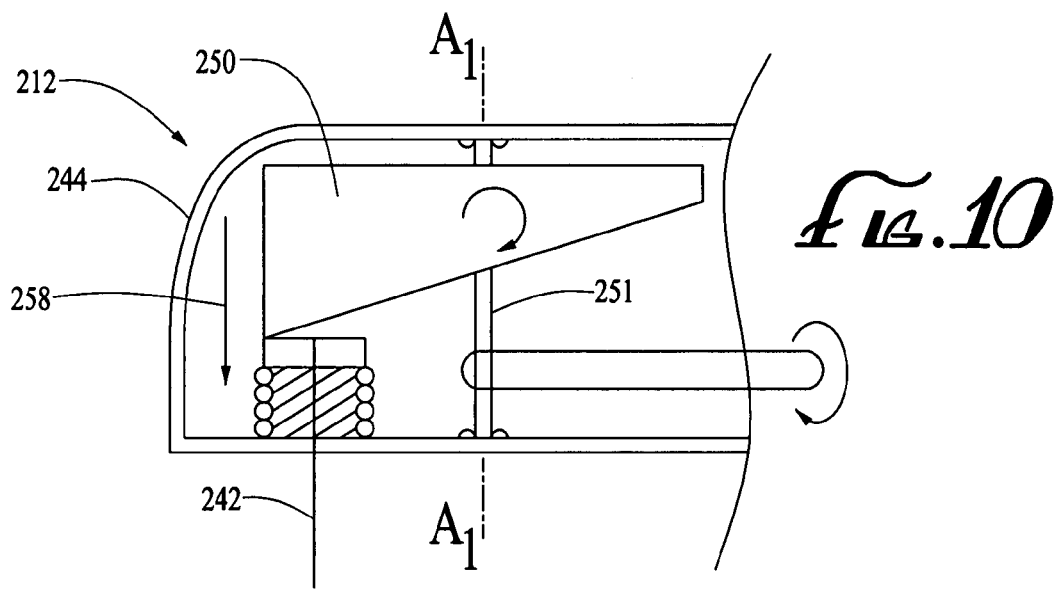
FIG. 10 is a schematic, cross-sectional view of the needle inserter device of FIG. 9, wherein the needle and cannula are each in an extended position.

For example, an embodiment of a rotary drivable needle inserter device 212 is shown in FIGS. 9 and 10. The needle inserter device 212 may include a structure 213 that includes a needle 242, needle carriage, cannula, a first septum, a bias member and a second septum (or a flexible tubing), similar to the needle 42, carriage 46, cannula 48, first septum 52, coil spring bias member 56 and second septum 54 (or flexible tubing) of FIGS. 4-6. Alternatively, the structure 213 may include a needle 242, needle carriage, cannula, first and second septa and a bias member, similar to the needle 142, carriage 146, cannula 148, septa 152 and 154 and coil spring bias member 156 of FIGS. 7 and 8. While not shown in FIGS. 9 and 10, the needle inserter device 212 may be supported within a housing having a fluid flow path, reservoir connector and reservoir, similar to the fluid flow path 84, reservoir connector 86 and reservoir 28 shown in FIG. 4. Accordingly, the needle inserter device 212 operates in a manner similar to the manner of operation of the needle inserter devices 12 and 112, described above. However, actuation of the needle inserter device 212 is carried out by the rotary motion of a rotatable cam member 250.

With reference to FIGS. 9 and 10, the rotatable cam member 250 includes a rotary disk-shaped member having a central axis, along the axial direction $A_1$, which may be substantially parallel to the axis A of the needle 242. The disk shaped cam member 250 may be made of any suitably rigid material, including, but not limited to, metal, plastic, ceramic, composite material or the like. The disk shaped cam member 250 has a width that varies across its diameter, as shown in FIGS. 9 and 10, so as to be thinner on one side of the central axis $A_1$ than on the other side of the central axis $A_1$. Accordingly, the disk-shaped cam member 250 provides a rotatable wedge, which functions to move the needle 242 from a retracted position (shown in FIG. 9) to an extended position (shown in FIG. 10), as the disk shaped cam member 250 rotates from the position shown in FIG. 9 to the position shown in FIG. 10.

The rotary disk shaped cam member 250 is supported for rotation about the axis $A_1$, on a rotary shaft 251. The rotary shaft 251 is operatively coupled, through suitable linkage structure (not shown), such as gears, belts, drive shafts or the like, to a drive device (not shown), for rotation about the axis $A_1$. The drive device and linkage structures (not shown), may include any suitable drive device and linkage structures for providing selective rotational motion to the shaft 251. For example, an electronic motor or other drive device described herein may be employed. In a further embodiment, the rotary shaft 251 may be operatively coupled to a wound spring (or windable spring), to provide rotary drive force to the shaft 251, instead of an electronic motor. Further examples of drive device and linkage structures that selectively drive a rotatable shaft are described, for example, in U.S. patent application Ser. No. 11/211,095, filed Aug. 23, 2005, U.S. Patent Application No. 60/839,822, filed Aug. 23, 2006, and U.S. Patent Application No. 60/839,832, filed Aug. 23, 2006, each of which is incorporated herein by reference.

In the retracted position of the needle 242 (shown in FIG. 9), the disk-shaped cam member 250 may be arranged to abut (or be adjacent, but spaced from) the upper surface (relative to the orientation of FIG. 9) of the head 270 of the needle 252. In operation, the rotary cam member 250 is driven in a rotational motion about the axis $A_1$ by selective operation of a rotary drive device. A button, switch, or other operator (not shown) may be operatively connected to the drive device, a power source therefore or the like, to allow a user to selectively activate the drive device, in a manner well known in the art.

As the rotary cam member 250 rotates from the position shown in FIG. 9, the relatively wide portion of the disk-shaped cam member 250 is rotated around to abut the head 270 of the needle 252 and pushes the needle 252 in the direction of arrow 258, into the extended position, as shown in FIG. 10. As described above with respect to the embodiments of FIGS. 4-8, a needle carriage and cannula may be moved, with the movement of the needle 252, in the direction of arrow 258, to an extended position. Once the needle 242, needle carriage and cannula are moved into the extended position (FIG. 10), further rotation of the disk-shaped cam member 250 causes the relatively thin portion of the cam member 250 to rotate around into engagement with the head 270 of the needle 252, allowing a bias member 256 (such as a coil spring, or the like) to return the needle 242 to the retracted position (shown in FIG. 9), while the needle carriage and cannula may remain in the extended position, as described above with respect to the embodiments of FIGS. 4-8. In the embodiment of FIGS. 9 and 10, the rotary cam member 250 may be controlled to rotate in a relatively fast, abrupt motion from the position in FIG. 9 to the position in FIG. 10, to move the needle 252 relatively abruptly through the patient-user's skin, to minimize traumatic effects on the patient-user. Alternatively, the rotary cam member 250 may be controlled to rotate in a relatively slow motion, to move the needle 252 relatively slowly through the patient-user's skin, to minimize traumatic effects on other patient-users. The speed of rotation of the rotary cam member 250 may be controlled by controlling the speed of the drive device, and/or by providing speed reduction gearing or the like in the linkage structure that couples the drive device to the rotary cam member 250.

A further embodiment of a needle inserter device 312 capable of self activation and retraction is described with reference to FIGS. 11-13. The needle inserter device 312 includes a moveable needle 342, a needle carriage, a cannula, a first septum, a bias member, and a further needle and a second septum (or flexible tubing), similar to the needle 42, carriage 46, cannula 48, first septum 52, coil spring bias member 56 and further needle 50 and second septum 54 (or flexible tubing) of FIGS. 4-6. Alternatively, needle inserter device 312 may include a needle 342, needle carriage, a cannula, a first septum and a further needle and second septum (or a flexible tubing), similar to the needle 142, carriage 146, a cannula 148, first septum 152, coil spring bias member 156 and further needle 150 and second septum 154 (or flexible tubing) of FIGS. 7 and 8. While not shown in FIGS. 11-13, the needle actuator 312 may be supported within a housing having a fluid flow path, reservoir connector and reservoir, similar to the housing structure 44, fluid flow path 84, reservoir connector 86 and reservoir 28 shown in FIG. 4. Accordingly, the needle actuator 312 operates in a manner similar to the manner of operation of the needle inserter devices 12 and 112, described above. However, actuation of the needle inserter device 312 is carried out by a firing spring mechanism 350.

The firing spring mechanism 350 includes a spring having a coil portion 351 and two arm portions 352 and 353, respectively, in accordance with common spring configurations of the type used in traditional mouse-trap structures, or the like. The firing spring mechanism may be composed of any suitable spring material, including, but not limited to metal, plastic, composite material, or the like.

One of the arms 352 of the firing spring mechanism 350 may be connected in a fixed relation relative to a housing (such as the housing 44 or 144 described above). The second arm 353 is biased, by the force of the coil portion 351 of the spring mechanism 350, in the direction of the arrow 354. A actuator lever 355 is arranged to abut the second arm 353, to hold it in place against the bias force of the coil portion 351. The actuator lever 355 is moveable, in response to the operation of a manual button, lever or other operator accessible to the patient-user (or other user), in the direction of arrow 356 (or other suitable direction, e.g., into or out of the plane of the page of FIG. 11), to selectively disengage the spring arm 353. Upon the actuator lever 355 disengaging the spring arm 353, the spring arm 353 is caused to abruptly move in the direction of arrow 354, by the force of the coil portion 351.

Figure 11:
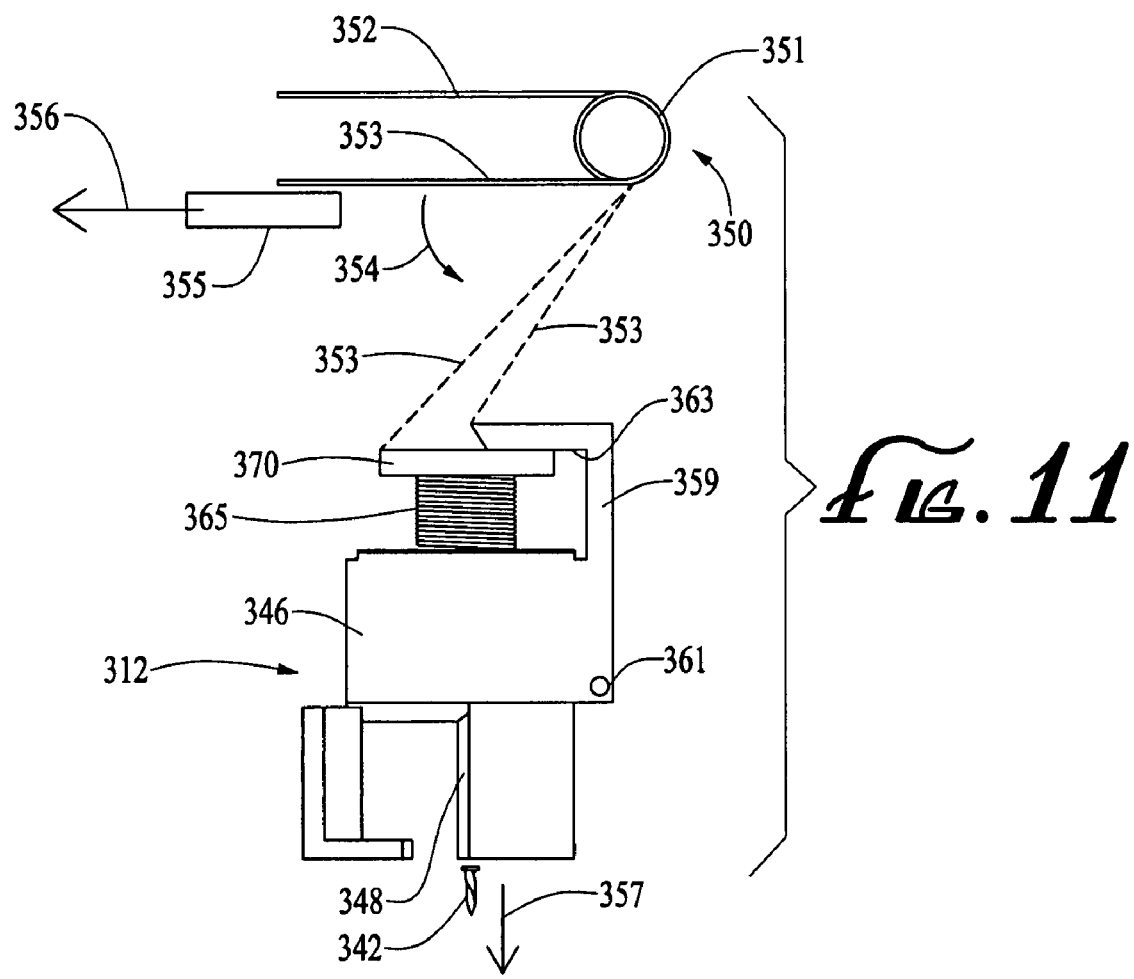
FIG. 11 is a perspective view of a needle inserter device according to another embodiment of the invention, wherein a needle and a cannula are each in a retracted and ready-to-be activated position.

As the spring arm 353 is moved in the direction of arrow 354, the spring arm 353 initially contacts the head 370 of the needle 342, as shown in broken lines in FIG. 11. As the spring arm 353 continues to move in the direction of arrow 354, the spring arm 353 pushes downward (relative to the orientation direction of FIG. 11) on the needle head 370, in the direction of arrow 357, to cause the needle 342 (and the needle carriage and cannula) to move into an extended position. In the extended position, the cannula is connected in fluid flow communication with a reservoir, for example, in a manner similar to that described above with respect to the connection of the cannula 48 with the reservoir 28, through the fluid flow passages 78 and 84, in FIG. 4. While the spring arm 353 may be allowed to move in the direction of arrow 354 (upon the actuator lever disengaging the spring arm 353) in an abrupt motion to minimize trauma to certain patient-users, in further embodiments, a motion damping mechanism may be coupled to the spring arm 353 and/or the needle 342, to cause the needle 342 to move slowly in the direction of arrow 354 (when actuated), to minimize traumatic effects to other patient-user.

Upon engaging the needle head 370 and moving the needle 342 in the direction of the arrow 357, the spring arm 353 continues to move in the direction of arrow 354 and engages a pivotal lever 359. The pivotal lever 359 may include a suitably rigid structure that is mounted for pivotal motion about a pivot axis 361 and includes a stop surface 363 arranged to engage the upper surface (in the orientation of FIG. 11) of the needle head 370, to hold the needle head in a partially extended position (as shown in FIG. 11) against the force of a return spring 365.

The return spring 365 may include a coil spring or other suitable bias mechanism, for biasing the needle 342 in the direction opposite to the direction of arrow 357. In the embodiment of FIG. 11, the return spring 365 is disposed around and generally coaxial with the shaft of the needle 342, and has one end that abuts the lower surface (relative to the orientation of FIG. 11) of the needle head 370. A second end of the return spring 365 abuts an upper surface (relative to the orientation of FIG. 11) of a positioning channel structure 346. The positioning channel structure may include a portion of the housing structure 44 described above, or a further structure (made of suitably rigid material, such as, but not limited to, plastic, metal, ceramic, composite material, or the like) located within the housing structure 44 described above.

Figure 12:
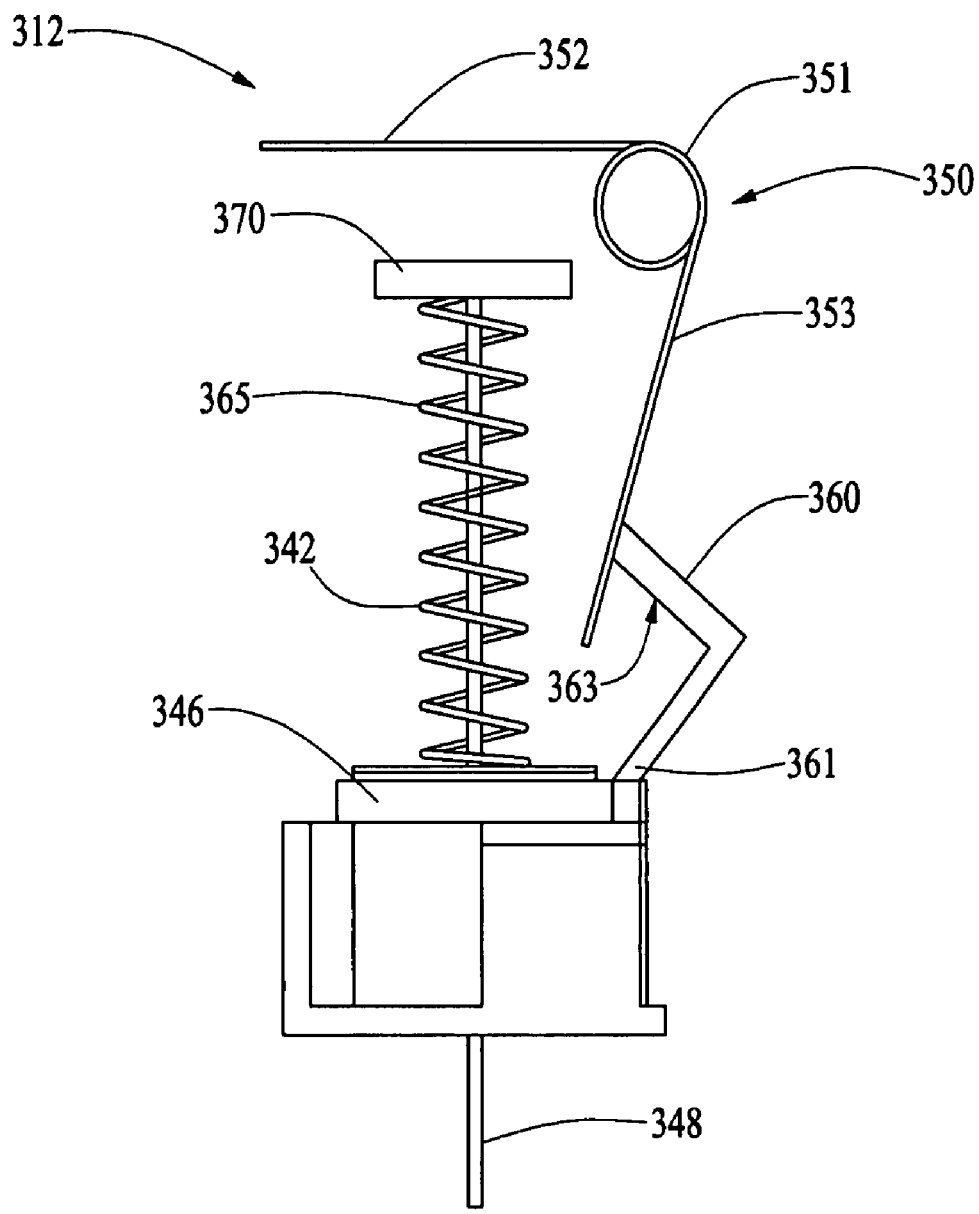
FIG. 12 is a side view of the needle inserter device embodiment of FIG. 11, wherein the cannula is in an extended position and the needle is in a retracted position.
Figure 13:
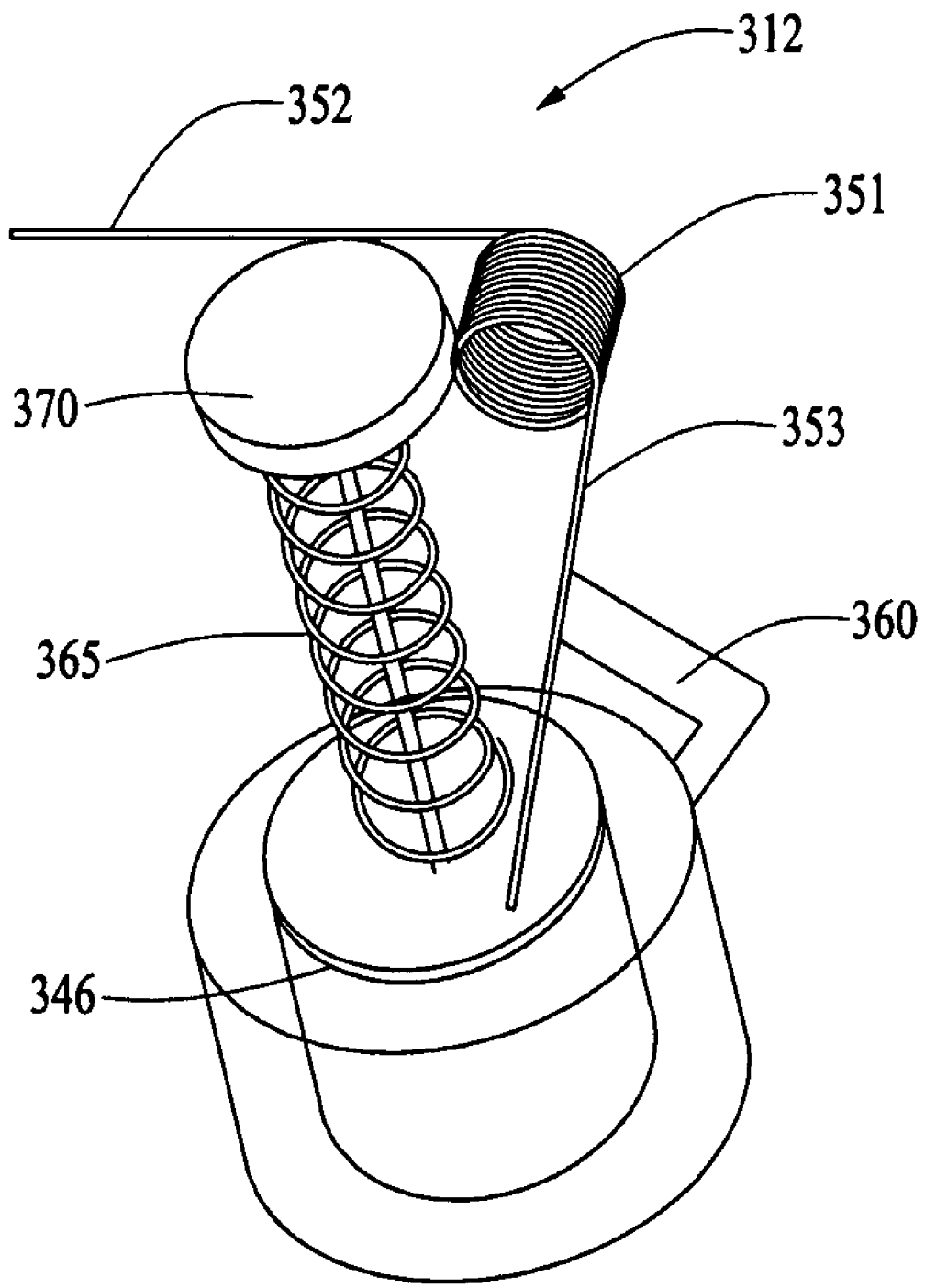
FIG. 13 is a perspective view of the needle inserter embodiment of FIG. 12.

Upon engaging the pivotal lever 359, further movement of the spring arm 353 in the direction of the arrow 354, by the force of the coil portion 351, causes the spring arm 353 to pivotally move the pivotal lever 359 to a position at which the stop surface 363 of the lever 359 is disengaged from the needle head 370, as shown in FIGS. 12 and 13. When the lever 359 pivots to disengage the needle head 370, the coil spring 365 is allowed to expand under its own spring force, to move the needle 342 to a retracted position, as shown in FIGS. 12 and 13.

Accordingly, as the spring arm 353 moves in the direction of the arrow 354, from the position shown in FIG. 11 to the position shown in FIGS. 12 and 13, the spring arm 353 engages the needle head 370 and forces the needle 342 downward (relative to the orientation of FIG. 1) toward an extended position, whereupon the cannula is inserted through a patient-user's skin and is locked into place, in fluid flow communication with a reservoir. The spring arm 353 continues its motion in the direction of arrow 354, to engage the pivotal lever 359 and pivotally move the pivotal lever 359 out of engagement with the needle head 370. Upon disengagement of the pivotal lever 359 with the needle head 370, the spring 365 moves the needle to its retracted position, leaving the cannula in place, extending through the patient-user's skin. The spring tension of the spring 365 may be selected so as to provide a relatively abrupt motion of the needle to its retracted position, to minimize discomfort to the patient-user. In further embodiments, a motion reduction mechanism may be coupled to the spring, or needle 342 to cause the needle 342 to move slowly through the patient-user's skin, to minimize discomfort to other patent-users.

While various embodiments described above employ bias members in the form of coil springs, other embodiments may employ other types of bias members, suitable to provide a sufficient bias force in the directions described herein. For example, other spring arrangements may be employed to provide a bias force for inserting a moveable needle and cannula into a patient-user and/or a bias force for removing the needle, while leaving the cannula in place. An example embodiment of a needle inserter device 412 that employs a single leaf type spring to provide both bias forces is shown in FIGS. 14-16.

Similar to embodiments described above, the needle inserter device 412 of FIGS. 14-16 includes a moveable needle 442 that is moveable relative to a housing structure 444. Similar to the above embodiments, the moveable needle 442 may be extended through a central passage in a needle carriage 446 and through a cannula 448 (as shown in FIGS. 14 and 15), but also may be withdrawn from at least a portion of the cannula 448 (as shown in FIG. 16). The housing structure 444 may be similar to the housing structure 44 or 144 described above. The carriage 446 may be similar to the carriage 46 or 146 described above, including a further hollow needle and fluid flow passage (such as described above with respect to the further needle 50 and fluid flow path 78 of FIG. 4) for piercing a septum and coupling in fluid flow communication with a fluid flow path in or supported by the housing structure 444 (such as described above with respect to the septum 54 and fluid flow path 84 of FIG. 4).

The needle carriage 446 is supported for motion in the direction of arrow 458 and may be guided by rails, ribs, walls or other structural features 450 of or in the housing 444, provided along that direction of motion. In FIG. 14, the needle inserter device 412 is shown in a ready state, in which the needle carriage 446, needle 442 and cannula 448 are supported in a retracted position and ready to be activated. In FIG. 15, the needle inserter device 412 is shown in an insert state, in which the needle carriage 446, needle 442 and cannula 448 have been moved to an extended position where the needle 442 and cannula 448 may pierce the skin of a patient-user on whom the housing 444 is secured. In FIG. 16, the needle inserter device 412 is shown in a needle retract state, in which the needle 442 has been retracted from the patient-user and at least a portion of the cannula 448.

Figure 14:
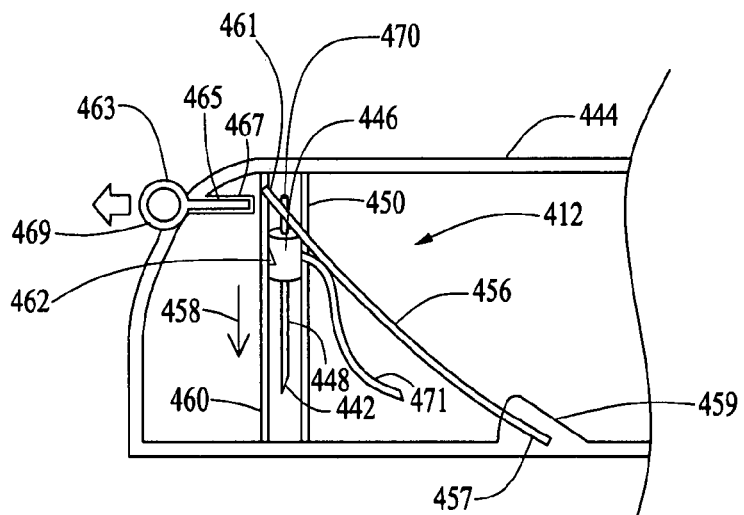
FIG. 14 a schematic, cross-sectional view of a needle inserter device within the delivery device of FIGS. 2 and 3, according to another embodiment of the invention, wherein a needle and a cannula are each in a retracted position.
Figure 15:
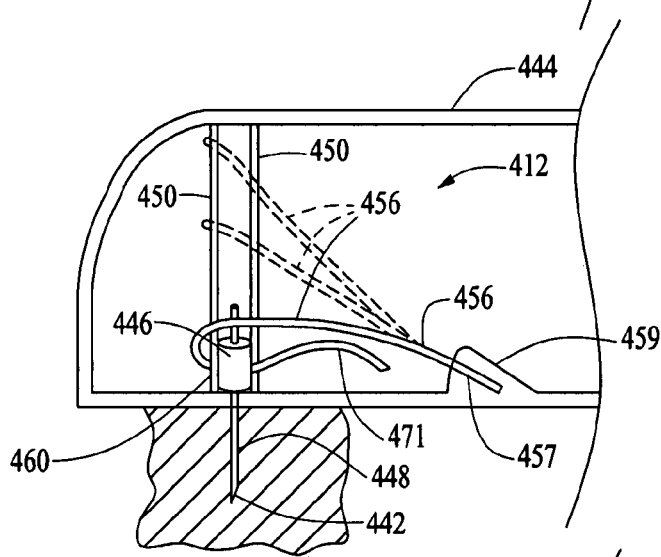
FIG. 15 is a schematic, cross-sectional view of the needle inserter device of FIG. 14, wherein the needle and cannula are each in a partially extended position.
Figure 16:
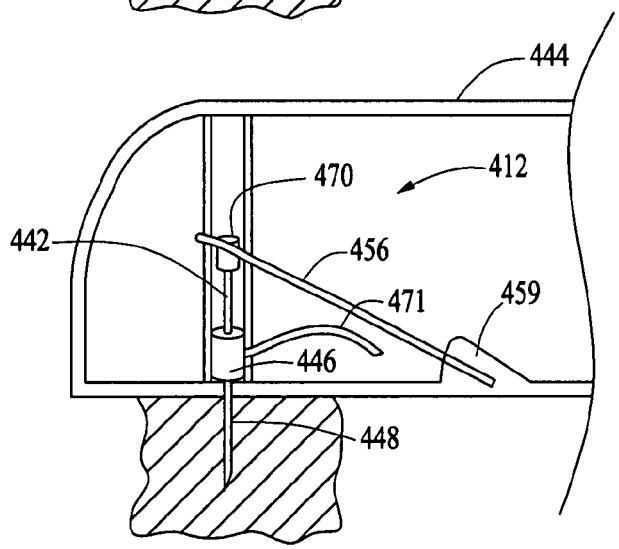
FIG. 16 is a schematic, cross-sectional view of the needle inserter device of FIG. 14, wherein the cannula is in a fully extended position and the needle is in a retracted position.

The needle inserter device 412 has a bias member, such as leaf spring 456, to provide a bias force for moving the needle 442, needle carriage 446 and cannula 448 from the ready state (retracted positions) of FIG. 14, to the insert state (extended position) of FIG. 15. The leaf spring bias member 456 also provides a bias force for moving the needle 442 from the insert state (extended position) of FIG. 15 to the needle retract state of FIG. 16.

In particular, the leaf spring 456 is secured at one end portion 457 to an anchor structure 459, and a second end portion 461 secured to the head 470 of the needle 442. The leaf spring 456 has a natural tendency to be relatively straight, between the two end portions 457 and 461. When the needle 442, needle carriage 446 and cannula 448 are in the ready state (retracted position) of FIG. 14, the leaf spring 456 is arched or bowed against its natural spring force, to impart a bias force on the needle 442 in the direction of the arrow 458.

The needle 442, needle carriage 446 and cannula 448 may be held in place in the ready state (retracted position) of FIG. 14 by any suitable trigger mechanism. In one embodiment, the trigger mechanism may include a moveable pin or lever 463 that extends through an opening 465 in the housing structure 444 and has one end 467 located inside of the housing structure 444, for engaging the end portion 461 of the leaf spring 456. The pin or lever 463 and or the end portion 461 of the leaf spring 456 may include a catch mechanism, latch, hook or other configuration that allows the pin 463 to hold the end portion 461 of the leaf spring 456 in the arched or bowed state of FIG. 14, against its natural spring force, yet allow the pin or lever 463 to be selectively, manually moved to disengage the end portion 461 of the leaf spring 456 and release the leaf spring 456. Once the pin or lever 463 releases the leaf spring 456, the natural spring force of the leaf spring 456 moves the needle 442, needle carriage 446 and cannula 448 in the direction of arrow 458, to the insertion state of FIG. 15. The pin or lever 463 has a second end 469, located outside of the housing structure 444, for manual activation by a patient-user (or other user).

As described above, by manually activating the pin or lever 463 to disengage the end portion 461 of the leaf spring 456, the leaf spring 456 moves the needle 442, needle carriage 446 and cannula 448 in the direction of arrow 458, to the insertion state of FIG. 15. More specifically, the end portion 461 of the leaf spring 456 pushes downward (in the orientation shown in FIG. 14), in the direction of arrow 458, on the head 470 of the needle 442. The force of the leaf spring 456 is conveyed by the needle head 470 to the needle carriage 446 and cannula 448, to drive those components to the insertion state (extended position) shown in FIG. 15. As the needle 442 is moved to the insertion state (extended position), the sharp end of the needle that protrudes from the end of the cannula 448 pierces the patient-user's skin and inserts the cannula 448 into the patient-user. At the same time, the cannula 448 may be connected in fluid flow communication with a reservoir (for example, in the manner described above with respect to FIGS. 4-8). Alternatively, a reservoir (not shown in FIGS. 14-17) may be connected in fluid flow communication with the central passage of the needle carriage 446, through a flexible conduit 471 that moves and/or flexes with the movement of the needle carriage 446. Also, other embodiments described above with respect to FIGS. 4-13 may include a flexible conduit (similar to conduit 471) connected to the central passage of the needle carriage 446 and in fluid flow communication with a reservoir (e.g., instead of the further hollow needle 50, fluid channels 78 and 84 and septum 54 described above with respect to FIGS. 4-6).

When the needle carriage 446 is moved to the insertion state (extended position) of FIG. 15, the needle carriage 446 is locked into position by a locking pawl 460. In particular, a locking pawl 460 extends into the path of motion of the needle carriage 446 and is engaged by the needle carriage 446, as the needle carriage 446 is moved to the insertion state (extended position) of FIG. 15. The pawl 460 is supported on or in the housing structure 444 and may be similar in structure and function to the pawl 60 described with respect to FIGS. 4-6.

The pawl 460 may bend or pivot downward (relative to the orientation of FIGS. 14-16) as at least a portion of the needle carriage 446 passes the pawl 460, until a stop surface 462 on the needle carriage 446 moves past the pawl 460. Upon the stop surface 462 moving past the pawl 460, the pawl 460 is allowed to flex or pivot back toward its un-flexed or non-pivoted position and engages the stop surface 462. With the pawl 460 engaging the stop surface 462, the needle carriage 446 is inhibited from moving upward (relative to the orientation of FIGS. 14-16) in the direction opposite to the direction of arrow 458. In that manner, the needle carriage 446 and cannula 448 may be held in place, in the insert state (extended orientation) of FIG. 15.

The position of the needle head 470, when the needle carriage 446 is in the insert state (extended position) of FIG. 15 is below (in the orientation of FIG. 15) the position of the end portion 461 of the spring 456 in its unflexed, natural or straight orientation (shown in broken lines in FIG. 15 and in solid lines in FIG. 16), such that the leaf spring 456 is arched or bowed against its natural spring force, when in the insert state (extended orientation) of FIG. 15. Accordingly, upon the spring 456 moving the needle 442, needle carriage 446 and cannula 448 to the insert state (extended position) of FIG. 15, the leaf spring automatically returns to its unflexed, straight state and, in doing so, imparts a force on the needle head 470 to move the needle 442 in the direction opposite to the direction of arrow 458, to the needle retract state shown in FIG. 16. As the needle 442 is moved in the direction opposite to the direction of the arrow 458, the needle 442 is withdrawn from the patient-user and from at least a portion of the cannula 448, leaving the cannula 448 in place, in the patient-user and ready to deliver the infusion medium to the patient-user.

The spring tension of the leaf spring 456 may be selected so as to provide a relatively abrupt motion of the needle 442, needle carriage 446 and cannula 448 from the ready state (retracted position) of FIG. 14 to the insert state (extended position) of FIG. 15 and to also provide a relatively abrupt motion of the needle 442 from the insert state (extended position) of FIG. 15 to the needle retract state of FIG. 16. Also, the motion of the needle 442 may be relatively smooth and steady, by the action of the leaf spring and the guide structure 450. In that manner, trauma on the patient-user may be minimized. Alternatively, the spring tension may be selected and/or a motion damping mechanism may be provided to cause the needle 442 to move slowly toward the extended position (FIG. 15), to minimize trauma to other patients-users. Other embodiments described above with respect to FIGS. 4-13 may include similar guide structure for guiding the needle carriage in its motion.

Figure 17:
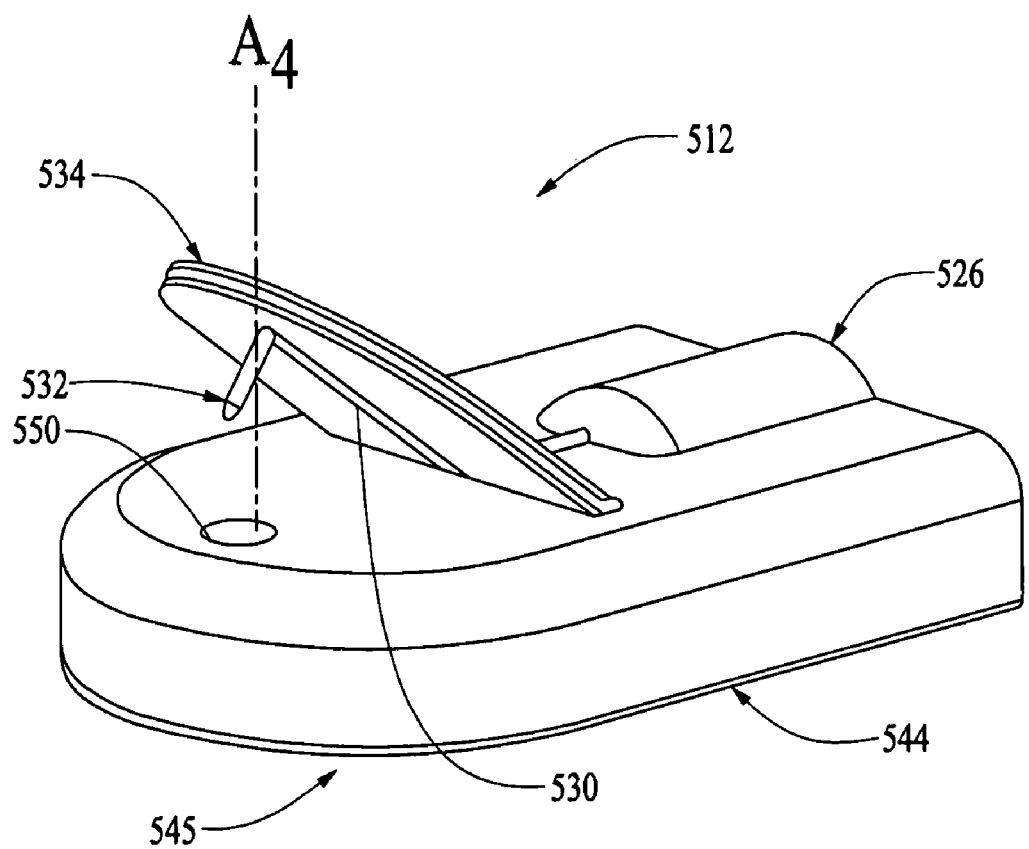
FIG. 17 is a side-perspective view of a portion of a delivery device having a needle inserter device according to a further embodiment of the present invention.
Figures 18, 19:
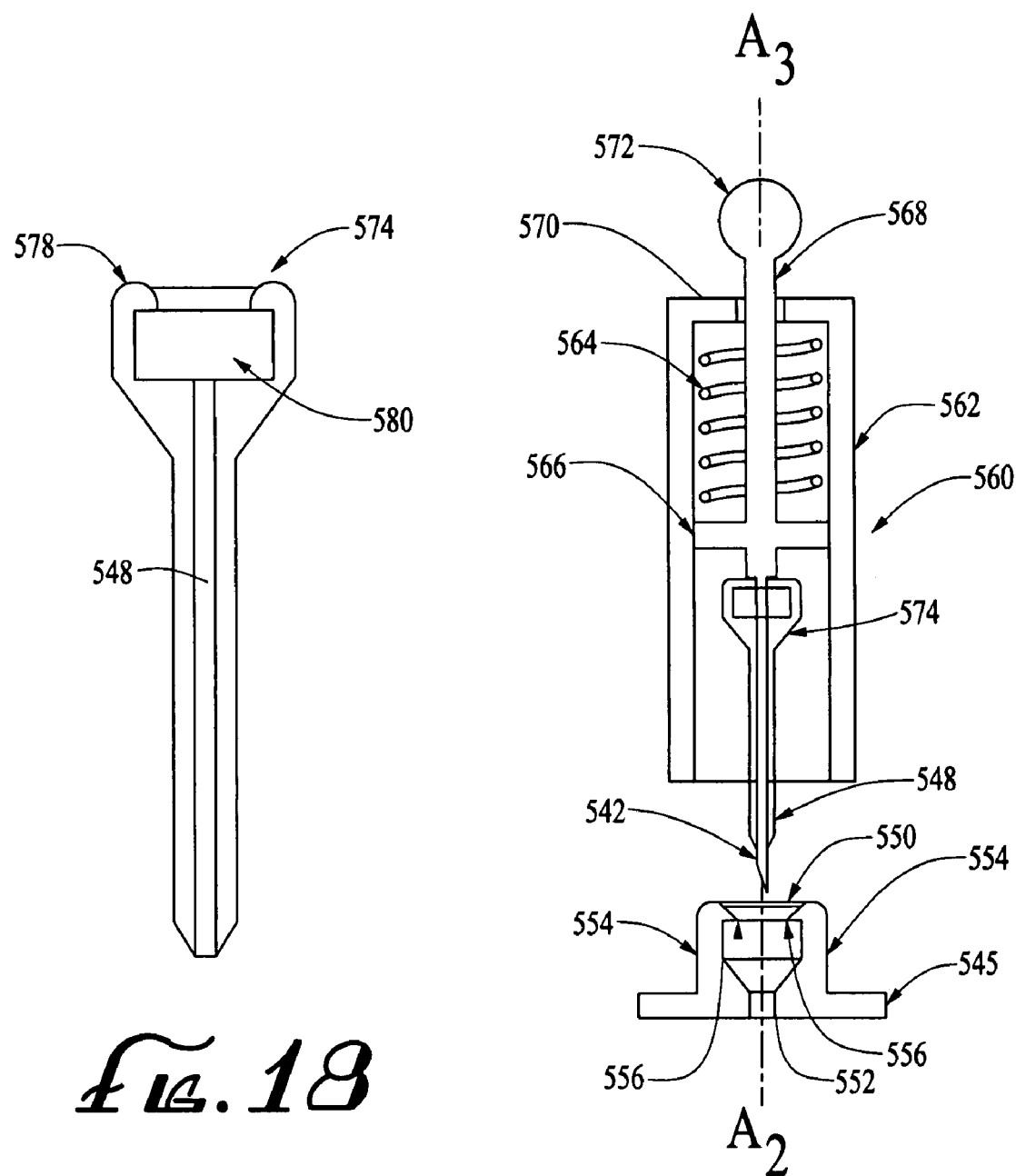
FIG. 18 is a schematic cross section view of a cannula and cannula nest component for use with the embodiment of FIG. 17.
FIG. 19 is a schematic cross-section view of an external needle injector having a cannula and cannula nest of FIG. 18 aligned for operation with a delivery device having a needle inserter of FIG. 17.

A further embodiment of a needle inserter device 512 is described with respect to FIGS. 17-19. The needle inserter device 512 (shown in FIG. 17) includes a housing portion 544, which may be similar in certain manners to the housing portion 44 described above with respect to FIGS. 4-6. However, the housing portion 544 includes a channel 550 that extends through skin-facing surface 545 of the housing portion base to a patient-user's skin, when the housing portion 544 is secured to a patient-user's skin as described above with respect to housing portion 44.

The channel 550 includes a cannula passage 552 that opens to the patient-user's skin, when the housing portion 544 is secured to a patient-user. The channel 550 also includes a suitable locking structure 554, for engaging a surface of a cannula nest and holding the cannula nest in place, as described below. The locking structure 554 may include, for example, one or more flexible or pivotal tabs arranged around the longitudinal axis $A_2$ of the channel 550 and passage 552, where each tab has a lip 556 that extends inward toward the axis $A_2$. Alternatively, other suitable locking structures, including, but not limited to, frictional fitted structures or the like, may be employed.

The needle inserter device 512 operates with an external needle injector 560 (shown in FIG. 19). The needle injector 560 operates to insert a needle 542 and cannula 548 into a patient-user's skin, through the channel 550 and then remove the needle 542, while leaving the cannula 548 in place. With the cannula 548 in the patient-user and extending at least partially into the channel 550, the cannula may be connected in fluid flow communication with a reservoir 528, as described below. The needle 542, cannula 548 and reservoir 528 may be similar in structure and function in certain manners to the needle 42, cannula 48 and reservoir 28, described above.

The needle injector 560 has a tubular body 562 with a hollow interior containing a coil spring 564 and a plunger head 566. A shaft 568 is fixed to and extends from the plunger head, along the longitudinal axis $A_3$ of the tubular body 562, and through an opening in an end wall 570 of the tubular body 562, to a location outside of the tubular body 562. A handle 572 may be provided on the outside end of the shaft 568. The coil spring 564 is arranged around the longitudinal axis $A_3$ of the tubular body 562 and has one end abutting the end wall 570 of the tubular body 562 and an opposite end abutting the plunger head 566.

The needle 542 is attached to the plunger head 566, opposite to the side of the plunger head that abuts the coil spring 564. The needle 542 extends along the direction of the longitudinal axis $A_3$ of the tubular body 562 and has a sharp end opposite to the end connected to the plunger head 566.

The cannula nest 574 may include a generally tubular body having a central channel 576, a first end 578 and a second end 579. The first end 578 has an end surface configured to engage the lip 556 of each locking structure tab 554, as described below. The second end 579 of the cannula nest 574 is formed integral with or otherwise connected in a fixed relation to the cannula 548, with the cannula in fluid flow communication with one end of the central channel 576 of the cannula nest 574. A sealable septum 580 is secured to the cannula nest 574, over and sealing the end of the central channel 576 opposite to the end that is connected to the cannula 548.

To operate, the housing structure 544 is secured to a patient-user's skin, with the surface 545 facing the patient-user's skin. A cannula nest 574 and cannula 548 assembly is attached to the needle 542 of the injector 560, by inserting the needle 542 through the septum 580 of the cannula nest and through the central channel 576 and cannula 548. Then the needle injector 560 is positioned adjacent the channel 550, with the axis $A_3$ of the injector body 562 generally aligned with the axis $A_2$ of the channel 550 as shown in FIG. 19. The patient-user (or other user) may pull back on the handle 572 of the injector, to cause the plunger head 566 to move toward the end wall 570 of the injector body 562 and compress the coil spring 564 between the plunger head 566 and the end wall 570.

The patient-user (or other user) may then release the handle and allow the coil spring to force the plunger head 566 in the direction away from the end wall 570 and, at the same time, push the needle 542 and cannula 548 through the channel 550 and into the patient-user's skin. The spring tension of the spring 564 is selected such that the motion of the plunger head 566 pushes the cannula nest 574 through the flexible or pivotal tabs 554 to a position at which the end surface 578 abuts against the lip 556 of each tab 554. As the cannula nest 574 is pushed through the tabs 554, the tabs 554 flex or pivot to allow the relatively wide portion of the cannula nest body to pass, before the tabs are allowed to flex or pivot back toward an unflexed or non-pivoted state at which the tab lips 556 engage the end surface 578 of the cannula nest and hold the cannula nest in place.

Upon the cannula nest 574 being locked into place by the tabs 554, the coil spring 564 has extended beyond its natural, un-tensioned length, as a result of the momentum of the plunger head motion. Accordingly, the coil spring 564 imparts a force on the plunger head 566 and needle 542, to cause the plunger head to move back toward the end wall 570 and withdraw the needle 542 from the cannula nest 574 and cannula 548. Alternatively, or in addition, the needle injector 560 may be manually moved in the axial direction $A_3$ away from the channel 550, to pull the needle 542 out of the cannula 548 and cannula nest 574. As the needle 542 withdraws from the septum 580 in the cannula nest 574, the septum 580 reseals itself, leaving the cannula in place in the patient-user's skin and in fluid flow communication with the interior of the channel 550.

Thereafter, the reservoir 528 may be connected in fluid flow communication with the channel 550, to allow fluid delivery from the reservoir 528, to the patient-user, though the cannula 548. The reservoir 528 may be supported by the housing structure 544 and may be operatively coupled to a drive device for driving the infusion medium from the reservoir 528 into a conduit 530. The conduit 530 may include any suitable tubing structure or passage having a fluid flow channel connected in fluid flow communication with the interior of the reservoir 528, for conveying fluid from the reservoir 528. For example, the conduit 530 may include a flexible, plastic tubing.

The conduit 530 is also provided in fluid flow communication with a hollow needle 532. The hollow needle 532 and a portion of the conduit 530 may be supported on a cover member 534 that is pivotally connected to the housing structure 544. The cover member 534 may be pivotal, relative to the housing structure 544, to a first position at which the channel 550 is exposed for operation with a needle injector 560, as described above, and to a second position to cover the channel 550. The hollow needle 532 may be positioned on the cover member 534 at a location at which the sharp end of the needle extends into the channel 544, when the cover member 534 is pivoted to the second position over and covering the channel 550. Accordingly, a patient-user (or other user) may cause the hollow needle 532 to pierce and pass through the septum 580 on a cannula nest structure located within the channel 550, to connect the reservoir 528 in fluid flow communication with the cannula nest structure and cannula 548.

A further embodiment of a needle inserter device 612 is described with respect to FIGS. 20-23. The needle inserter device 612 (shown in FIG. 20) includes a base portion 644, which may be arranged within a disposable housing portion 20 (shown in FIGS. 2 and 3). In other embodiments, the needle inserter device 612 may be located in the durable housing portion 22 or in an injection site module connected to the disposable housing portion 20 or the durable housing portion 22, as described herein. Alternatively, the needle inserter device 612 may be included in other systems that operate by inserting a needle into a subject or object.

Figure 20:
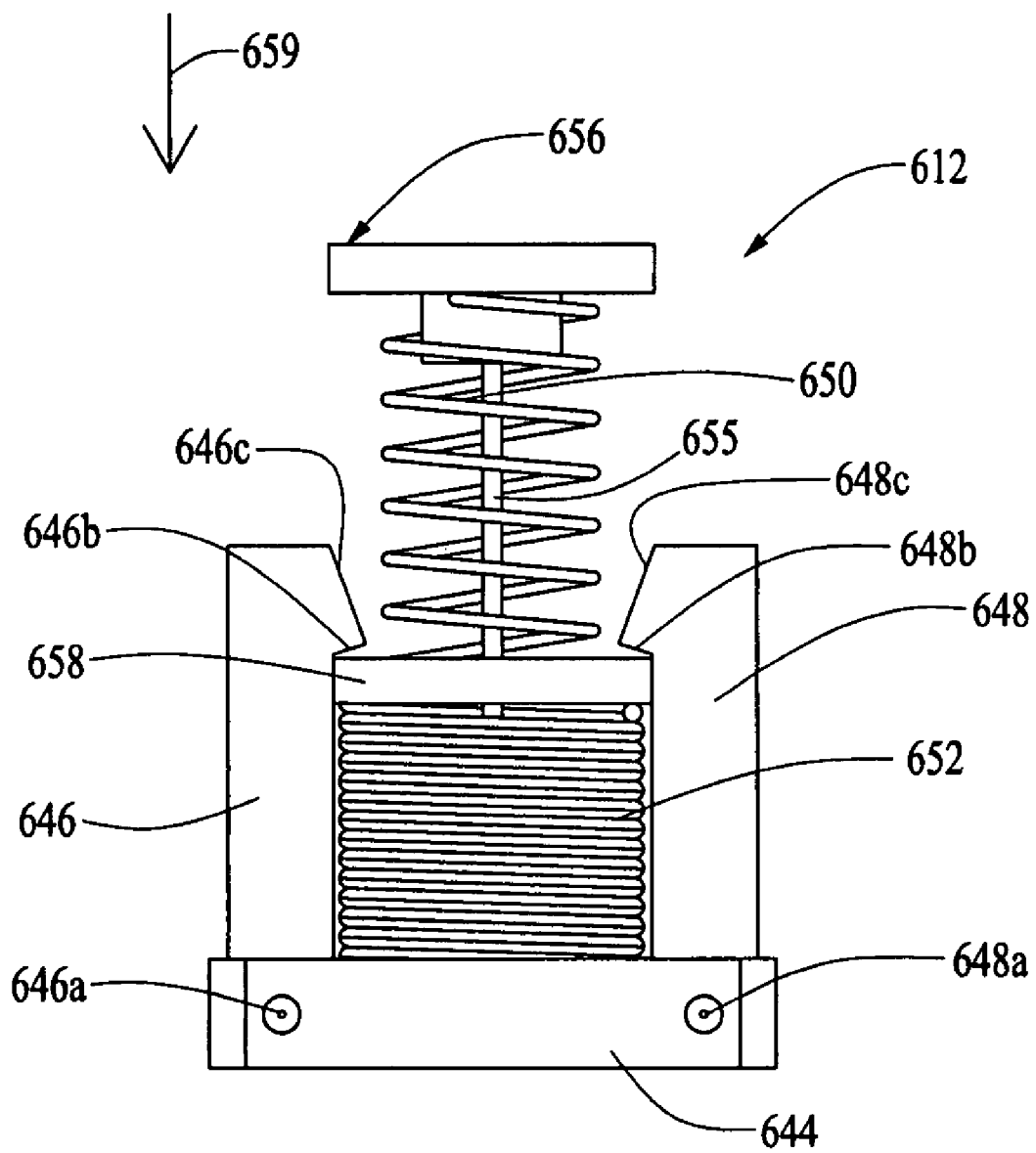
FIGS. 20-23, each show a side view of a needle inserter device according to a further embodiment, in various positions.
Figure 21:
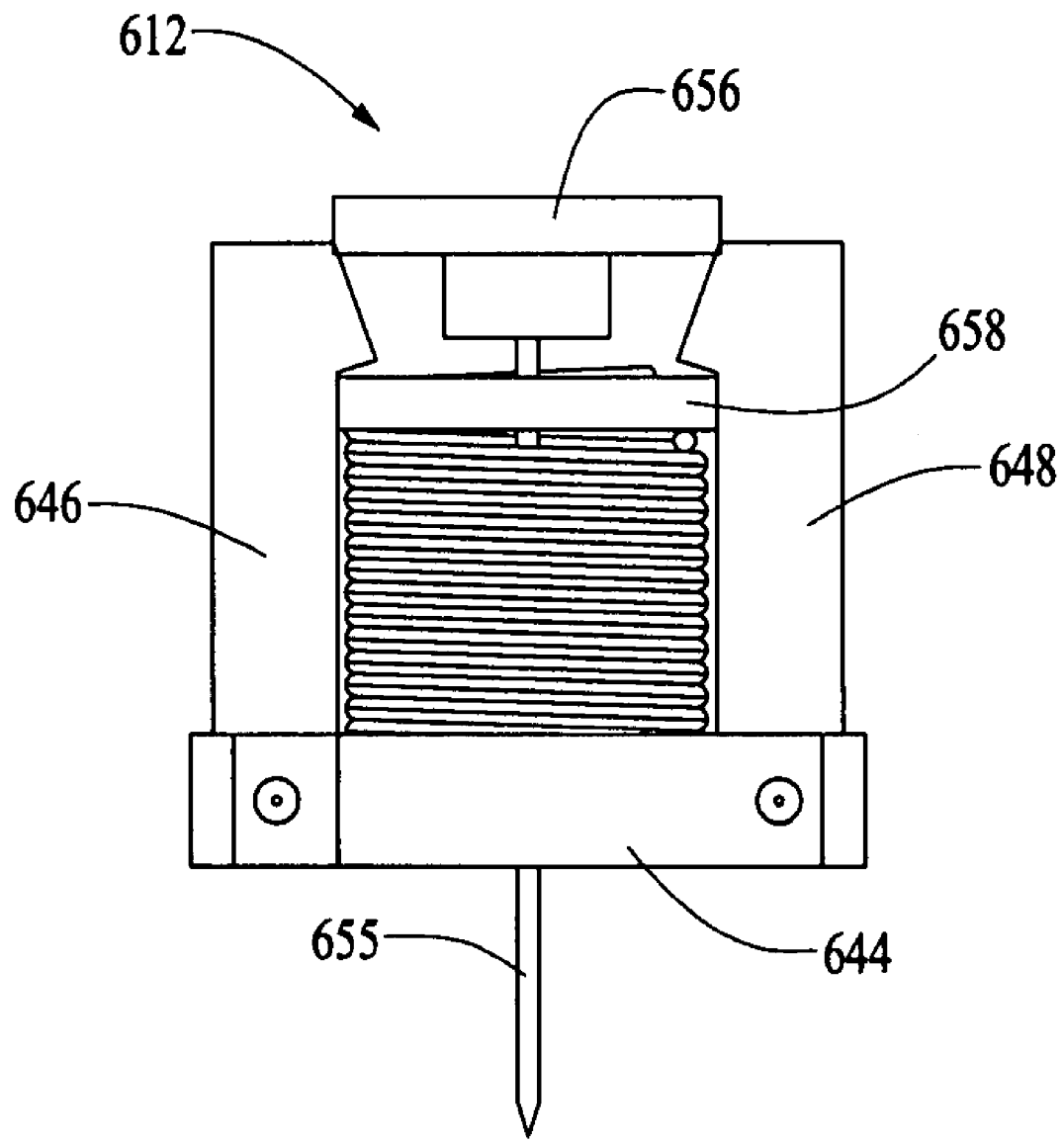
Figure 22:
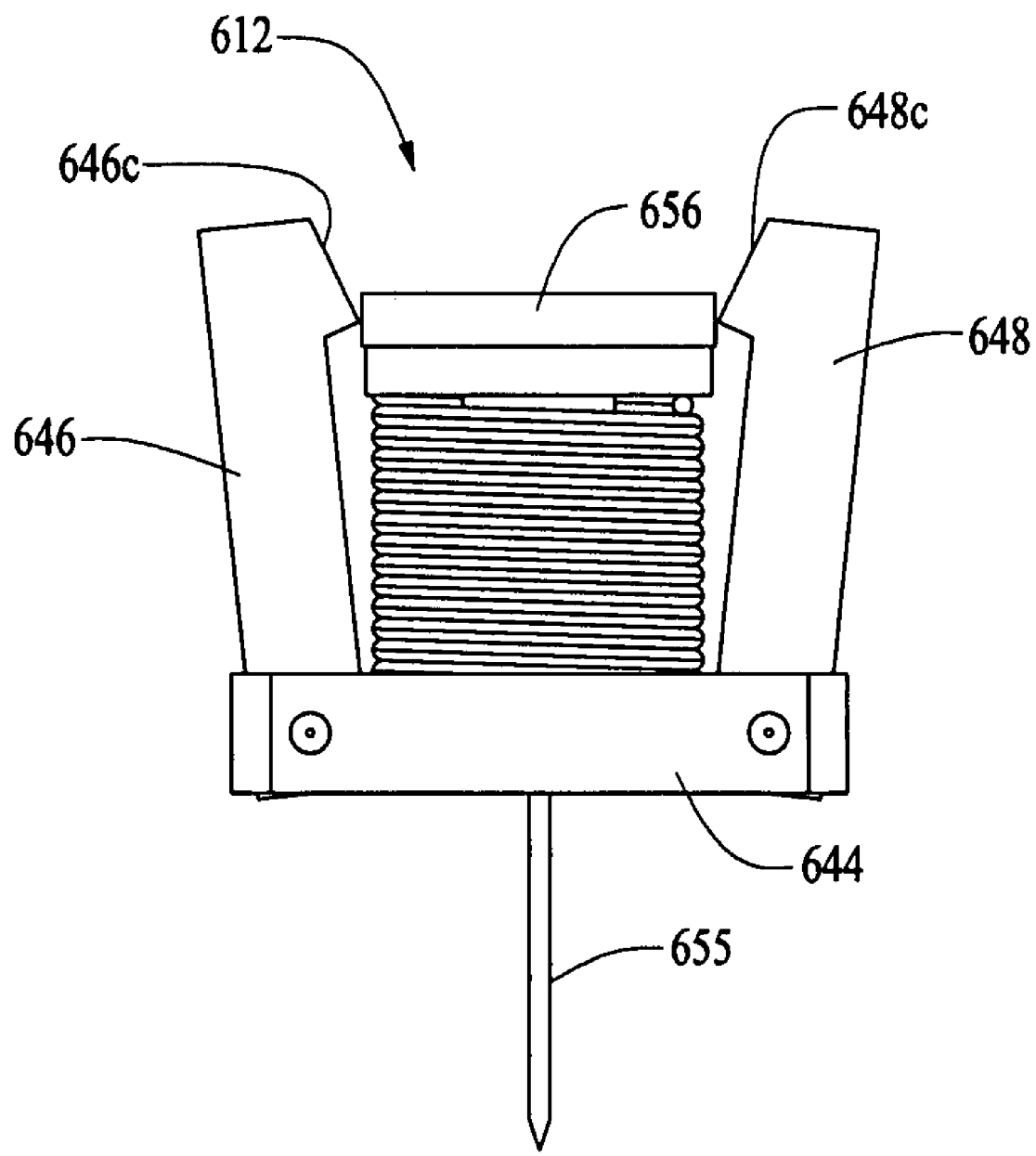

The base 644 may include a generally rigid support structure having an aperture or opening, through which a needle and a cannula may extend, as shown in FIGS. 21 and 22. The base 64 supports a pair of pivotal arms 646 and 648, for pivotal motion about a respective pair of pivot axis 646a and 648a. A suitable hinge or pivot axle may be provided to connect the pivotal arms 646 and 648 to the base 644. The base 644 and the pivotal arms may be made of any suitably rigid materials, including, but not limited to metal, plastic, ceramic, composite material or the like. While the embodiment in FIGS. 20-23 includes two pivotal arms 646 and 648, other embodiments may include no more than one pivotal arm or more than two pivotal arms connected to the base 644 at respective pivot axes.

The base 644 supports a pair of coil springs 650 and 652. The coil spring 650 is arranged to function as an insertion spring, while the coil spring 652 is arranged to function as a retraction spring. Each coil spring 650, 652 has a coil wire member that is spirally wound around an open coil interior. The open coil interiors of the coil springs 650 and 652 are arranged coaxially and are aligned with the needle or cannula opening in the base 644. A needle 654 is supported by the insertion spring 650. The needle 654 includes a needle shaft 655 and a needle head 656. The insertion spring 650 has one end that abuts the needle head 656 and a second end that abuts the base 644. A hollow cannula (not shown in FIGS. 20-23) may be arranged around the shaft 655 of the needle.

The retraction spring 652 has one end that abuts a flange member 658 and a second end that abuts the base 644. In a starting position, the retraction spring 652 is arranged in a compressed state, between the flange member 658 and the base 644, as shown in FIG. 20. The pivotal arms 646, 648 may include a stop surface, such as projecting surfaces 646b and 648b, for engaging the flange member 658, to hold the flange member 658 in place against the force of the compressed retraction spring 652, when the pivotal arms 646 and 648 are in a locking position as shown in FIG. 20.

While the pivotal arms 646 and 648 are in the locking position to hold the flange member 658 and retraction spring 652 in place, a manual (or automated) force may be applied to the needle head 656 (in the direction of arrow 659), to move the needle 654 against the force of the insertion spring 650. By applying a force on the needle head 656 in the direction of arrow 658, the needle 654 and a cannula on the needle shaft 655 may be moved toward an insertion position as shown in FIG. 22, at which the insertion spring 650 is compressed between the needle head 656 and the base 644. As the needle 654 and cannula move from the position shown in FIG. 20 toward the position shown in FIG. 22, the needle 654 first reaches a partially extended position shown in FIG. 21.

In the partially extended position shown in FIG. 21, the sharp end of the needle 656 and at least a portion of the cannula around the needle shaft 655 are extended through the opening in the base 644, to the position shown in FIG. 21. Further force on the needle head 656 causes the needle and cannula to continue to move in the direction of arrow 658, to the fully extended position shown in FIG. 22. The cannula (not shown in FIGS. 21-23) may be supported on a carriage, similar to the carriage 46 or 146 described above and may engage a locking mechanism, such as but not limited to, pawls 60 or 160 described above, when in the fully extended position of FIG. 22. In addition, the cannula (not shown in FIGS. 21-23) may be connected in fluid flow communication with a reservoir, when in the fully extended position, for example, but not limited to, the fluid flow connection structure described above with respect to the cannula 48 or 148 and the reservoir 28. To simplify the present disclosure, reference is made to the description of the cannula locking structure and fluid flow connection to the reservoir 28 of the embodiments in FIGS. 4-8. By supporting the base 644 at an injection site (either in the disposable housing portion 20, the durable housing portion 22 or an injection site module), the base 644 may be arranged adjacent a patient-user's skin (for example, when the disposable housing portion 20, the durable housing portion 22 or the injection site module is arranged adjacent the patient-user's skin, as described above), to allow the sharp end of the needle 654 to pierce the patient-user's skin and to allow the cannula around the needle shaft to be inserted at least partially into the patient-user's skin, when the needle is in the fully extended position of FIG. 22.

Once the needle 654 and cannula are in the partially extended position of FIG. 21, further movement of the needle 654 in the direction of arrow 658 to the position shown in FIG. 22 causes the needle head 656 to engage the pivotal arms 646 and 648 and pivot the arms 646 and 648 to an unlocked position as shown in FIG. 22. The pivotal arms 646 and 648 may have angled surfaces 646c and 648c, respectively, for engaging needle head 656, to more efficiently transfer the linear motion of the needle head 656 to pivotal motion of the arms 646 and 648, as the needle head 656 engages and moves along the angled surfaces 656c and 648c in the direction of arrow 658.

Figure 23:
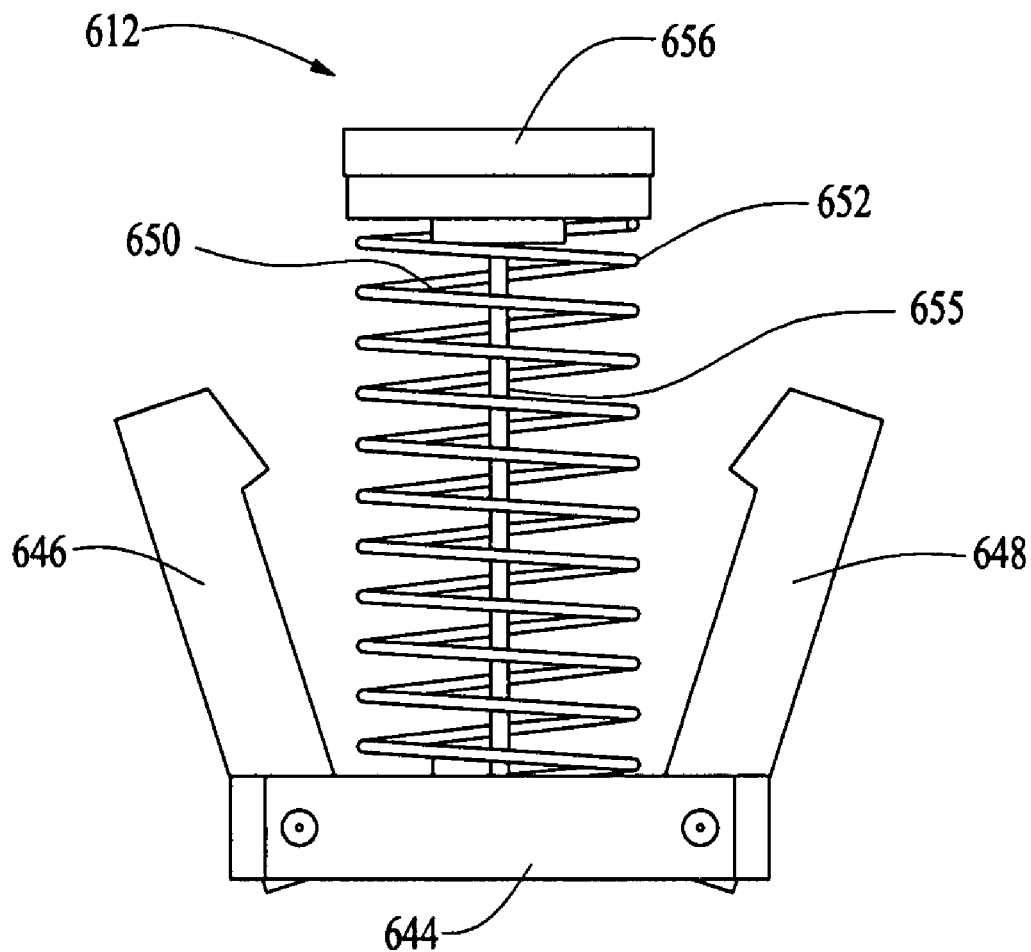

In the unlocked position of the arms 646 and 648, the flange 658 is no longer held in place by the arms 646 and 648 against the force of the retraction spring 652. Accordingly, when the arms 646 and 648 are moved into the unlocked position, the retraction spring 652 forces the flange member 658 against the needle head 656 and forces the needle 654 to move in the direction opposite to the direction of arrow 658, to a retracted position, as shown in FIG. 23. However, the cannula is left in place, extending into the patient-user's skin, similar to the function of the cannula 48 or 148 in the embodiments of FIGS. 4-8. Accordingly, the insertion device shown in FIGS. 21-23 may be employed to insert a needle and cannula into a patient-user's skin and withdraw the needle, leaving the cannula in place.

Figure 24:
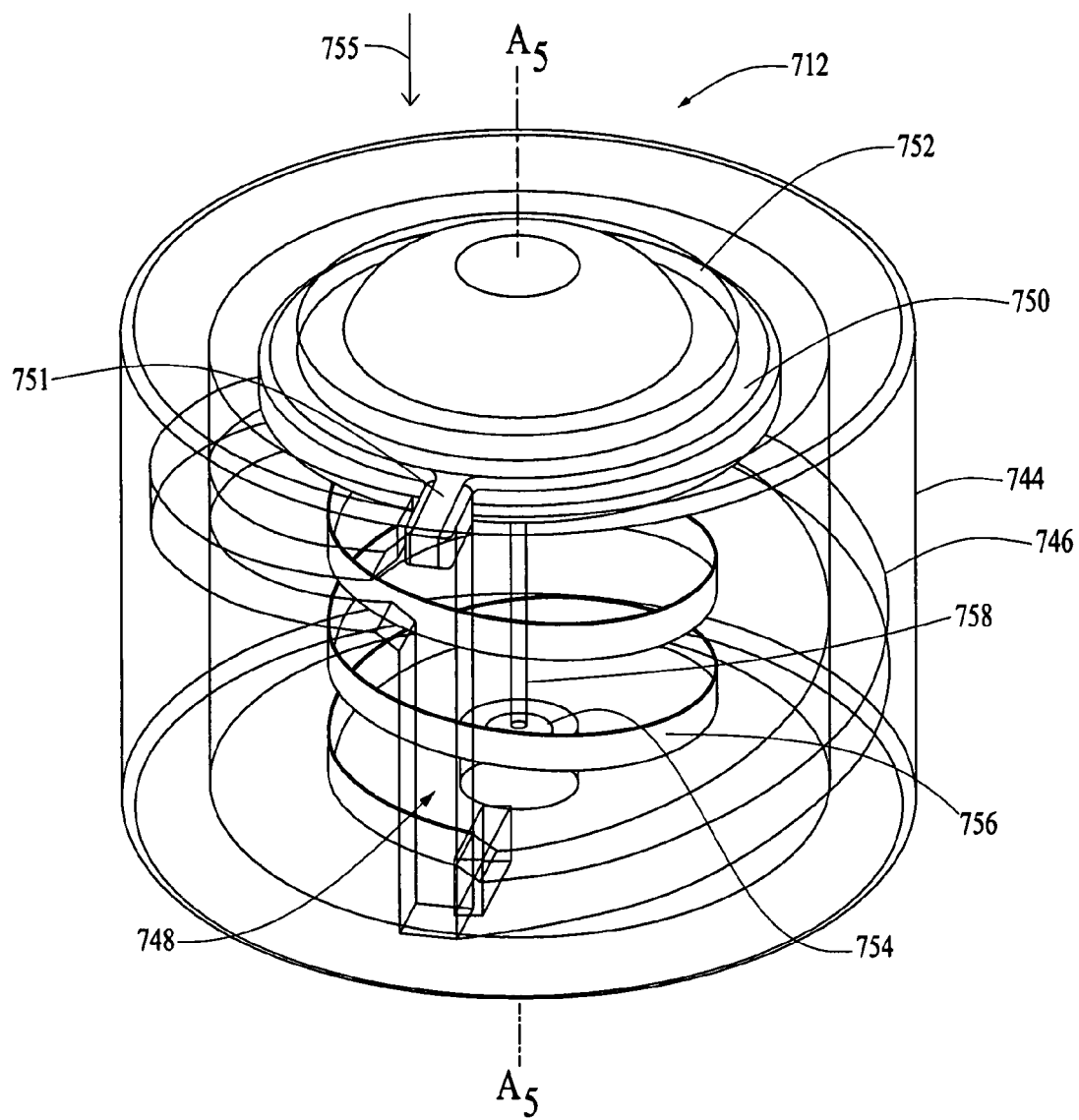
FIGS. 24 and 25 show a perspective view of a needle inserter device according to a further embodiment, in a retracted or start position and in an extended position, respectively.
Figure 25:
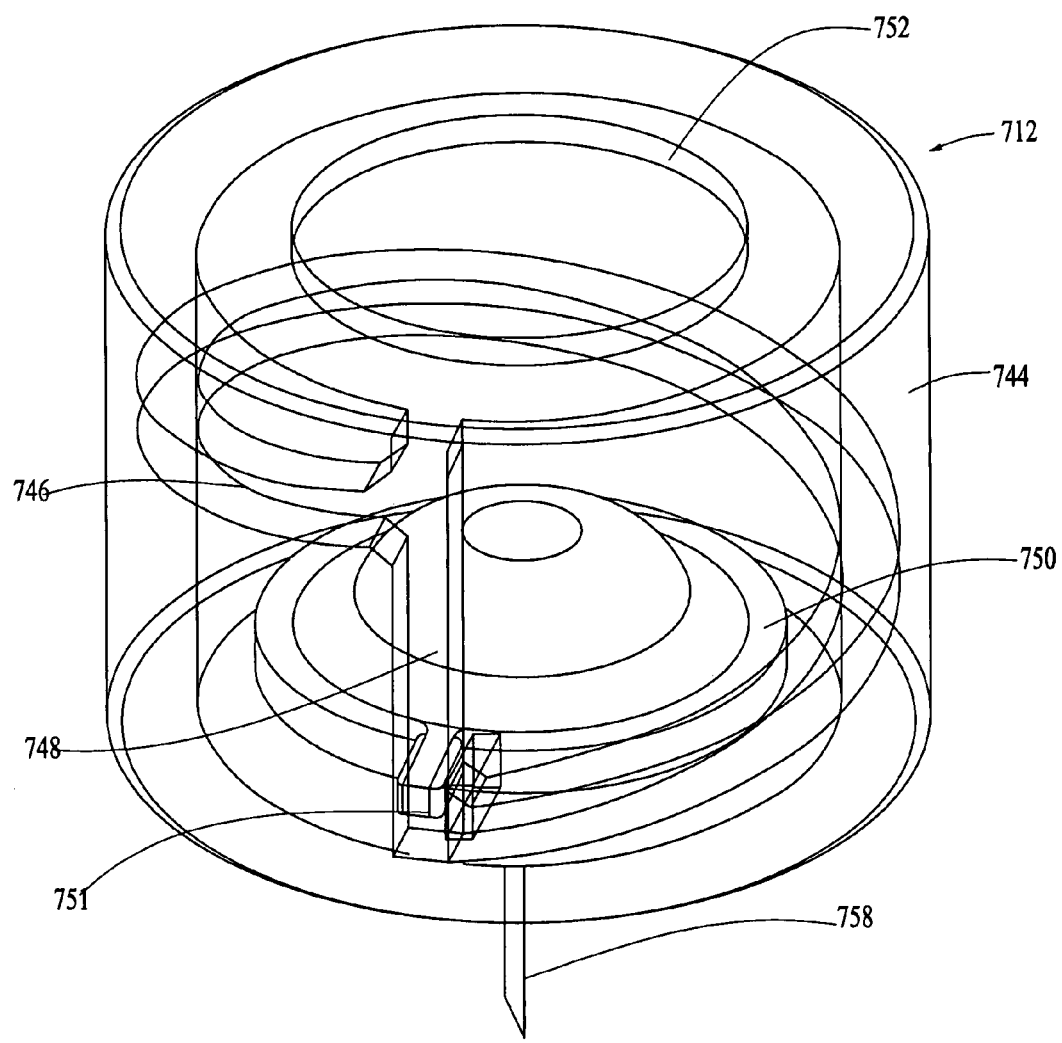

A further embodiment of a needle inserter device 712 is described with respect to FIGS. 24-25. In FIG. 24, the needle inserter device 712 is in a retracted or starting position. In FIG. 25, the needle inserter device 712 is in an extended position. The needle inserter device 712 (shown in FIG. 24) includes a housing portion 744, which may be arranged within a disposable housing portion 20 (shown in FIGS. 2 and 3).

In other embodiments, the needle inserter device 712 may be located in the durable housing portion 22 or in an injection site module connected to the disposable housing portion 20 or the durable housing portion 22, as described herein. Alternatively, the needle inserter device 712 may be included in other systems that operate by inserting a needle into a subject or object. The housing 744 may include a rigid, generally cylindrical or disc-shaped body, having a hollow, generally cylindrical interior and a longitudinal dimension along the axis $A_3$ of the generally cylindrical shape of the body. The interior surface of the housing 744 has a spiral groove 746 that starts near, but spaced from, the top of the housing 744 (relative to the orientation shown in FIG. 24) and extends around the inner peripheral wall of the housing 744, to a location near the base of the housing 744. A further, linear groove 748 is provided at the base end of the spiral groove and extends toward the top end of the housing (relative to the orientation shown in FIG. 24). The linear groove connects the base end of the spiral groove with the top end of the spiral groove 746 and extends a short distance above the top end of the spiral groove 746.

A cam member 750 is located within the interior of the housing 744 and has a projection 751 that is arranged to extend into the grooves 746 and 748. The housing 744 includes an opening 752 on one end (the top end in the orientation of FIG. 24), through which the cam member 750 may be operated by manual or automated force. A surface of the cam member 750 may be exposed through the opening 752. That exposed surface of the cam member 750 may include a convex-shape, that extends into or partially through the opening 752, when the cam member 750 is in a retracted position, as shown in FIG. 24. The housing 744 also includes a needle opening 754 through the base of the housing 744, through which a needle and cannula may be extended, as described below.

The cam member 750 is supported within the interior of the housing 744 by a coil spring 754. The coil spring 756 extends between the cam member 750 and the base of the housing 744 and has one end secured to (or adjacent to) the base portion of the housing 744 and another end secured to the cam member 750.

In the starting or retracted position of FIG. 24, the coil spring 754 is partially unwound against its natural wound state, such that the spring 746 imparts a force on the cam member 750, in the winding direction of the spring. However, because the projection 751 of the cam member 750 is located within the groove 748, the spring 746 is held in the partially unwound state, against the natural winding force of the spring 756.

From the retracted position shown in FIG. 24, a manual or automated force may be applied to the cam member 750, through the opening 752 in the housing 744, to force the cam member to move in the axial direction $A_5$, along the direction of arrow 755 and partially compress the coil spring against the natural compression force of the spring, until the cam projection 751 moves along the linear groove 748, toward the base of the housing 744 to align with the top end (relative to the orientation of FIG. 24) of the spiral groove 746. Once the cam projection 751 is aligned with the spiral groove 746, the natural winding force of the spring 756 causes the cam member 750 to rotate and move toward the base of the housing 744, while the cam projection 751 follows the spiral groove 746, as the spring winds toward its natural, untensioned state of winding. However, as the cam member 750 moves toward the base of the housing 744, the cam member 750 compresses the spring 756 against its natural longitudinal dimension (in the dimension from the of the axis $A_3$).

As the cam member 750 moves toward the base of the housing 744, a needle 758 is moved through the opening 754 in the base of the housing 744, to the extended position (shown in FIG. 25). The needle 758 is secured to a surface of the cam member that faces the base, so as to move with the base from the start or retracted position of the cam member 750 and needle 758 (shown in FIG. 24) to the extended position of the cam member 750 and needle 758 (shown in FIG. 25). A cannula may be supported on the shaft of the needle 758, adjacent the sharp end of the needle.

By supporting the base of the housing 744 at an injection site (either in the disposable housing portion 20, the durable housing portion 22 or an injection site module), the housing 744 may be arranged adjacent a patient-user's skin (for example, when the disposable housing portion 20, the durable housing portion 22 or the injection site module is arranged adjacent the patient-user's skin, as described above), to allow the sharp end of the needle 758 to pierce the patient-user's skin and to allow the cannula around the needle shaft to be inserted at least partially into the patient-user's skin, when the needle is in the extended position of FIG. 25.

Once the needle 758 and cannula are in the extended position of FIG. 25, the cam projection 751 (which had followed the spiral path of the groove 746) is aligned with the linear groove 748. At that position, the spring 756 is extended in the longitudinal dimension of axis $A_5$ beyond its natural longitudinal state. Accordingly, the spring 756 provides a force on the cam member 750, to move the cam member 750 in the axial dimension $A_5$, in the direction opposite to the direction of arrow 755, while the projection 751 follows the linear groove 748, to the retracted position of FIG. 24. The cannula (not shown in FIGS. 24-25) may be supported on a carriage, similar to the carriage 46 or 146 described above and may engage a locking mechanism, such as but not limited to, pawls 60 or 160 described above, when in the fully extended position of FIG. 25. In addition, the cannula (not shown in FIGS. 24-25) may be connected in fluid flow communication with a reservoir, when in the fully extended position, for example, but not limited to, the fluid flow connection structure described above with respect to the cannula 48 or 148 and the reservoir 28. To simplify the present disclosure, reference is made to the description of the cannula locking structure and fluid flow connection to the reservoir 28 of the embodiments in FIGS. 4-8. Accordingly, as the cam member 750 moves toward the retracted position, the needle 756 is retracted from the patient-user, but the cannula remains in the patient-user. Accordingly, the insertion device shown in FIGS. 24 and 25 may be employed to insert a needle and cannula into a patient-user's skin and withdraw the needle, leaving the cannula in place.

Figure 26:
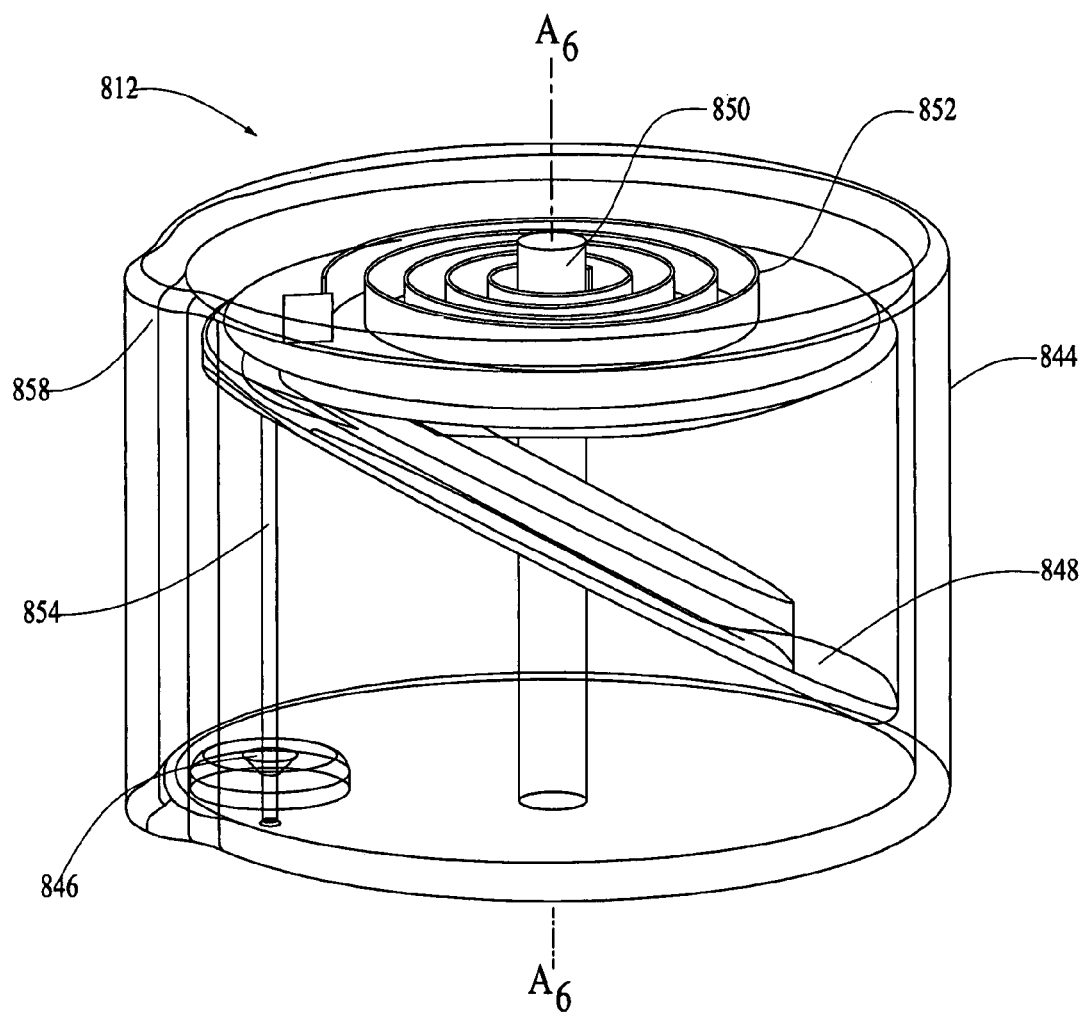
FIGS. 26 and 27 show a perspective view of a needle inserter device according to a further embodiment, in a retracted or start position and in an extended position, respectively.
Figure 27:
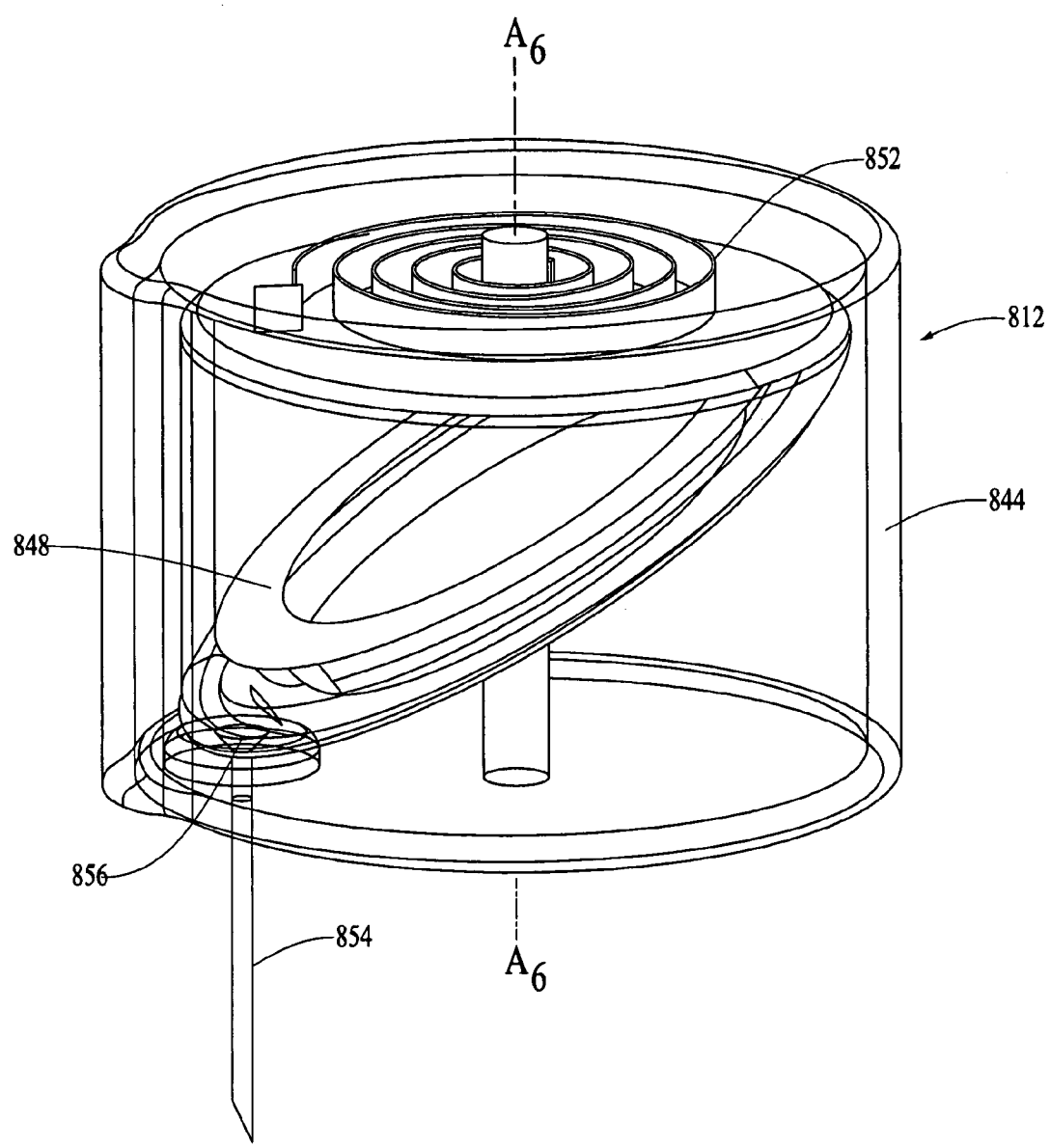

A further embodiment of a needle inserter device 812 is described with respect to FIGS. 26-27. In FIG. 26, the needle inserter device 812 is in a retracted or starting position. In FIG. 27, the needle inserter device 812 is in an extended position. The needle inserter device 812 includes a housing 844 that is similar to the housing 744 described above with respect to FIGS. 24 and 25. However, the housing 844 has a needle aperture or opening 846 that is off-center, relative to the axis of the generally cylindrical shape of the housing 844. The needle inserter 812 in FIGS. 26 and 27 includes a rotary disc 848, supported for rotation by an axle 850, at an obtuse angle relative to the axial dimension $A_4$, within the interior of the housing 844. A coil spring 852 in the form of a coiled wire or ribbon is supported within the housing 844 and has one wire or ribbon end fixed with respect to the housing 844 and a second wire or ribbon end secured to and fixed with respect to an off-center location of the disc 848.

A needle 854 is supported within the housing 844, in alignment with the needle opening 846. The needle 854 has a needle head 856 arranged to abut a surface of the disc 848, as the disc 848 rotates about the axis $A_4$. In one embodiment, a coil spring (not shown in FIGS. 26 and 27) is provided between the needle head 856 and the base of the housing 844, to bias the needle in toward the retracted position of FIG. 26. The needle head 856 may fit within a groove or shaped channel 858 provided in the housing 844. The groove or channel 858 extends in the longitudinal direction, parallel to the axis $A_4$.

When the disc 848 and needle 854 are in the starting position of FIG. 26, the coil spring 852 is partially uncoiled (or coiled) against its natural spring force. The disc 848 may be held in the starting position by a manually operable lever or other suitable mechanism that may be release by manual operation. Once released, the coil spring 848 partially coils (or uncoils) under its own spring tension and rotates the disc 848 about the axis $A_4$. Because the disc 848 is supported at an angle relative to the axis $A_4$, rotation of the disc 848 forces the needle head 856 in the direction toward the base of the housing 844 and, thus moves the needle 854 toward the extended position shown in FIG. 27.

By supporting the base of the housing 844 at an injection site (either in the disposable housing portion 20, the durable housing portion 22 or an injection site module), the housing 844 may be arranged adjacent a patient-user's skin (for example, when the disposable housing portion 20, the durable housing portion 22 or the injection site module is arranged adjacent the patient-user's skin, as described above), to allow the sharp end of the needle 854 to pierce the patient-user's skin and to allow a cannula around the needle shaft to be inserted at least partially into the patient-user's skin, when the needle is in the extended position of FIG. 27. The cannula (not shown in FIGS. 26-27) may be supported on a carriage, similar to the carriage 46 or 146 described above and may engage a locking mechanism, such as but not limited to, pawls 60 or 160 described above, when in the fully extended position of FIG. 27. In addition, the cannula (not shown in FIGS. 26-27) may be connected in fluid flow communication with a reservoir, when in the fully extended position, for example, but not limited to, the fluid flow connection structure described above with respect to the cannula 48 or 148 and the reservoir 28. To simplify the present disclosure, reference is made to the description of the cannula locking structure and fluid flow connection to the reservoir 28 of the embodiments in FIGS. 4-8.

Once the disc 848 and needle 854 are in the extended position of FIG. 27, further rotation of the disc 848 allows the needle 854 to be retracted back toward the retracted or starting position shown in FIG. 26, while leaving the cannula in place at least partially within the patient-user's skin. Retraction of the needle 854 may be provided, for example, by the force of a coil spring or other suitable bias mechanism, as described above. Accordingly, the insertion device shown in FIGS. 26 and 27 is another example of a structure that may be employed to insert a needle and cannula into a patient-user's skin and withdraw the needle, leaving the cannula in place. Alternatively, or in addition, the needle head may be connected to, but ride within an annular groove within the disc 848 so as to be pulled back by the disc into a retracted position, as the disc 848 completes a full 360 degree rotation.

Figure 28:
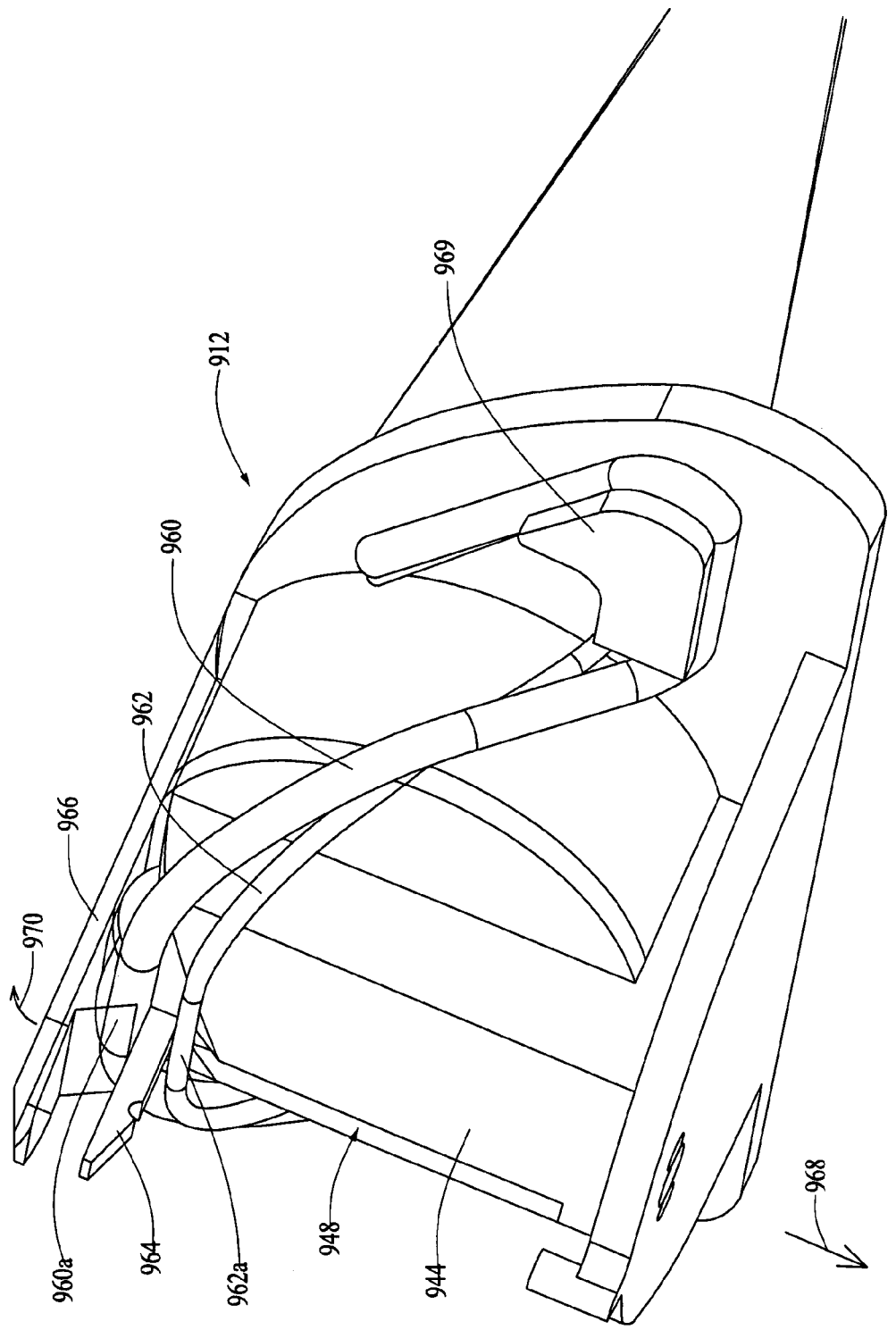
FIGS. 28 and 30 each show a perspective view of a needle inserter device according to a further embodiment, in various positions.
Figure 29:
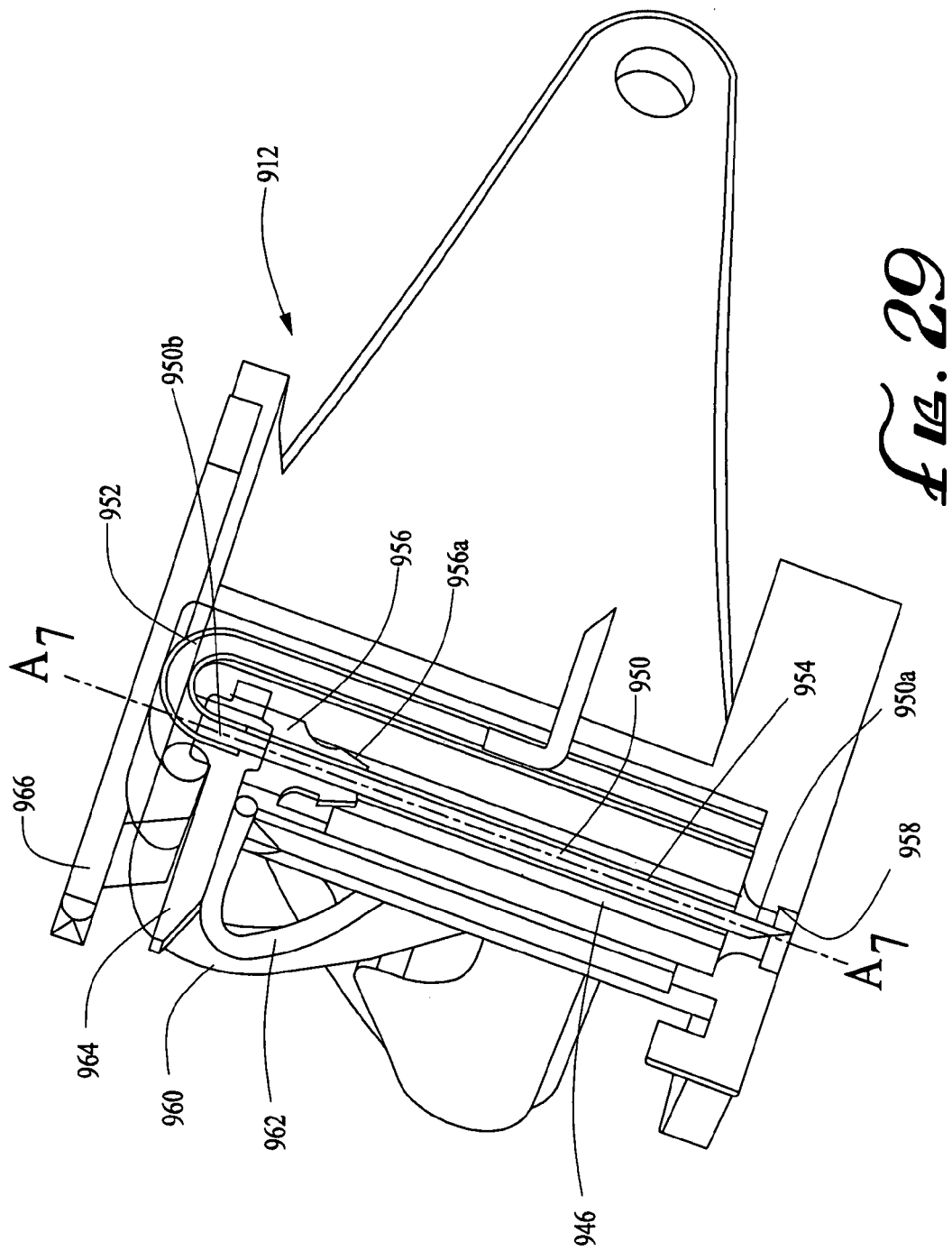
FIGS. 29 and 31 each show a cross-sectional view of the needle inserter device according FIGS. 28 and 30, respectively.
Figure 30:
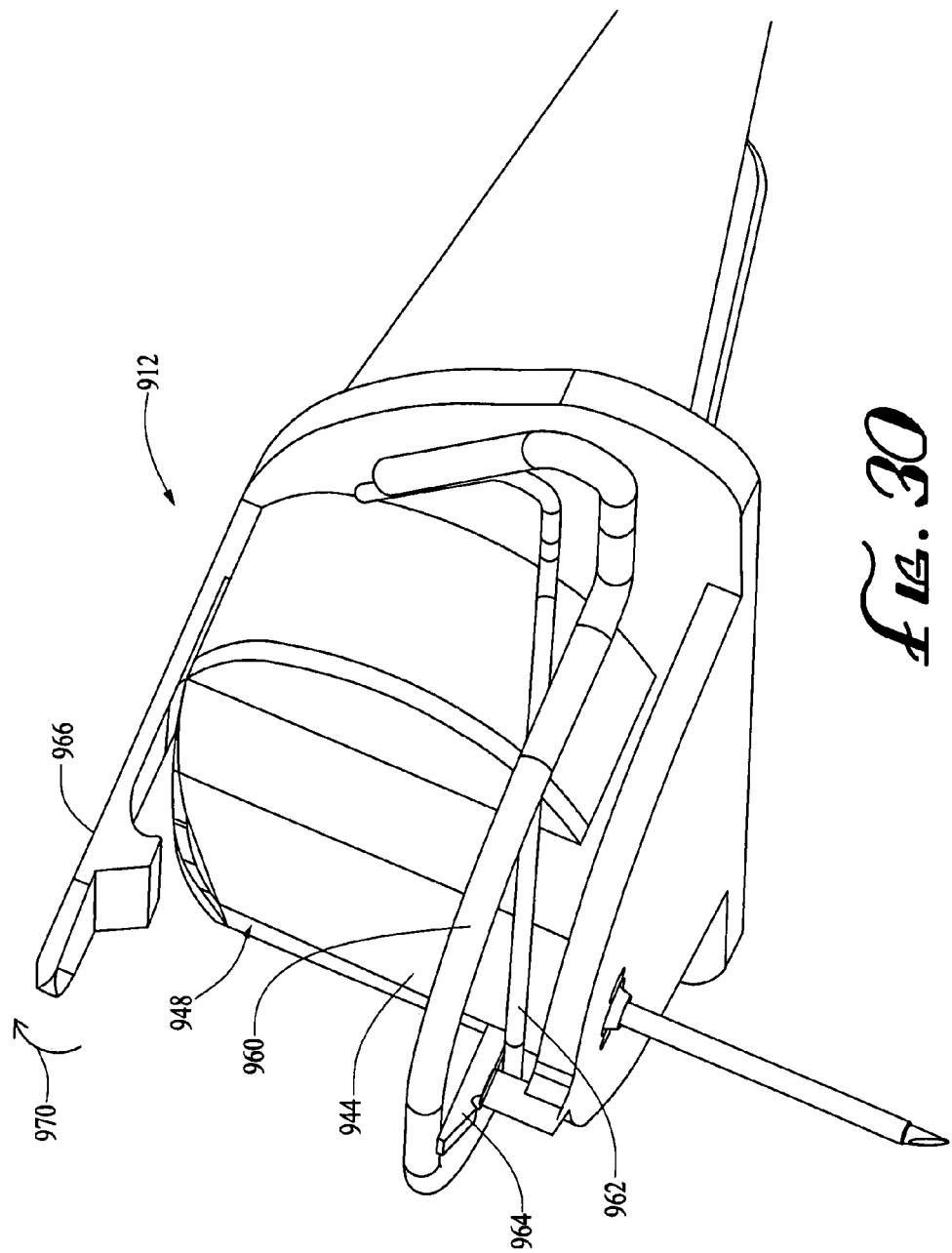
Figure 31:
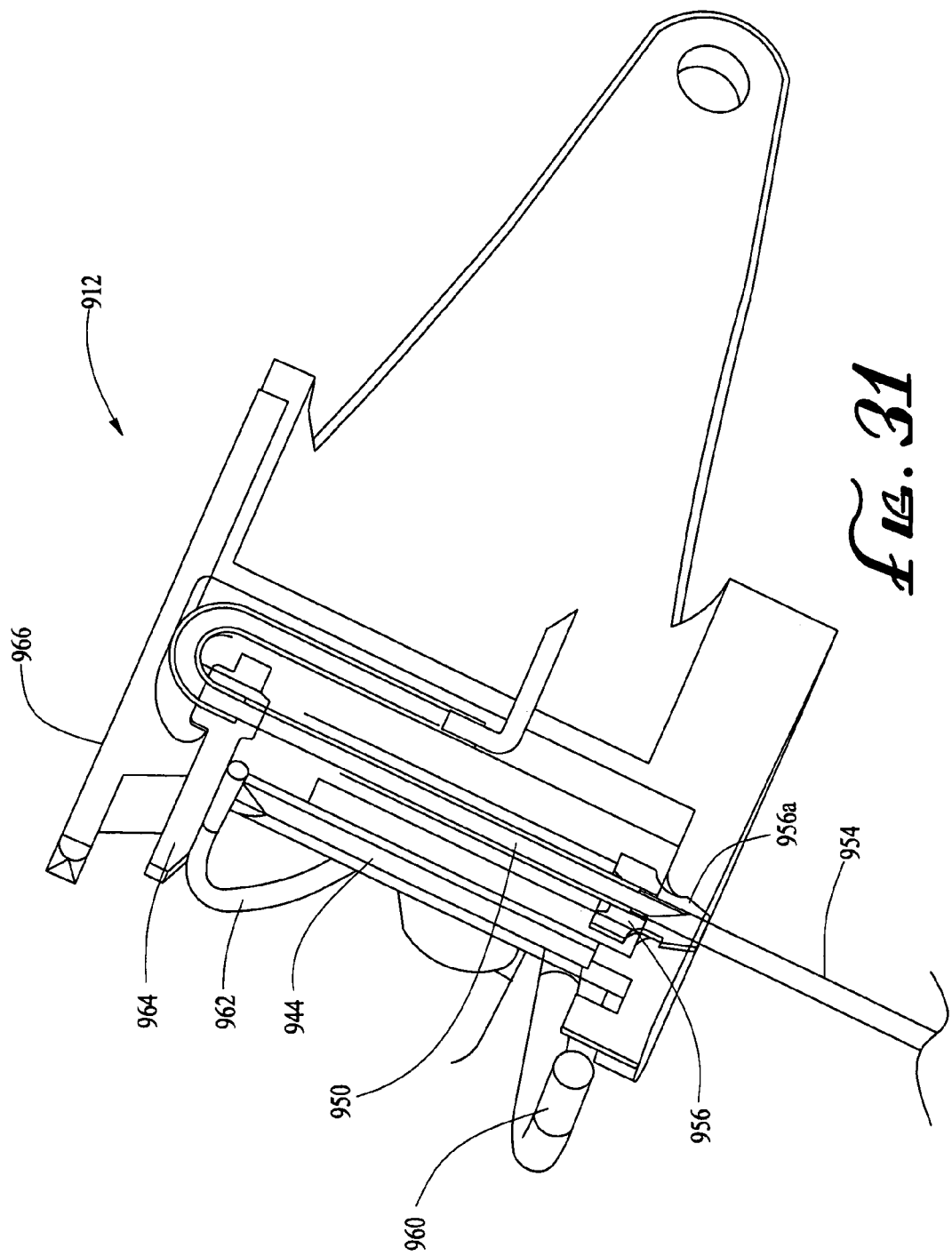

A further embodiment of a needle inserter device 912 is described with respect to FIGS. 28-31. FIGS. 28 and 29, show an external perspective view and a cross-sectional view, respectively, of the needle inserter device 912, with a needle and cannula in a retracted or starting position. In FIG. 30, the needle inserter device 912 is shown, with the needle and cannula in an extended position. In FIG. 31, the needle inserter device 912 is shown in a cross-sectional view, with the needle in a retracted position and the cannula in an extended position and connected in fluid-flow communication with a fluid conduit.

More specifically, the needle inserter device 912 includes a housing portion 944, which may be arranged within a disposable housing portion 20 (shown in FIGS. 2 and 3). In other embodiments, the needle inserter device 912 may be located in the durable housing portion 22 or in an injection site module connected to the disposable housing portion 20 or the durable housing portion 22, as described herein. Alternatively, the needle inserter device 912 may be included in other systems that operate by inserting a needle into a subject or object.

The housing 944 includes a rigid body that has an interior channel 946 with a longitudinal dimension along the axis $A_4$. The housing 944 may be made of any suitably rigid material, including, but not limited to metal, plastic, ceramic, composite material or the like. The housing 944 also has a slot-shaped opening 948 that is open to the interior channel 946 and extends along at least a portion of the length of the interior channel 946, in the longitudinal dimension of the axis $A_4$. A hollow needle 950 is supported within the channel 946 for movement relative to the housing 944, between a retracted or start position (shown in FIGS. 28 and 29), to an extended position (shown in FIG. 30), and back to a retracted position (shown in FIG. 31). The needle 950 may be made of any suitable material, including, but not limited to metal, plastic, ceramic, glass, composite material or the like.

The hollow needle 950 has a hollow interior and a sharp end 950a provided with an opening into the hollow needle interior. The hollow needle 950 also has a second end 950b that has another opening into the hollow needle interior. A flexible fluid-flow conduit 952 is connected in fluid-flow communication with the open second end 950b of the needle 950. The flexible conduit 952 is also connected (at another end, not shown in FIG. 29) to an infusion fluid reservoir, such as a reservoir in the disposable housing portion 20 as described above, or another suitable reservoir, to connect a source of infusion fluid to the hollow needle. The conduit 952 may be flexible, to flex and move with the motion of the needle 950, as the needle 950 moves between a retracted or start position and an extended position.

A cannula 954 having a cannula nest 956 is supported on the needle 950, when the needle 950 is in a start position, as shown in FIG. 29. The cannula may be made of any suitable material having sufficient rigidity to operate as described herein and may have sufficient flexibility for patient-user comfort, including, but not limited to metal, plastic, ceramic, glass, composite material or the like. The nest 956 may be made of any suitably rigid material that also has sufficient flexibility to operate as described herein, including, but not limited to metal, plastic, ceramic, glass, composite material or the like. In one embodiment, the nest 956 is made of a relatively flexible or soft material, such as, but not limited to a silicon, plastic or other suitable material, to provide a sealing function, as described below. The nest 956 is rigidly secured to one end of the cannula 954. In further embodiments, the nest 956 and cannula 954 may be formed as a single, unitary member.

The cannula 954 and nest 956 are initially supported on the needle 950 in the start position, with the needle 950 extending through the hollow interior of the cannula 954 and with the sharp end 950a of the needle 950 extending beyond one end of the cannula 954, as shown in FIG. 29. The cannula 954 and nest 956 move with the movement of the needle, from the initial start or retracted position of FIG. 29, to the extended position of FIG. 30. The nest 956 is provided with one or more locking tabs 956a for engaging and abutting one or more stop surfaces 958 on the housing 944, when the cannula 954 and nest 956 reach the extended position of FIG. 30. The locking tab(s) 956a may be suitably flexible, to flex enough to ride over the portion of the housing 944 adjacent the stop surface(s) 958 and then flex back into engagement with the stop surface(s) 958. When the locking tab(s) 956a lock into place against the stop surface(s) 958, the cannula 954 and the nest 956 are locked into an extended position, as shown in FIGS. 30 and 31. Once the cannula 954 and nest 956 are locked into place, the needle 950 may be retracted back to the retracted position, while leaving the cannula 954 in the extended position, as shown in FIG. 31.

A pair of spring members 960 and 962 and lever members 964 and 966 are provided to impart a force on the needle 950 and cannula 954, in the axial dimension $A_4$, to move the needle 950 and cannula 954 from the start position (shown in FIG. 29), in the direction of arrow 968, to the extended position (shown in FIG. 30).

As shown in FIG. 29, the lever 964 is connected to the needle 950, adjacent the needle end 950b and is moveable with the needle 950, between the retracted or start position (of FIG. 29) to the extended position (of FIG. 30) and back to a retracted position (of FIG. 31). The lever 964 extends through the slot 948 in the housing 944 and moves linearly along the slot 948, as the needle 950 is moved between the retracted or start position (of FIG. 29) to the extended position (of FIG. 30) and back to a retracted position (of FIG. 31).

The spring 960 is a spring wire that has a pair of ends (one end shown in FIG. 28) that are connected in a fixed relation to the housing 944. For example, each end of the spring 960 may be wrapped around a grooved protrusion or ear 969 on the housing 944, and held in place by the natural spring force of the spring 960. The spring 960 is configured to be bent against its natural spring force, into the position shown in FIG. 28, wherein a portion 960a of the spring 960 extends over the lever 964, but is urged in the direction of arrow 968 by the natural spring force of the spring 960. The portion 960a of the spring 960 is initially held within a groove in the lever 966. The lever 966 is supported by the housing 944 for pivotal motion in the direction of arrow 970.

Upon pivoting of the lever 966 in the direction of arrow 970 (for example, by application of manual or mechanical force on the lever 966 in the direction of arrow 970), the portion 960a of the spring 960 is released from the lever and abuts the lever 964. Upon abutting the lever 964, the spring 960 imparts a force on the lever 964 in the direction of arrow 968, to move the needle 950 from the retracted or start position of FIGS. 28 and 29 to the extended position of FIG. 30. Upon reaching the extended position of FIG. 30, the continued motion or momentum of the spring 960 causes the tip of the lever 964 to break or bend away, freeing the spring 960 from the lever 964. Once the spring 960 is freed from the lever 964, the lever 964 (and the needle 950 connected to the lever 964) is moved back to the retracted position (as shown in FIG. 31), under the force of the spring 962. In particular, the spring 962 has a pair of ends that are connected in a fixed relation to the housing 944, similar to the manner described above for spring 960. A central portion 962a of the spring 962 is arranged adjacent and in abutment with the lever 964, to move the lever 964 in the direction opposite to arrow 968, from the extended position of FIG. 30 to the retracted position of FIG. 31.

The relative spring strengths of the springs 960 and 962 are selected such that the spring force of the spring 960 (for moving the lever 964 from the retracted or start position of FIG. 29 to the extended position of FIG. 30) is sufficiently greater than the spring force of the spring 962 (for moving the lever 964 from the extended position of FIG. 30 to the retracted position of FIG. 31). Also, the material from which the lever 964 is made is selected to provide the break-away or bending feature, to allow the spring 960 to free itself from the lever 964, when the lever reaches the extended position of FIG. 30.

Accordingly, in operation, the needle 950, cannula 954, springs 960 and 962 and levers 964 and 966 are arranged as shown in FIGS. 28 and 29, in a retracted or start position. To activate the device, a user may manually (or mechanically) pivot the lever 966 to release the spring 960 and cause the spring 960 to force the lever 964 toward the extended position. As the lever 964 moves toward the extended position, the needle 950 and cannula 954 are also moved with the lever 964 to the extended position of FIG. 30. In the extended position, the cannula nest 956 locks the cannula 954 in place in the extended position. In addition, the spring 960 frees itself from the lever 964 and allows the spring 962 to move the lever 964 back to the retracted position. As the lever 964 moves back to the retracted position, the needle 950 is also moved back to the retracted position, as shown in FIG. 31. In the retracted position, the needle 950 provides a hollow conduit, connecting the conduit 952 in fluid-flow communication with the cannula 954. Accordingly, the cannula 954 may be placed in the extended position and in fluid-flow communication, through the conduit 952, with a reservoir or other fluid source.

By supporting the housing 944 at an injection site (either in the disposable housing portion 20, the durable housing portion 22 or an injection site module), the housing 944 may be arranged adjacent a patient-user's skin (for example, when the disposable housing portion 20, the durable housing portion 22 or the injection site module is arranged adjacent the patient-user's skin, as described above), to allow the sharp end of the needle 950 to pierce the patient-user's skin and to allow the cannula 954 to be inserted at least partially into the patient-user's skin, when the needle is in the extended position of FIG. 30.

Figure 32:
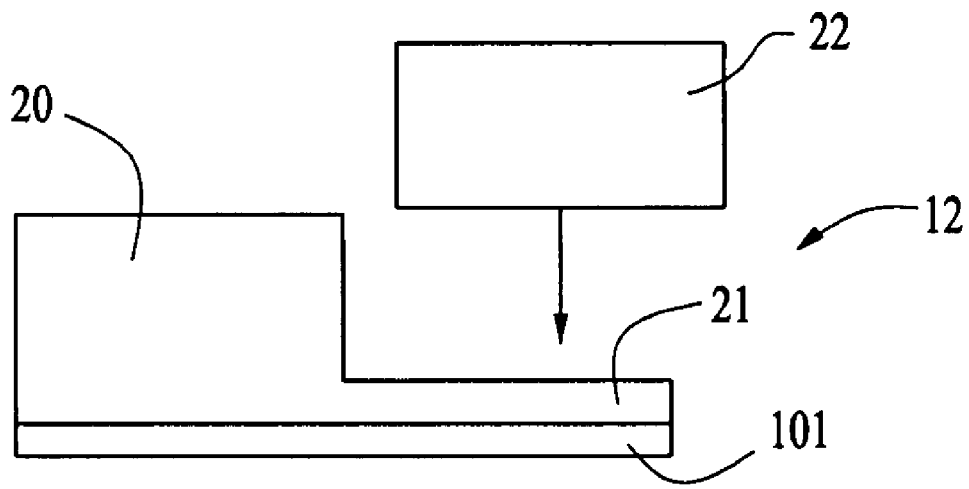
FIG. 32 shows a schematic side view of an arrangement of a durable housing portion and a disposable housing portion of a delivery system according to an embodiment of the invention consistent with the embodiment of FIG. 3.

In delivery device embodiments described above, a needle injector device is provided on a disposable housing portion (e.g., 20 in FIG. 3), where the disposable housing portion is provided with a base portion 21 that may be secured to the patient-user's skin by, for example, but not limited to, an adhesive material provided on the bottom surface of the base portion 21. That arrangement is generally represented, in side view, in FIG. 32, wherein an adhesive material 101 is provided on the bottom surface (skin-facing surface) of the base 21 of the disposable housing portion 20. As shown in FIGS. 2, 3 and 32, the durable housing portion 22 may be configured to be arranged on the base 21 of the disposable housing portion 20 to engage and connect to the disposable housing portion 22. In such an arrangement, the base 21 may be disposed between the durable housing portion 22 and the patient-user's skin, during operation, such that only the base 21 of the disposable housing portion remains in contact with the patient-user's skin, during operation.

Figure 33:
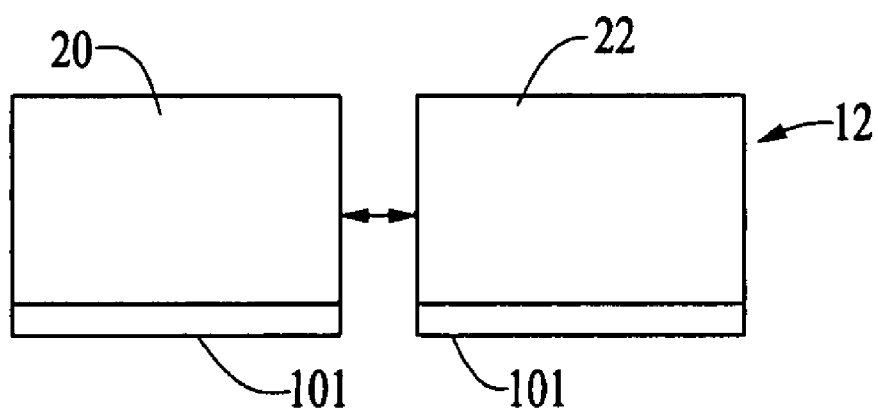
FIG. 33 shows a schematic side view of an arrangement of a durable housing portion and a disposable housing portion of a delivery system according to another embodiment of the invention.

However, in other embodiments, the durable housing portion 22 and the disposable housing portion 20 may be configured to engage each other in a side-by-side arrangement, for example, as shown in FIG. 33. In the side-by-side arrangement in FIG. 33, either one or both of the durable housing portion 22 and the disposable housing portion 20 may be provided with an adhesive material 101 (and a peelable cover layer 23 as shown in FIG. 3).

Figure 34:
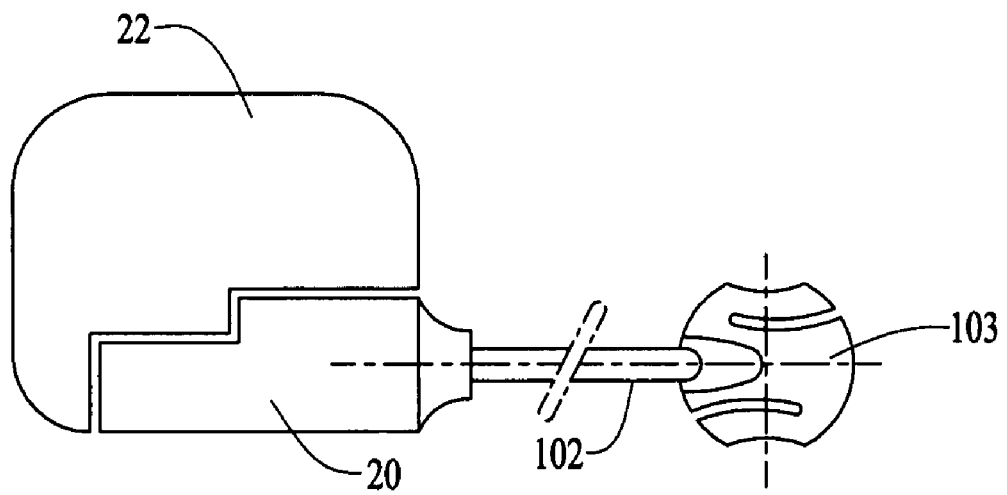
FIG. 34 shows a schematic top view of an arrangement of a durable housing portion and a disposable housing portion of a delivery system according to an embodiment of the invention.

Also, while embodiments described above may include an on-board needle or cannula injector device as described herein that may be activated through the operator or opening 25, other embodiments may employ an injection site module 103 that is external to the disposable housing portion 20, but connected to the disposable housing portion 20, through a suitable conduit 102, as shown in FIG. 34. The external injection site module 103 may include a needle or cannula injector device structure and an operator or opening (similar to the operator or opening 25 described above) through which the injector device may be activated. Alternatively or in addition, the external injection site module 103 may include an infusion set such as, but not limited to an infusion set as described or referenced in U.S. patent application Ser. No. 10/705,686, filed Nov. 10, 2003, titled "Subcutaneous Infusion Set" (Publication No. 2005/0101910) and/or U.S. patent application Ser. No. 11/004,594, filed Dec. 3, 2004, titled "Multi-Position Infusion Set Device And Process" (Publication No. 2006/0129090), each of which is assigned to the assignee of the present invention and each of which is incorporated herein by reference, in its entirety.

The conduit 102 that connects the module 103 with the disposable housing portion 20 may be any suitable tubing structure having a fluid flow passage, such as, but not limited to, a flexible tube made of plastic, silicone or the like. An adhesive material may be provided on the tubing structure (or between the tubing structure and the patient-user's skin) to secure the tubing to the patient-user's skin. By locating the injection site module 103 external to the disposable housing portion 20, the disposable housing portion 20 and the durable housing portion 22 may be clipped to a patient-user's clothing, belt, suspender or other article of apparel or may be held in a pocket of an article of apparel or carried in a purse or the like.

In one embodiment, the conduit 102 may be fixed at one end to the disposable housing portion 20, in fluid-flow communication with the reservoir within the disposable housing portion 20, and fixed at a second end to an external injection site module 103, for connection in fluid-flow communication with a hollow needle or cannula, as described above. In further embodiments, one or both of the ends of the conduit 102 may include suitable connection structures that allow the conduit ends to be selectively connected in fluid-flow communication with, and selectively disconnected from the disposable housing portion 20 and/or the injection site module 103. Such connectors may comprise a hollow needle and septum, a Luer connector, or other suitable fluid-communication connectors. In such embodiments, the disposable housing portion 20 and the durable housing portion 22 may be disconnected from the module 103, for example, by disconnecting one of the ends of the conduit 102 from the module 103 or the disposable housing portion 20, while leaving the module 103 in place (without requiring the patient-user to withdraw the needle or cannula and, later, insert a needle or cannula to resume operation). In this manner, a patient-user may readily disconnect and remove the disposable housing portion 20 and durable housing portion 22, for example, to allow the patient-user to shower, bath, swim or conduct other activities, yet also allow the patient-user to readily re-connect the disposable housing portion 20 to the module 103, for example, upon completion of such activities.

Figure 35:
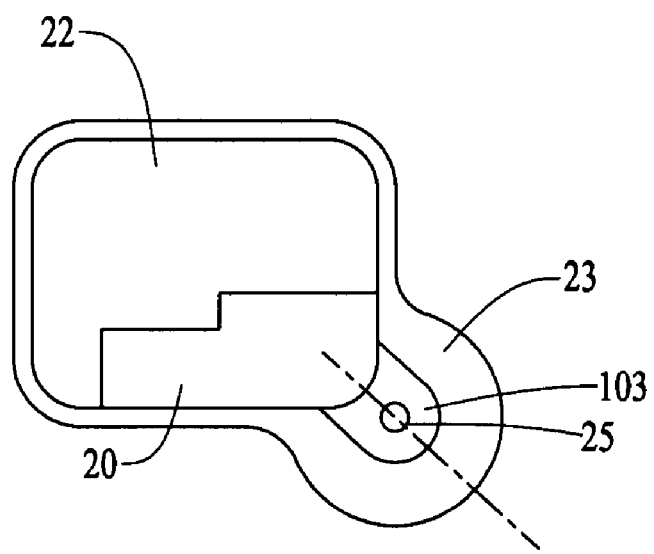
FIG. 35 shows a schematic top view of an arrangement of a durable housing portion and a disposable housing portion of a delivery system according to another embodiment of the invention.

In yet further embodiments, the conduit 102 may be eliminated and an injection site module 103 may be directly connected with the disposable housing portion 20, as shown in FIG. 35. In such an embodiment, one or more suitable fluid flow passages are provided through the disposable housing portion 20 and into the injection site module 103, for fluid-flow communication between the reservoir in the disposable housing portion 20 and a hollow needle or cannula, as described above. Also, in such embodiments, the injection site module 103 and the disposable housing portion 20 may include mating connection structures to allow the injection site module 103 and the disposable housing portion 20 to be selectively connected and disconnected from each other.

Figure 36:
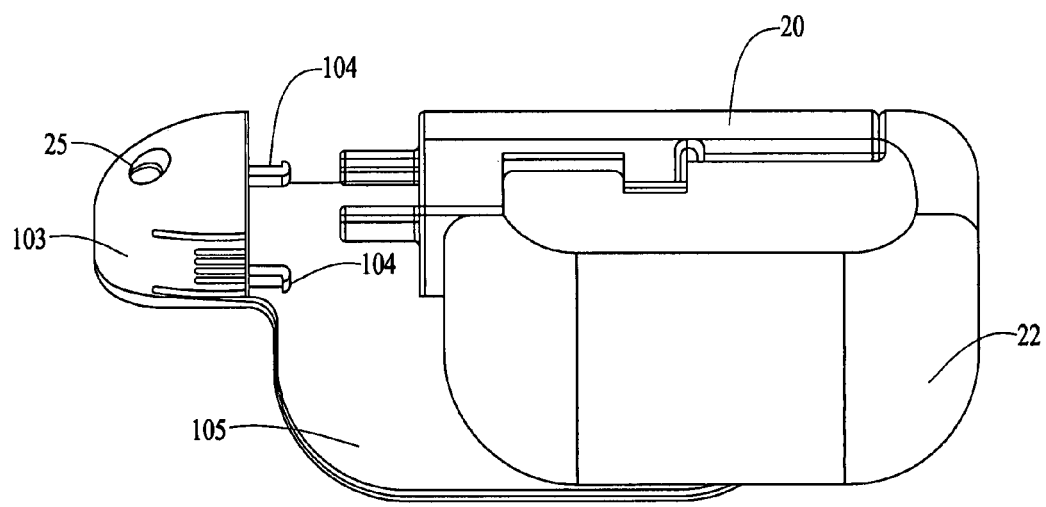
FIGS. 36 and 37 show a perspective view of a connection arrangement for a disposable housing portion and an injection site module.
Figure 37:
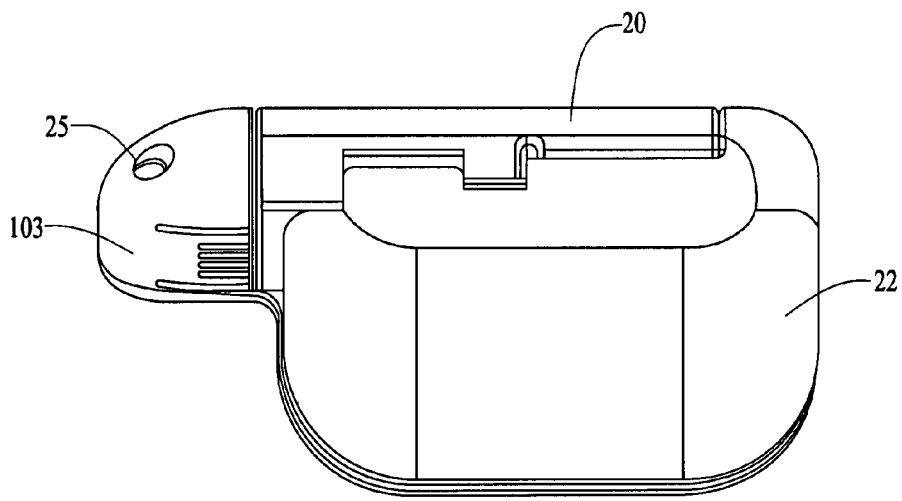

Various examples of mating arrangements, for directly connecting an injection site module 103 to a disposable housing portion are described with reference to FIGS. 36-41. FIGS. 36 and 37 show an example arrangement, in which an injection site module 103 includes at least one (two in FIG. 36) protruding engagement pawl 104 that are configured to be received in a corresponding number of receptacles on the disposable housing portion 20 (similar to the pawls 74 and receptacles 76 described in U.S. Patent Application No. 60/839,741, titled INFUSION PUMPS AND METHODS AND DELIVERY DEVICES AND METHODS WITH SAME, filed Aug. 23, 2006, which has been incorporated herein by reference. In other embodiments, the pawl(s) 104 may be located on the disposable housing portion 20, while the corresponding receptacles may be located on the module 103. In yet other embodiments, each of the disposable housing portion 20 and the module 103 may include one or more pawls and one or more receptacles.

The pawls 104 and receptacles may be configured to allow a patient-user to manually slide the pawls into the receptacles as the disposable housing portion 20 and the module 103 are brought together. When the pawls 104 are received in the corresponding receptacles, the module 103 is secured to the disposable housing portion 20. The pawls 104 may include a shaped portion or head to provide a snap-fit with the receptacles, when the pawls 104 are fully received within the receptacles. The pawls 104 may be configured with sufficient flexibility to allow the patient-user to separate the disposable housing portion 20 from the module 103, by applying a sufficient force to pull those two parts away from each other and unsnap the pawls 104 from the receptacles. In the embodiment of FIGS. 36 and 37, the module 103 may be attached to or may include a base portion 105 that may be secured to a patient-user's skin during operation, in lieu of the extended base 21 of the disposable housing portion 20 described above. The base portion 105 may include an adhesive material and peelable cover layer as described above with respect to the base 21 of the disposable housing portion 20.

Figure 38:
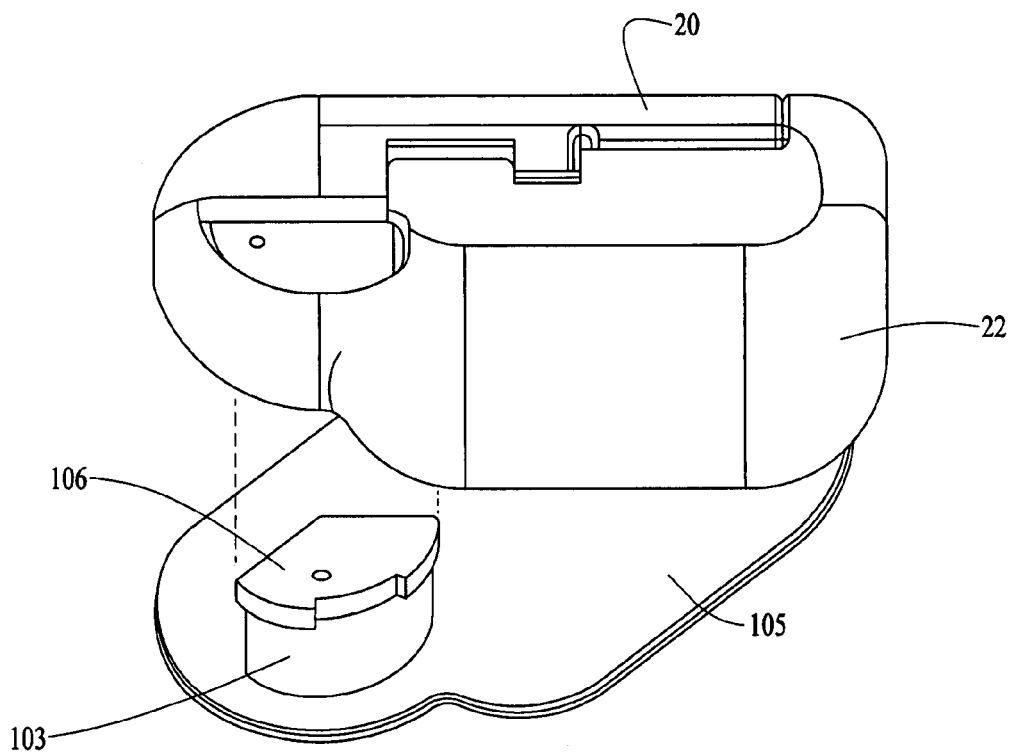
FIGS. 38 and 39 show a perspective view of another connection arrangement for a disposable housing portion and an injection site module.
Figure 39:
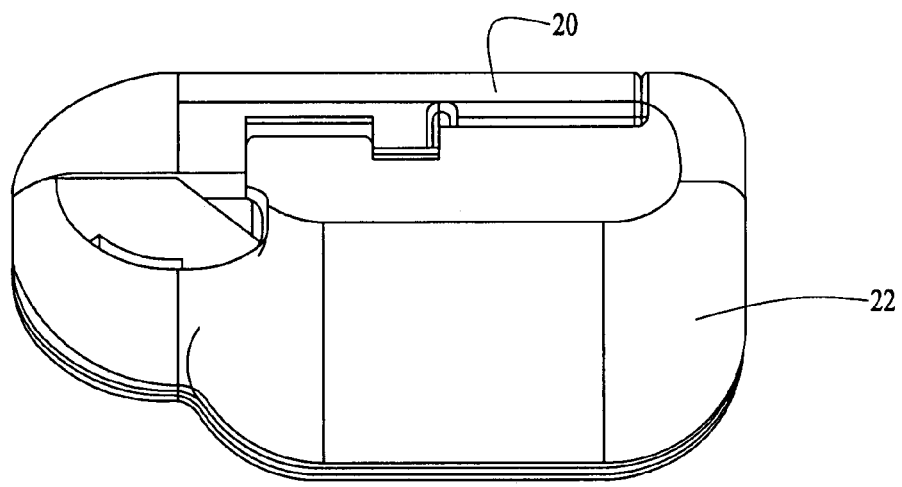

Another example of a connection structure is described with reference to FIGS. 38 and 39, wherein the module 103 includes a shaped head 106 configured to be received within a correspondingly shaped opening or receptacle in the disposable housing portion 20. The shaped head 106 may be configured with a shape that allows the head to be received in the receptacle when the disposable housing portion 20 is aligned relative to the module 103 in a first alignment position, as shown in FIG. 37, and further allows the disposable housing portion 20 to be rotated relative to the module 103 while the head 106 is received within the receptacle to a second alignment position as shown in FIG. 39. The receptacle in the disposable housing portion 20 may be shaped to allow the head 106 to be freely received or removed from the receptacle, when the disposable housing portion 20 is in the first alignment position (FIG. 38), yet abut the head 106 and inhibit separation of the head 106 from the receptacle (and, thus, inhibit separation of the disposable housing portion 20 from the module 103), when the disposable housing portion is in the second alignment position (FIG. 39).

Figure 40:
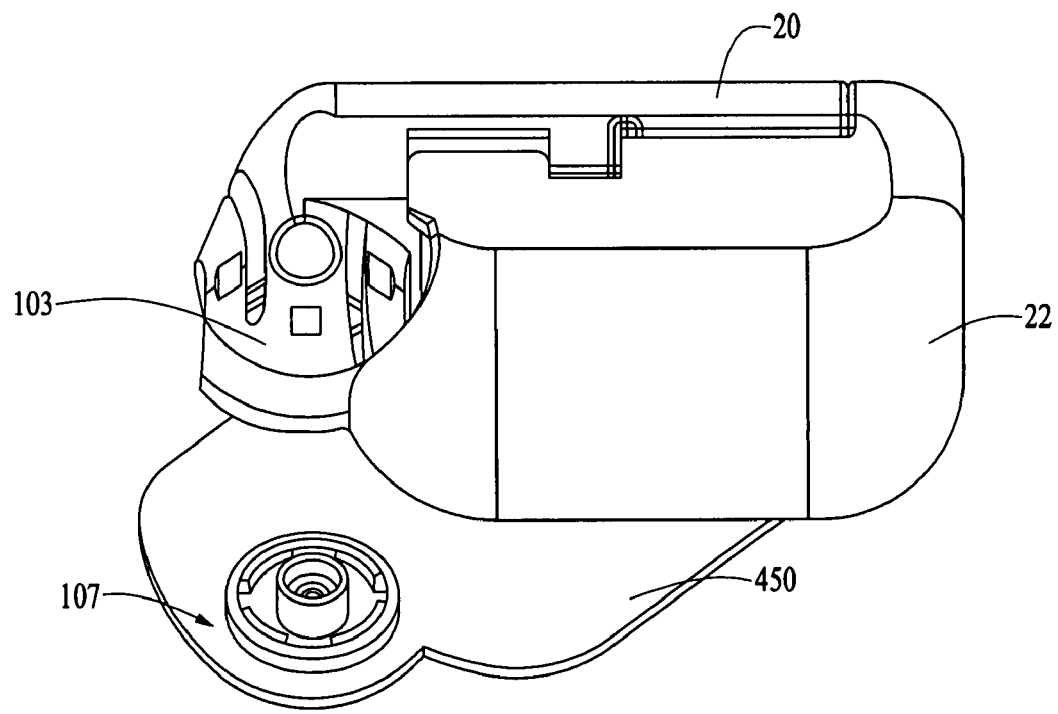
FIGS. 40 and 41 show a perspective view of yet another connection arrangement for a disposable housing portion and an injection site module.
Figure 41:
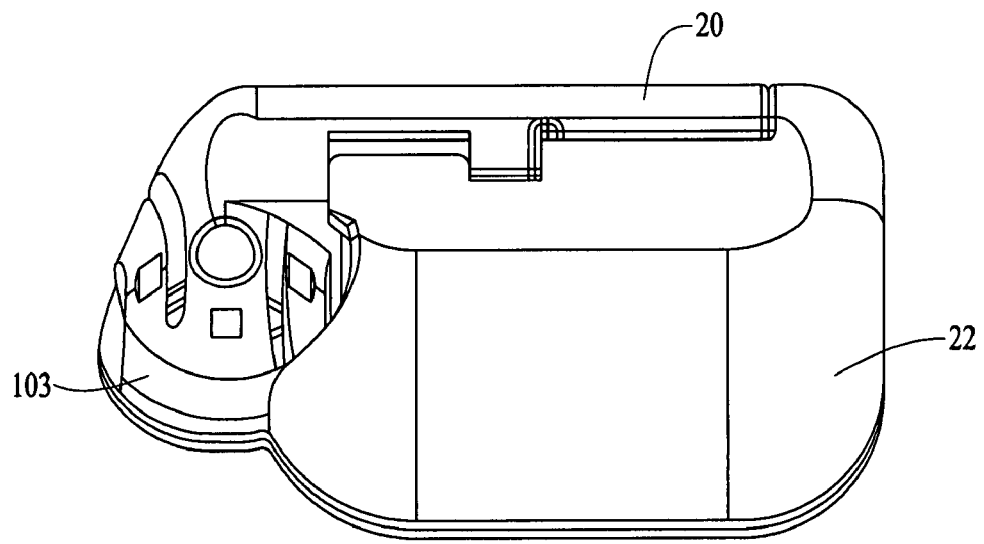

A further example of a connection structure is described with reference to FIGS. 40 and 41, wherein the module 103 includes a shaped receptacle 107 configured to receive a correspondingly shaped connector member in the disposable housing portion 20. The shaped receptacle 107 may be configured with a shape that allows the connector member of the disposable housing portion to be engaged with the receptacle 107 when the disposable housing portion 20 is aligned relative to the module 103 in a first alignment position, as shown in FIG. 40, and further allows the disposable housing portion 20 to be rotated relative to the module 103, while the receptacle 107 is engaged within the connector member, to a second alignment position as shown in FIG. 41. The receptacle 107 and the connector member in the disposable housing portion 20 may be shaped to allow the connector member to be freely engage the receptacle 454, when the disposable housing portion 20 is in the first alignment position (FIG. 40), yet lock with the receptacle 107 and inhibit separation of the connector member from the receptacle (and, thus, inhibit separation of the disposable housing portion 20 from the module 103), when the disposable housing portion is in the second alignment position (FIG. 41). The receptacle 107 and connection member may include any suitable known rotary connection structures for connecting two structures together upon engagement and relative rotation of the two structures in one direction, yet allow the two structures to be disengaged and separated from an engaged arrangement, by relative rotation of the two structures in the second, opposite direction.

In yet further embodiments, the injection site module may be formed as a unitary structure with the disposable housing portion 20. Also, in any of the embodiments described above, one or more sensors may be located in the disposable housing portion 20, the injection site module 103 or the durable housing portion 22, for sensing a biological condition, including, but not limited to, blood glucose level, level of infusion medium in the patient-user's blood and/or other conditions. Such sensor(s) may include a hollow needle or cannula and/or a set of micro-needles, as described above, for piercing the patient-user's skin to convey fluid from the patient to the sensor.

Also, various embodiments described above may employ a reservoir 28 that, in some examples, may include a canister that is removable from and insertable into the first or disposable housing portion 20. In this manner, a reservoir cartridge may be removed and replaced with a new, refilled, pre-filled, user-filled, refurbished or remanufactured cartridge. In such embodiments, the reservoir cartridge may include an electronic storage device (such as an electronic memory chip or the like) for storing information, such as, but not limited to, identification of the contents of the reservoir, identification of the maker of the reservoir or its contents, information relating to the state of fill or depletion of the reservoir, or the like. Suitable electrical contact pads located in the disposable housing portion may electrically connect with contact pads on the reservoir, to electrically connect the electronic storage device on the reservoir canister with suitable electronics in the disposable housing portion or the durable housing portion 22, for reading information stored on the electronic storage device. Such information (or other information, warnings, etc., associated with the stored information) may be displayed on a display device on the durable housing portion 22, when the reservoir canister is inserted into the disposable housing portion 20, and the disposable housing portion 20 and the durable housing portion 22 are engaged.

In addition, in any of the above-described embodiments, one or both of the disposable housing portion 20 and the durable housing portion 22 (and/or a separate base portion 105 or a separate injection site module 103) may include a force sensor (not shown) or other suitable sensing device for sensing the proper placement or engagement of one or more of the disposable housing portion 20 and the durable housing portion 22 (and/or a separate base portion or a separate injection site module) on a patient-user's skin (or other proper location for operation with the patient). In such an embodiment, further electronics may control the operation of the drive device to inhibit operation of the drive device and/or the needle injector, unless the sensor senses the proper operable engagement of one or more of the disposable housing portion 20 and the durable housing portion 22 (and/or a separate base portion or a separate injection site module) with the patient-user's skin (or other proper location for operation).

Alternatively or in addition, one or both of the disposable housing portion 20 and the durable housing portion 22 may include a sensing device (not shown) for sensing the proper operable engagement of the disposable housing portion 20 and the durable housing portion 22 together (and/or with a separate base portion or a separate injection site module). In such an embodiment, further electronics may control the operation of the drive device to inhibit operation of the drive device and/or the needle injector, unless the sensor senses the proper operable engagement of the disposable housing portion 20 and the durable housing portion 22 together (and/or with a separate base portion or a separate injection site module).

In any of the above embodiments, a sensor may be provided in (or otherwise associated with) the reservoir to detect a low volume of infusion medium in the reservoir. For example, a sensor may be configured to detect a condition at which the volume of infusion medium in the reservoir reaches a threshold minimal level. A warning device may be operably connected to the sensor, to provide a warning signal, upon the detection of a low volume condition. The warning device may provide an audible warning sound, a visible warning signal and/or a tactile warning signal (such as, but not limited to a perceptible vibration) to the patient-user, upon the detection of the volume of infusion medium in the reservoir reaching a threshold minimal level. In one embodiment, the visible warning may be provided as a message on an electronic display (as described above) on the durable housing portion 22. Alternatively or in addition, a warning signal condition may be communicated to and displayed on a remote CCD 16 or computer 18 (FIG. 2), for example, through wireless communication electronics as described above.

In addition, while various embodiments described above may include one or more adhesive layers, each having a peelable cover layer, other embodiments may employ a single adhesive layer having (or plural adhesive layers, each having) a pattern of plural peelable cover layer portions, such that a patient-user may peel off one portion of the cover layer for adhering the delivery device to the patient-user as described above, while leaving the rest of the pattern of peelable cover layer portions on the adhesive. In such an embodiment, after completion of a first period of operation of the delivery device and removal of the delivery device from the patient-user, a second portion of the peelable cover layer may be removed from the adhesive layer and the delivery device may be adhered to a patient-user for a second period of operation.

Also, while various delivery device embodiments described above include base portions (for example, 105) that are configured to be secured to a patient-user's skin (or other suitable surface of operation) and that extend along the full length and width of the delivery device structure, other embodiments may employ base portions (that secure to the patient-user's skin or other surface) that are configured to be less than the full length or width dimension of the delivery device structure, to minimize the surface area in contact with the patient-user (or other surface) and, thus, improve patient-user comfort during operation. Base portions having shapes and sizes different from those shown in the accompanying drawings may be employed for additional improvements with regard to patient-user comfort and minimizing surface area in contact with the patient-user. Furthermore, as noted above, the base portion may be composed of a flexible material that at least partially conforms to the curvature and movement of the patient-user's body.

In any of the above-described embodiments in which an adhesive material is used to secure one or more of the delivery device components to the patient-user's skin (or other suitable surface for operation), multiple types of adhesive materials (or multiple strengths of adhesives) may be employed, such that a stronger adhesive is provided in certain areas (such as around the needle injection site), while a weaker adhesive is provided in other areas.

Figure 42:
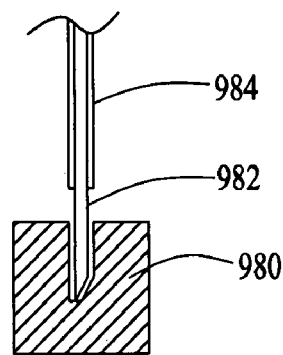
FIG. 42 is a cross-section view of a hollow needle and hydrophobic stop member for priming a hollow needle or cannula of a needle injector device, according to an embodiment of the invention.

In any of the above-described embodiments, a priming process may be carried out, prior to activation of the needle inserter, to convey fluid from the reservoir 28 to the hollow needle or cannula and/or fill the fluid flow path between the reservoir 28 and the hollow needle or cannula. In some embodiments, priming may be carried out before the delivery device (or component of the delivery device that contains the needle inserter) is secured to the patient user's skin. Priming may include running the drive device of the delivery device for a period of time, for example, but not limited to, a period of time until the user observes fluid at the tip of the hollow needle or cannula. In further embodiments, as represented by FIG. 42, a stop-member 980 may be provided, temporarily, at the tip of the hollow needle 982 (shown in FIG. 42 with a cannula 984 supported thereon) to allow passage of air out of the needle or cannula, but also provide a back pressure against flow of infusion medium fluid from the needle, for priming. The stop member may be made of or lined with a hydrophobic material, such as, but not limited to a hydrophobic membrane provided under the name GORE-TEX™ (a trademark of W.L. Gore & Associates, Inc.) or other suitable hydrophobic material. In further embodiments, the stop member may include a further material that changes color (or other perceptible characteristic) when in contact with an infusion medium, to provide a visual indication that priming is completed.

Figure 43:
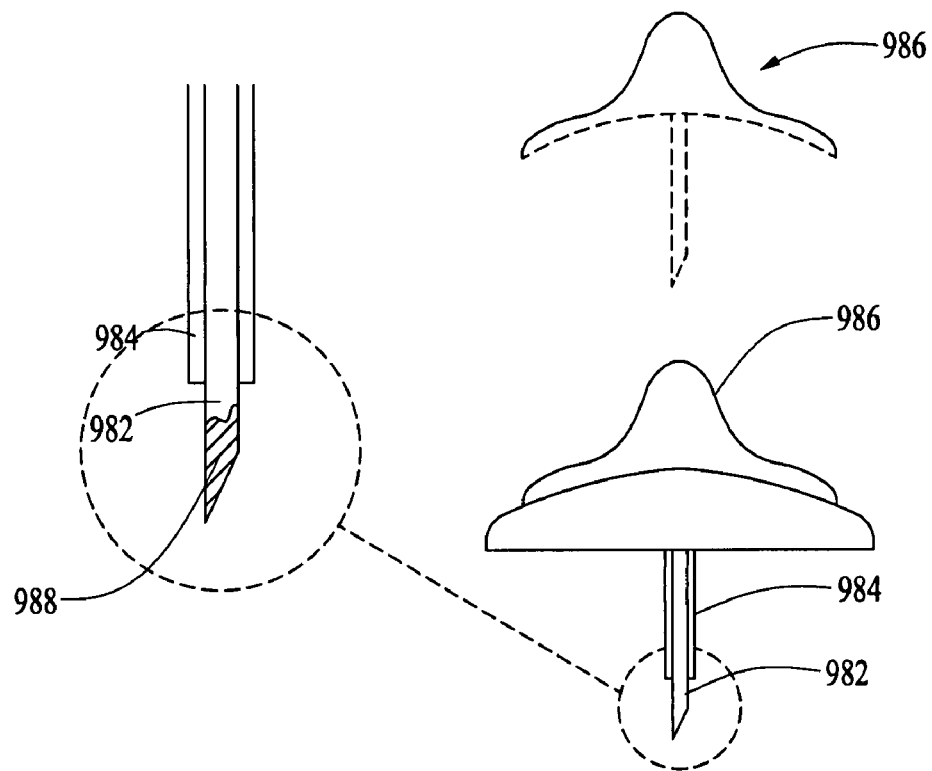
FIG. 43 is a side, schematic view of a hollow needle in a needle set having a hydrophobic material for priming.

In yet other embodiments of using a hydrophobic material during priming, a needle inserter set may include a removable needle hub that is positioned within a hollow cannula when the cannula is inserted into the patient-user's skin and removed, leaving the cannula in place, after insertion of the cannula, such as, but not limited to a needle set configuration as described in U.S. Pat. No. 4,755,173, which is incorporated herein by reference in its entirety, and/or as employed in products produced by Medtronic, Inc., under the product name Paradigm™ Quick-Set™ and Paradigm™ Sof-Set™, each of which is a trademark of Medtronic-MiniMed, Inc. or Medtronic, Inc. With reference to FIG. 43, in such embodiments, the hollow needle 982 of the needle hub 986 may include a hydrophobic material 988 at its tip, for providing a back pressure against fluid flow of liquid infusion medium, but allow air to escape from the hollow needle during priming. In such an embodiment, the interior surface of the hollow needle 982 may include a coating or layer of hydrophobic material 988 at or near its piercing end, as shown in FIG. 43. Alternatively, or in addition, a plug of hydrophobic material may be placed in the hollow needle 982, for example, at or adjacent the piercing end of the needle. Alternatively, or in addition, a stop member 980 as described above may be employed during priming, for enhancing back pressure against fluid flow of liquid infusion medium, while allowing air to escape from the hollow needle.

In such an embodiment, prior to insertion of the needle and cannula into a patient-user, the hollow needle extends through the cannula and is visible adjacent one end of the cannula. The drive device of the delivery device may be operated to drive fluid from the reservoir 28 to the hollow needle and cannula. The hydrophobic material at the tip of the hollow needle allows passage of air, but inhibits the infusion medium fluid from passing through the hollow needle. Upon running of the drive device for a defined period of time and/or until a completion of priming is detected, the needle and cannula may be inserted into the patient-user. After insertion of the needle and cannula, the needle may be removed from the cannula by withdrawing the needle hub from the remainder of the needle inserter set, leaving the cannula in place within the patient-user's skin and in fluid-flow connection with the reservoir.

Various aspects of the multiple embodiments described above may be employed independently or in combinations thereof. While particular embodiments of the present invention have been shown and described, it will be obvious to those skilled in the art that the invention is not limited to the particular embodiments shown and described and that changes and modifications may be made without departing from the spirit and scope of the claimed invention. For example, while embodiments are described above in the context of delivery devices for delivering an infusion medium from a reservoir to a patient-user, other embodiments may be operated to withdraw a fluidic medium from a patient-user (or other source) and transfer the fluidic medium to the reservoir. Such other embodiments may be operated by operating the drive device to increase the fluid-retaining volume of the reservoir and create a negative pressure sufficient to draw fluid from the patient-user (or other source) to which the hollow needle or cannula is secured.

What is claimed is:

1. A needle injector device for connection in fluid-flow communication with an inlet or outlet port of a reservoir, the needle injector device comprising:
    a housing structure having an interior volume;
    a moveable needle supported by the housing structure for movement at least between a retracted position and an extended position;
    a needle carriage supported for movement within the interior volume of the housing structure with the moveable needle, at least between the retracted position and the extended position, the needle carriage having a needle passage through which the moveable needle extends in a case where the moveable needle and the needle carriage are in the retracted position;
    a hollow needle or cannula attached to the needle carriage and moveable with the needle carriage at least between the retracted position and the extended position, the hollow needle or cannula having a central passage through which the moveable needle extends in a case where the moveable needle, the needle carriage, and the hollow needle or cannula are in the retracted position;
    a locking structure for locking the needle carriage and the hollow needle or cannula in the extended position in a case where the needle carriage and the hollow needle or cannula are moved to the extended position;
    a first bias member supported by the housing structure within the interior volume of the housing structure, the first bias member for moving the needle carriage toward the extended position;
    a lever supported within the interior volume of the housing structure, the lever moveable between a first lever position, in which the lever holds the moveable needle from movement in a direction toward the retracted position, and a second lever position, in which the lever separates from the moveable needle to allow movement of the moveable needle toward the retracted position;
    an engagement member for moving the lever to the second lever position as the needle carriage is moved toward the extended position; and
    a second bias member operatively coupled to the moveable needle, the second bias member imparting a bias force on the moveable needle in a direction toward the retracted position, the second bias member for withdrawing the moveable needle from at least a portion of the hollow needle or cannula in a case where the needle carriage is in the extended position and the lever is in the second lever position.

2. The needle injector device of claim 1, wherein the housing structure is securable to a patient-user's skin and wherein the hollow needle or cannula are located in a position to extend into the patient-user's skin, upon the housing structure being secured to the patient-user's skin and the needle carriage and the hollow needle or cannula are locked in the extended position.

3. The needle injector device of claim 1,
    wherein the housing structure is securable to a patient-user's skin, wherein the moveable needle is located in a position to pierce the patient-user's skin in a case where the housing structure is secured to the patient-user's skin and the moveable needle is moved to the extended position; and
    wherein the moveable needle is located in a position external to the patient-user's skin in a case where the housing structure is secured to the patient-user's skin and the moveable needle is in the retracted position.

4. The needle injector device of claim 1, wherein the second bias member comprises a spring.

5. A needle injector device for connection in fluid-flow communication with an inlet or outlet port of a reservoir, the needle injector device comprising:
    a housing structure;
    a moveable needle supported by the housing structure for movement at least between a retracted position and an extended position;
    a needle carriage supported for movement by the housing structure with the moveable needle, at least between the retracted position and the extended position, the needle carriage having a needle passage through which the moveable needle extends in a case where the moveable needle and the needle carriage are in the retracted position;
    a hollow needle or cannula attached to the needle carriage and moveable with the needle carriage at least between the retracted position and the extended position, the hollow needle or cannula having a central passage through which the moveable needle extends in a case where the moveable needle, the needle carriage, and the hollow needle or cannula are in the retracted position;
    a locking structure for locking the needle carriage and the hollow needle or cannula in the extended position in a case where the needle carriage and the hollow needle or cannula are moved to the extended position;
    a bias member operatively coupled to the moveable needle, the bias member for withdrawing the moveable needle from at least a portion of the hollow needle or cannula upon the needle carriage and the hollow needle or cannula being moved to the extended position;
    the housing structure including a wall having an opening through which an external plunger may be inserted for imparting a force on the moveable needle in a direction for moving the moveable needle to the extended position, the wall having an interior surface;
    the moveable needle comprising a needle head arranged adjacent the interior surface of the wall in a case where the moveable needle is in the retracted position; and
    the needle injector device further comprising a seal disposed between and in contact with the needle head of the moveable needle and the interior surface of the wall of the housing structure to provide a seal between the moveable needle and the interior surface of the wall in a case where the moveable needle is in the retracted position.

6. The needle injector device of claim 5, the needle head arranged to be contacted by the external plunger in a case where the external plunger is inserted through the opening in the wall of the housing structure and the moveable needle is in the retracted position.

7. The needle injector device of claim 5, wherein:
    at least one of the needle head and the interior surface of the wall includes an annular groove; and
    the seal comprising an annular seal disposed at least partially within the annular groove.

8. The needle injector device of claim 7, wherein the other one of the needle head and the interior surface of the wall has an annular protrusion for engaging the annular seal in a case where the moveable needle is in the retracted position.

9. The needle injector device of claim 1, wherein the locking structure comprises at least one pivotal or flexible pawl for engaging an engagement surface on the needle carriage upon the needle carriage being moved to the extended position.

10. The needle injector device of claim 1, wherein the needle carriage comprises:
a body having a fluid flow passage in fluid flow communication with the needle passage;
a further hollow needle connected in fluid flow communication with the fluid flow passage and arranged in a position to pierce a septum and be connected in fluid flow communication with a further fluid flow passage that is in fluid flow communication with a reservoir connector.

11. A delivery device for delivery of infusion medium to a patient-user, the delivery device comprising
a reservoir for containing an infusion medium and having an outlet port, a fluid conduit connected in fluid flow communication with the outlet port of the reservoir, a drive device operatively connectable to the reservoir, for selectively driving the infusion medium from the reservoir; and
a needle injector device according to claim 1, wherein the hollow needle or cannula is connected in fluid flow communication with the fluid conduit in a case where the needle carriage and hollow needle or cannula are in the extended position.

12. A needle injector device of claim 1, the needle injector device further comprising a manual actuator operable from outside of the housing structure, the manual actuator for selectively releasing the needle carriage to move under the force of the first bias member from the retracted position to the extended position.

13. A needle injector device of claim 1, wherein the first bias member comprises a spring.

14. A needle injector device of claim 1, wherein the first bias member comprises a coil spring extending between the needle carriage and an interior surface of the housing structure.

15. A needle injector device of claim 1, wherein the first bias member comprises a rotatable cam having a cam surface imparting a bias force on the moveable needle in a direction toward the extended position as the cam rotates.

16. A needle injector device of claim 15, wherein the rotatable cam comprises a disk-shaped member having a width that varies across its diameter.

17. A needle injector device for connection in fluid-flow communication with an inlet or outlet port of a reservoir, the needle injector device comprising:
a housing structure;
a moveable needle supported by the housing structure for movement at least between a retracted position and an extended position;
a needle carriage supported for movement by the housing structure with the moveable needle, at least between the retracted position and the extended position, the needle carriage having a needle passage through which the moveable needle extends in a case where the moveable needle and the needle carriage are in the retracted position;
a hollow needle or cannula attached to the needle carriage and moveable with the needle carriage at least between the retracted position and the extended position, the hollow needle or cannula having a central passage through which the moveable needle extends in a case where the moveable needle, the needle carriage, and the hollow needle or cannula are in the retracted position;
a locking structure for locking the needle carriage and the hollow needle or cannula in the extended position in a case where the needle carriage and the hollow needle or cannula are moved to the extended position;
a bias member operatively coupled to the moveable needle, the bias member for withdrawing the moveable needle from at least a portion of the hollow needle or cannula upon the needle carriage and the hollow needle or cannula being moved to the extended position;
a lever moveable between a first lever position, in which the lever holds the moveable needle from movement in a direction toward the retracted position, and a second lever position, in which the lever releases the moveable needle and allows the moveable needle to move toward the retracted position under force of the bias member;
a spring having a coil portion, a first arm, and a second arm, the first arm secured in a fixed relation relative to the housing structure and the second arm moveable from at least between a first position and a second position under a force provided by the coil portion;
wherein the spring is arranged at a location relative to the moveable needle to cause the second arm to apply a force to urge the moveable needle, the needle carriage, and the hollow needle or cannula to the extended position as the second arm moves toward the second position, and to move the lever from the first lever position to the second lever position with continued movement of the second arm toward the second position.

18. A needle injector device of claim 17, wherein the lever comprises a lever mounted for pivotal motion relative to the housing structure.

19. A needle injector device of claim 17, the needle injector device further comprising an actuator for holding the second arm of the spring in the first position and for selectively releasing the second arm of the spring to allow the second arm of the spring to move to the second position.

20. A needle injector device of claim 19, wherein the actuator comprises an operator accessible from outside of the housing structure.

21. A delivery device for delivering fluidic media to a user, the device comprising:
a housing structure adapted to be secured to a user's skin;
a reservoir having an interior volume for containing fluidic media, the reservoir having an outlet port, the reservoir operatively connectable to a drive device to selectively drive fluidic media out the outlet port from the interior volume;
a channel having a longitudinal axis extending at least partially through the housing structure and having a first end open toward the user's skin in a case where the housing structure is secured to the user's skin;
at least one engagement structure;
a cannula and a cannula nest having an engagement surface, the cannula and the cannula nest having a size and shape capable of moving in the channel to an extended position, the cannula extending into the user's skin upon the cannula and the cannula nest being in the extended position and the housing structure being secured to the user's skin, the engagement surface of the cannula and the cannula nest arranged to be engaged by the engagement structure upon the cannula and cannula nest being in the extended position, to hold the cannula and the cannula nest in the extended position;

a moveable needle supported by the housing structure for movement with the cannula and the cannula nest at least between a retracted position and an extended position;

a bias member for imparting a bias force on the moveable needle in a direction toward the retracted position;

the housing structure including a wall having an opening through which an external plunger may be inserted for imparting a force in a direction for moving the moveable needle, the cannula, and the cannula nest to the extended position at which the cannula and cannula nest are held by the engagement structure, and then releasing the moveable needle to allow the moveable needle to move toward the retracted position under the bias force of the bias member, the wall of the housing structure having an interior surface;

the moveable needle comprising a needle head arranged adjacent the interior surface of the wall in a case where the moveable needle is in the retracted position;

the delivery device further comprising a seal disposed between and in contact with the needle head of the moveable needle and the interior surface of the wall of the housing structure to provide a seal between the moveable needle and the interior surface of the wall in a case where the moveable needle seal is in the retracted position.

22. A delivery device for delivering fluidic media to a user, the delivery device comprising:

a housing structure adapted to be secured to a user's skin;

a reservoir having an interior volume for containing fluidic media, the reservoir having an outlet port, the reservoir operatively connectable to a drive device to selectively drive fluidic media out the outlet port from the interior volume;

a needle injector device coupled in fluid-flow communication with the outlet port of the reservoir, the needle injector device for inserting a hollow needle or cannula into the user's skin, upon the housing structure being secured to the user's skin, the needle injector device comprising:

a moveable needle supported by the housing structure for movement at least between a retracted position and an extended position;

a needle carriage supported for movement by the housing structure with the moveable needle, at least between the retracted position and the extended position, the needle carriage having a passage through which the moveable needle extends in a case where the moveable needle and the needle carriage are in the retracted position;

a hollow needle or cannula attached to the needle carriage and moveable with the needle carriage at least between the retracted position and the extended position, the hollow needle or cannula having a central passage through which the moveable needle extends in a case where the moveable needle, the needle carriage, and the hollow needle or cannula are in the retracted position;

a locking structure for locking the needle carriage and the hollow needle or cannula in the extended position in a case where the needle carriage and the hollow needle or cannula are moved to the extended position;

a first bias member supported by the housing structure within the interior volume of the housing structure, the first bias member for moving the needle carriage toward the extended position;

a lever (supported within the interior volume of the housing structure, the lever) moveable between a first lever position, in which the lever holds the moveable needle from movement in a direction toward the retracted position, and a second lever position, in which the lever separates from the moveable needle to allow movement of the moveable needle toward the retracted position;

an engagement member for moving the lever to the second lever position as the needle carriage is moved toward the extended position; and a second bias member operatively coupled to the moveable needle, the second bias member imparting a bias force on the moveable needle in a direction toward the retracted position, the second bias member for withdrawing the moveable needle from at least a portion of the hollow needle or cannula in a case where the needle carriage is in the extended position and the lever is in the second lever position.

23. The needle injector device of claim 1, wherein the first bias member comprises a spring for imparting a bias force on the needle carriage free of external force from outside of the housing.

24. The needle injector device of claim 5, wherein the seal is arranged to abut at least one of the wall and the moveable needle and seal the opening through the wall in a case where the moveable needle is in the retracted position.

25. The needle injector device of claim 5, wherein the seal is arranged to extend around the circumference of the opening in the at least one of the wall and the moveable needle and seal the opening through the wall in a case where the moveable needle is in the retracted position.

26. The needle injector device of claim 5, the housing having an interior volume;

the opening through the wall of the housing providing access to the interior volume of the housing from outside of the housing; and the seal arranged to seal the opening through the wall in a case where the moveable needle is in the retracted position.

27. The delivery device of claim 22, wherein the second bias member comprises a spring that provides the bias force on the needle carriage free of external force from outside of the housing.

28. The needle injector device of claim 5, wherein the seal is arranged to provide a seal encircling the opening.

29. The needle injector device of claim 1, the second bias member for withdrawing the moveable needle from at least a portion of the hollow needle or cannula automatically upon the first bias member moving the needle carriage to the extended position.

30. The needle injector device of claim 17, the housing structure having an interior volume, the lever supported within the interior volume of the housing structure.

31. The needle injector device of claim 1, the lever supported by the needle carnage.

32. The needle injector device of claim 31, the locking structure for locking the lever in the extended position in a case where the needle carriage and the hollow needle or cannula are moved to the extended position.

33. The needle injector device of claim 1, the lever arranged to be in contact with the moveable needle in a case where the lever is in the first lever position.

* * * * *